(12) United States Patent
Marine et al.

(10) Patent No.: US 10,767,182 B2
(45) Date of Patent: Sep. 8, 2020

(54) DIRECT AND SELECTIVE INHIBITION OF MDM4 FOR TREATMENT OF CANCER

(71) Applicants: VIB VZW, Ghent (BE); Katholieke Universiteit Leuven, K.U.Leuven R&D, Leuven (BE); **Agency for Science, Technology and Research (A*Star)**

(72) Inventors: Jean-Christophe Marine, Brussels (BE); Ernesto Guccione, Proteos (SG); Marco Bezzi, Proteos (SG)

(73) Assignees: VIB VZW, Ghent (DE); Katholieke Universiteit Leuven, K.U.Leuven R&D, Leuven (BE); Agency for Science, Technology and Research, Singapore (SG)

( * ) Notice: Subject to any disclaimer, the term of this patent is extended or adjusted under 35 U.S.C. 154(b) by 44 days.

(21) Appl. No.: 15/526,716

(22) PCT Filed: Nov. 16, 2015

(86) PCT No.: PCT/EP2015/076705
§ 371 (c)(1),
(2) Date: May 12, 2017

(87) PCT Pub. No.: WO2016/075333
PCT Pub. Date: May 19, 2016

(65) Prior Publication Data
US 2017/0314024 A1 Nov. 2, 2017

(30) Foreign Application Priority Data
Nov. 14, 2014 (EP) .................................... 14193193

(51) Int. Cl.
| | | |
|---|---|---|
| *C12N 15/113* | (2010.01) | |
| *A61K 31/7088* | (2006.01) | |
| *C12Q 1/6886* | (2018.01) | |
| *A61K 45/06* | (2006.01) | |
| *A61K 31/506* | (2006.01) | |
| *A61K 31/437* | (2006.01) | |
| *A61K 31/428* | (2006.01) | |
| *A61K 31/713* | (2006.01) | |

(52) U.S. Cl.
CPC ........ *C12N 15/1135* (2013.01); *A61K 31/428* (2013.01); *A61K 31/437* (2013.01); *A61K 31/506* (2013.01); *A61K 31/7088* (2013.01); *A61K 31/713* (2013.01); *A61K 45/06* (2013.01); *C12Q 1/6886* (2013.01); *C12N 2310/11* (2013.01); *C12N 2310/3233* (2013.01); *C12N 2320/31* (2013.01); *C12N 2320/33* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,841,274 B2 * | 9/2014 | Lathangue | C07K 14/4705 514/44 A |
| 9,408,885 B2 | 8/2016 | Marine | |
| 10,183,912 B2 * | 1/2019 | Wald | A61K 45/06 |
| 2005/0171026 A1 | 8/2005 | Hagiwara et al. | |
| 2014/0213582 A1 | 7/2014 | Duncan et al. | |
| 2016/0271163 A1 | 9/2016 | Marine et al. | |
| 2018/0010132 A1 * | 1/2018 | Mavrakis | C07K 16/40 |

FOREIGN PATENT DOCUMENTS

| | | |
|---|---|---|
| WO | 0061193 | 10/2000 |
| WO | 2015076705 A1 | 5/2015 |
| WO | 2016075333 | 5/2016 |

OTHER PUBLICATIONS

Gilkes et al (EMBO Journal (2006) 25, 5614-5625) (Year: 2006).*
Allende-Vega et al (Oncogene (2013) 32: 1-14) (Year: 2013).*
Chen et al (Cell. Mol. Life Sci. 65 (2008) 2763-2775) (Year: 2008).*
Ji et al (J Invest Dermatol 132:356-364, 2012) (Year: 2012).*
Wade et al (Mol Cancer Res 2009;7(1): 1-11, 2009) (Year: 2009).*
Lenos et al (Cancer Res; 72(16) Aug. 15, 2012) (Year: 2012).*
Lenos et al (Cancer Res; 72(16) Aug. 15, 2012) Supplementary Tables 1-6 (Year: 2012).*
Mancini et al (Current Genomics, 2009, 10, 42-50) (Year: 2009).*
Bezzi et al (Genes Dev 27:1903-1916, 2013) (Year: 2013).*
Roh et al., X1-011 enhances cisplatin-induced apoptosis by functional restoration of p53 in head and neck cancer, Apoptosis, Aug. 12, 2014, pp. 1594-1602, vol. 19, No. 11, Springer.
Albert et al., Meayamycin inhibits pre-messenger RNA splicing and exhibits picomolar activity against multidrug-resistant cells, Molecular Cancer Therapeutics, Aug. 2009, pp. 2308-2318, vol. 8, No. 8, American Association for Cancer Research.
Gembarska et al., MDM4 is a key therapeutic target in cutaneous melanoma, Nature Medicine, Jul. 22, 2012, pp. 1239-1247, vol. 18, No. 8.
PCT International Search Report, dated Jan. 27, 2016, PCT/EP2015/076705, 5 pages.
PCT Written Opinion of the International Searching Authority, dated Jan. 27, 2016, PCT/EP2015/076705, 7 pages.

* cited by examiner

*Primary Examiner* — Richard A Schnizer
(74) *Attorney, Agent, or Firm* — Patent Law Works, LLP

(57) ABSTRACT

The present application relates to the field of cancer, particularly that of cancers with high MDM4 protein levels (such as melanoma, breast, colon or lung cancers, glioblastoma, retinoblastoma, etc.). It is shown herein that direct and selective inhibition of MDM4, e.g., by antisense RNA, leads to growth inhibition of cancer cells and sensitization to chemo or targeted therapies. Also provided are simple ways of determining which patients are most amenable for such treatment by comparing specific transcript levels.

18 Claims, 33 Drawing Sheets
(27 of 33 Drawing Sheet(s) Filed in Color)
Specification includes a Sequence Listing.

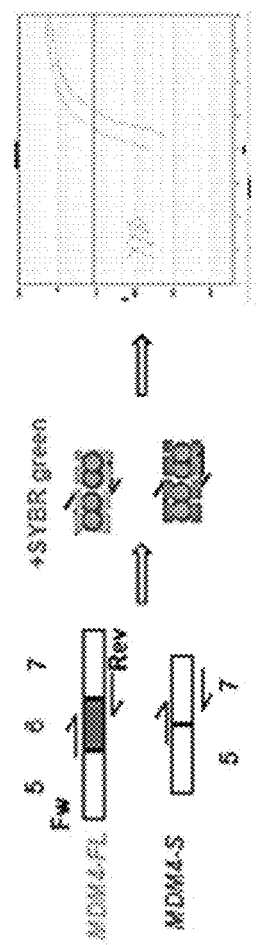
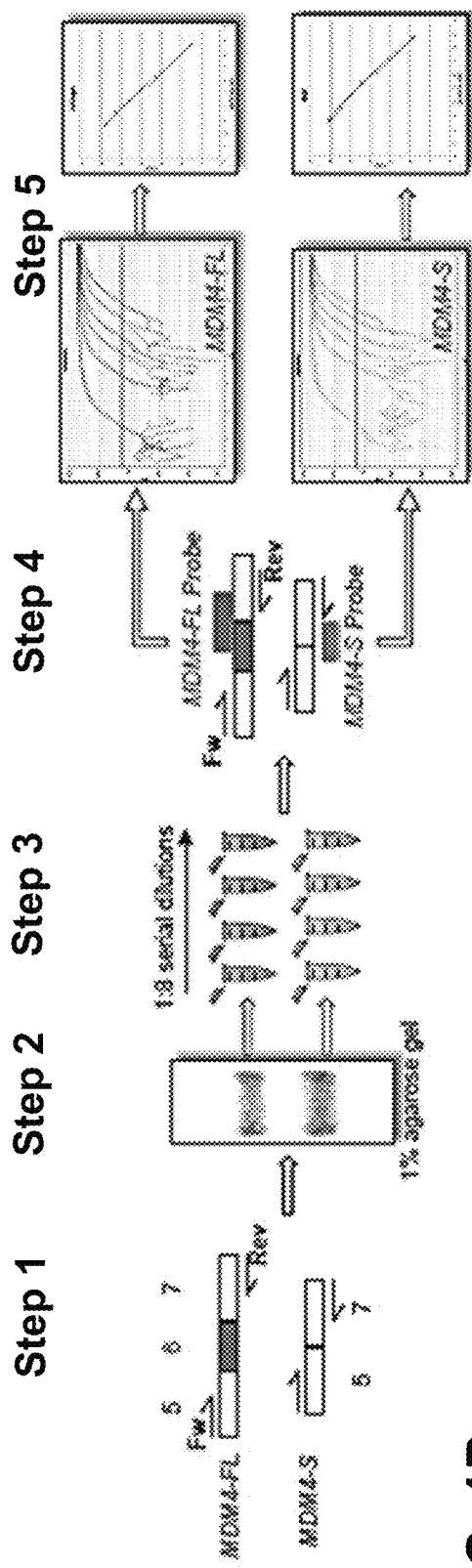
FIG. 1A
FIG. 1B

FIG. 2A
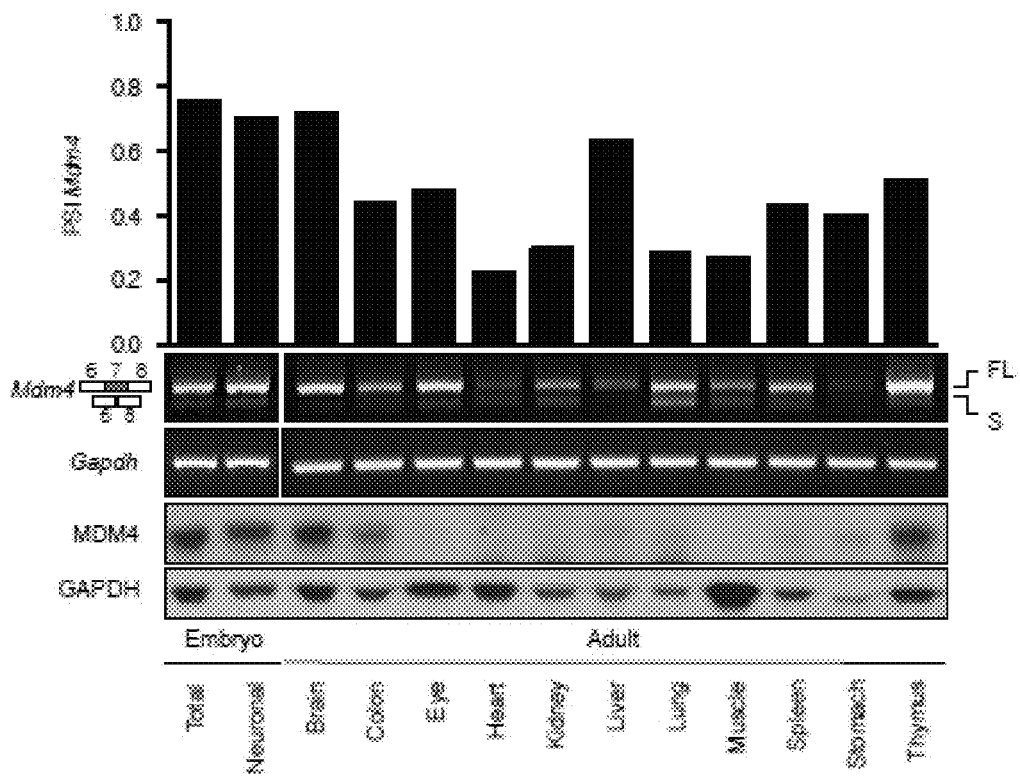
FIG. 2B
FIG. 2C
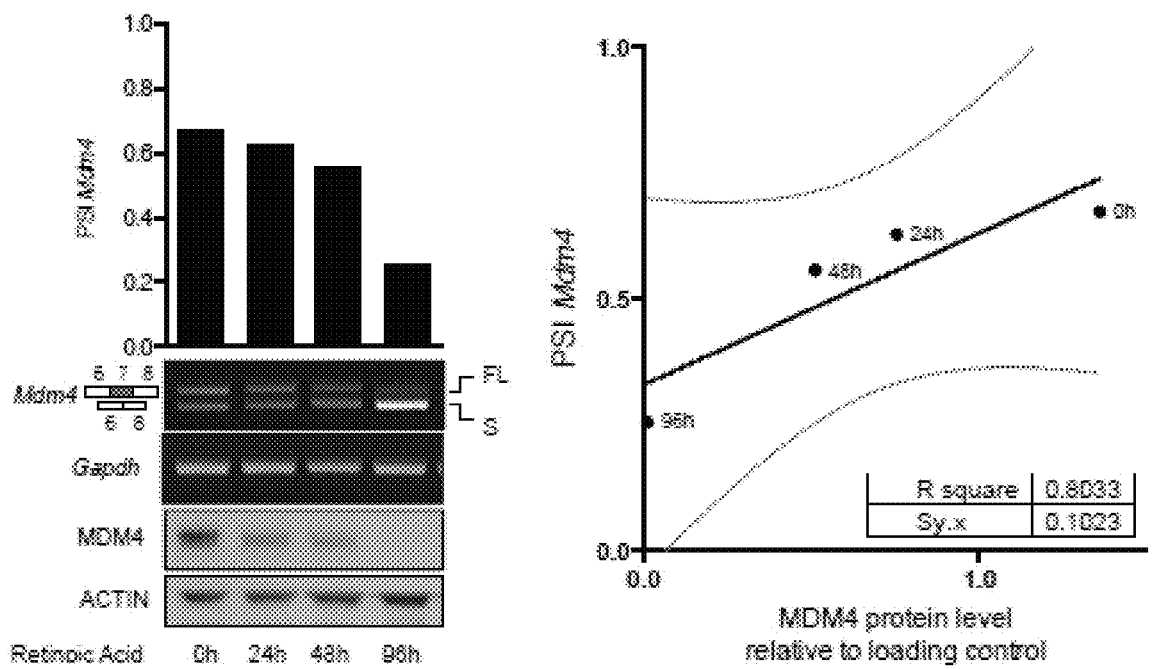

DIRECT AND SELECTIVE INHIBITION OF MDM4 FOR TREATMENT OF CANCER

CROSS-REFERENCE TO RELATED APPLICATIONS

This application is a national phase entry under 35 U.S.C. § 371 of International Patent Application PCT/EP2015/076705, filed Nov. 16, 2015, designating the United States of America and published in English as International Patent Publication WO 2016/075333 A1 on May 19, 2016, which claims the benefit under Article 8 of the Patent Cooperation Treaty to European Patent Application Serial No. 14193193.1, filed Nov. 14, 2014.

TECHNICAL FIELD

The present application relates to the field of cancer, particularly that of cancers (over)expressing MDM4, most (but not all) of which harbor wild-type TP53 (such as melanoma, breast cancer, prostate cancer, lung cancer, colon cancer, glioblastoma, retinoblastoma, etc.). It is also shown herein that the number of cancers overexpressing MDM4 is considerably higher than previously reported, as an increase of MDM4 protein levels does not necessarily correspond to an increase in total MDM4 mRNA levels, but rather to a specific mRNA isoform. It is shown herein that direct and selective targeting of MDM4 protein abundance, e.g., by antisense oligonucleotide-mediated exon skipping, leads to apoptosis of cancer cells. Also provided are simple ways of determining which patients are most amenable for such treatment by comparing specific transcript levels.

BACKGROUND

The MDM2-related protein MDM4 contributes to p53 inactivation during embryonic development (1). In contrast to MDM2, however, MDM4 is only expressed at low/undetectable levels in most adult tissues (2) and is largely dispensable for adult tissue homeostasis (3-6). Therefore, whereas MDM2 functions in both proliferating and terminally differentiated cells, MDM4 assists MDM2 in suppressing p53 only in highly proliferating cells such as during embryonic development or in the proliferative compartment of the intestinal epithelium (7). Consistently, MDM4 is expressed in the highly proliferating mouse Embryonic Stem (mES) cells and its expression decreases upon retinoic acid-induced differentiation (8).

MDM4 expression is often increased in cancer cells as one mechanism to inhibit p53-mediated tumor suppression. MDM4 mRNA expression is elevated in a substantial fractions of human tumors such as stomach and small intestine cancers (43%), glioblastomas (8%), colorectal cancers (20%) or breast cancers (20%) (9-12), but also, e.g., in lung cancer, osteosarcoma and melanoma (see particularly FIG. 4a of ref. 9; Table 2 of ref 10; Table 1 of ref. 11). The mechanism(s) that promote MDM4 expression in human tumors are not fully understood although of great interest as potential therapy targets. One such mechanism is gene amplification, occurring, for instance, in a small fraction of breast cancers (9). It was recently demonstrated that MDM4 protein, but not mRNA, levels are elevated in ~65% of cutaneous melanomas (13). This observation indicates that post-transcriptional mechanisms can also contribute to increased MDM4 expression in a subset of cancers (and emphasizes the need to develop a diagnostic assay that measures MDM4 at the protein level, which may be more difficult to implement in routine diagnostic labs); importantly, it also raises the possibility that thus far, the frequency of MDM4-expressing cancers has been underestimated, as most studies have focused on reporting MDM4 gene copy number variations and total mRNA levels.

This recent study established a causative link between MDM4 overexpression and melanoma formation in vivo and, importantly, underlined the addiction of melanoma cells to high levels of MDM4. MDM4 silencing decreased melanoma growth and this was, at least partly, a consequence of increased p53-dependent apoptosis. Consistently, targeting the physical interaction between MDM4-p53 by using SAH-p53-8, a small cell-penetrating stapled alpha-helical peptide, was sufficient to induce p53-dependent apoptosis in melanoma cells (13).

Although targeted therapy with BRAF-selective inhibitors such as vemurafenib has recently yielded impressive anti-tumor responses in melanoma patients carrying BRAFV600E mutations (14, 15), drug resistance is typically acquired within 12 months (16). Relapses can be postponed, but usually not avoided, when vemurafenib is combined with a selective MEK1/MEK2-inhibitor such as cobimetinib (17). Overcoming resistance to targeted therapies is likely to require targeting of multiple oncogenic mechanisms. Importantly, SAH-p53-8 sensitized melanoma cells to conventional chemotherapeutics and to inhibition of BRAFV600E by vemurafenib and inhibited growth of BRAFV600E-mutant melanoma cells that acquired resistance to BRAFV600E-inhibitors (13). These data indicate that targeting the MDM4-p53 interaction represents a unique therapeutic opportunity to reactivate suppressed p53 function in the context of anti-melanoma combination therapy. Since MDM4 is expressed in many other cancers as well (9-12), this strategy would be applicable in other tumors than melanoma as well.

For MDM2 inhibitors in development, side effects such as nausea, vomiting, fatigue, anorexia, insomnia, electrolyte imbalance, and mild renal/liver function impairment have been reported (Tabernero et al., 2009). MDM2 inhibition in normal tissue in mice leads to increased levels of apoptosis in the gut (Mendrysa et al., 2003), which leads to worries about therapeutic safety of these inhibitors. Indeed, a concern of therapies that aim to restore wild-type p53 activity is that these might lead to widespread apoptosis in normal tissues.

MDM4 might, therefore, be a safer and more promising anti-cancer therapeutic target. While it is not expressed in most normal adult tissues, many cancer cells, e.g., 65% of melanoma, up-regulate MDM4 to dampen p53 tumor suppressor function.

Unfortunately, small molecules that selectively and efficiently disrupt the MDM4-p53 complexes have so far not been identified/introduced into the clinic. Moreover, there is an increasing body of evidence that MDM4 possesses p53-independent oncogenic functions (2, 18-21). Consistently, in addition to induce p53-dependent apoptosis MDM4 silencing in melanoma cells also caused cell cycle arrest, that could not be rescued upon concomitant inactivation of p53 (13). Inhibition of melanoma growth upon MDM4 KD was more prominent than that seen upon inhibition of the MDM4-p53 interaction and could also be observed in some mutant p53 melanoma cells. These data point to p53-independent mechanisms of MDM4 oncogenicity in melanoma, in addition to its well-known ability to suppress p53.

Therefore, as an alternative to pharmacological inhibition of the MDM4-p53 protein interaction, which has proven to be very challenging, it was reasoned that targeting MDM4 abundance may not only be easier to achieve pharmacologically (and, therefore, easier to introduce into the clinic), but may have broader and more robust antitumor effects as this would inhibit both p53-dependent and independent oncogenic functions of MDM4.

It would be advantageous to identify compounds that can inhibit cancer growth, lack the toxicity associated with MDM2 inhibitors, and address both the p53-dependent and independent oncogenic functions of MDM4.

BRIEF SUMMARY

As an alternative to MDM2 inhibition, associated with concerns about systemic toxicity, and to pharmacological inhibition of the MDM4-p53 protein interaction, which has proven to be very challenging, it was reasoned that targeting the mechanisms that contribute to upregulation of MDM4 in cancer (in other words MDM4 protein abundance) may not only be easier to achieve pharmacologically (and, therefore, faster to introduce into the clinic) but may have broader and more robust antitumor effects as this would inhibit both p53-dependent and independent oncogenic functions of MDM4. MDM4 is a promising anti-cancer therapeutic target. It is highly expressed in ES cells and embryonic tissues, down-regulated during ES cells differentiation and undetectable in most normal adult tissues. Cancer cells often (i.e., 65% of melanoma) up-regulate MDM4, through yet unknown mechanisms, to dampen p53 tumor suppressor function and exploit its p53-independent oncogenic activities. Targeting the MDM4-p53 interaction is sufficient to unleash "dormant" p53 activity. However, small-molecule inhibitors of this interaction are yet to be identified and this strategy does not interfere with the increasingly recognized p53-independent oncogenic functions of MDM4.

Unexpectedly, it was found that MDM4 protein abundance strictly depends on a specific alternative splicing switch. Alternative splicing (AS) is one mechanism that modulates gene expression by adding or removing protein domains, affecting protein activity, or altering the stability of the mRNA transcripts (22, 23). Interestingly, the abundance of the MDM4 protein in ES cells decreases upon exposure to DNA damaging agents and this down-regulation is, at least partly, due to AS. For example, a decrease in the rate of splicing of two "detained" introns flanking exon 6 and subsequent nuclear retention of the unspliced transcript was shown to down-regulate MDM4 (24). In addition, it was previously demonstrated that defects in constitutive splicing efficiency decrease Mdm4 exon 6 inclusion, leading to the production of an unstable transcript known as Mdm4-S (lacking exon 6 in human or exon 7 in mouse), that contains a premature termination codon (25) and is targeted for non-sense-mediated decay (NMD) (26). Finally, homozygous mouse embryos engineered to skip Mdm4 exon 7 die in utero, just like Mdm4-null embryos, due to ectopic p53 activation (27). These data raise the possibility that human MDM4 exon 6/mouse exon 7 functions as an "NMD switch" exon (24) and that regulation of this splicing event may directly impact MDM4 protein expression levels.

While exon 6 skipping occurs during ES cells differentiation and in adult tissues, enhanced exon 6 inclusion, an event which is facilitated by the SRSF3 oncoprotein, leads to up-regulation of MDM4 in melanoma. MDM4 exon 6 skipping can be induced by compromising the splicing machinery genetically or pharmacologically or, more specifically, using antisense oligonucleotides (ASOs). This leads to decreased MDM4 abundance, activation of p53, growth inhibition and enhanced sensitivity of melanoma cells to chemotherapeutics and BRAF inhibitors.

Accordingly, as demonstrated herein, AS of exon 6 is the main post-transcriptional regulator of MDM4 protein abundance in both physiological conditions and in cancer. Moreover, an alternative therapeutic approach to MDM4 targeting is proposed, based on the use of Antisense Oligonucleotides (ASOs) that reduce MDM4 protein abundance rather than its ability to interact with p53 (and thus, importantly, inhibits both p53-dependent and independent oncogenic functions of MDM4). Evidence is provided that this clinically compatible strategy has robust antitumor effects and is applicable to a wide range of human tumors (namely MDM4-expressing cancers).

As shown in the Examples, the regulation of a single alternative splicing event determines the levels of MDM4 protein expression in cancer, such as in metastatic melanoma (MM). While high MDM4 levels require Exon 6 inclusion, alternative splicing of Exon 6, which generates the unstable MDM4s isoform, occurs in most normal adult tissues and in MM expressing low levels of MDM4. While measuring MDM4 protein levels is not always straightforward, these can be measured indirectly. For instance, the ratio between MDM4 full-length and MDM4 short-length transcripts, which can be easily determined in a single RT-PCR assay, predicts very accurately MDM4 protein levels and could, therefore, be used to identify high MDM4-expressor patients. Alternatively, instead of determining the ratio, one could detect and quantify, e.g., the levels of transcript that include exon 6 (or a region adjacent thereto, such as the exon 5-6 or 6-7 boundary). All of these patients expressing high levels of MDM4 would be particularly sensitive to MDM4 inhibition therapy.

It is an object of the disclosure to provide direct and selective inhibitors of MDM4 for use in treatment of cancer. With direct, it is meant that MDM4 is directly targeted (i.e., the MDM4 protein abundance is affected), so the inhibitors are not solely interaction inhibitors of MDM4-p53. This is important to inhibit p53-independent oncogenic functions of MDM4. With selective, it is meant that the inhibitors specifically inhibit MDM4, and do not inhibit MDM2. This is important to prevent deleterious side effects (i.e., iatrogenic effects caused by the therapy) in normal tissues.

This is equivalent as saying that methods of treating cancer in a subject in need thereof are provided, comprising a step of administering a direct and selective inhibitor of MDM4 to said subject.

According to particular embodiments, the cancer has high levels of MDM4 protein (i.e., is an MDM4 overexpressing cancer). More precisely, the cancer expresses more of the full-length MDM4 transcript (MDM4FL, which includes exon 6) than short MDM4 transcript (MDM4s, which doesn't include exon 6). In other words, the MDM4FL/MDM4s ratio is greater than one in said cancer. According to particular embodiments, the full-length transcript is at least 10%, at least 20%, at least 25%, at least 30%, at least 40% or even at least 50% more expressed than the short MDM4 transcript. According to further particular embodiments, the full-length transcript is at least 60%, at least 75%, at least 80%, at least 90%, or even at least 100% more expressed than the short MDM4 transcript. Thus, according to particular embodiments, the MDM4FL/MDM4s ratio is at least two. According to further particular embodiments, the MDM4FL/MDM4s ratio is at least three, at least four or at least five.

It is noteworthy that MDM4 is either not expressed or expressed at very low levels in adult tissues. Overexpression in cancer cells can thus also just be detectable expression of protein. According to particular embodiments, overexpression of MDM4 means that MDM4 protein is readily detectable by immunohistochemistry (IHC) and/or Western blotting. This corresponds to a MDM4FL/MDM4s transcript ratio greater than one, typically at least two.

According to particular embodiments, the cancer is selected from the group of breast cancer, lung cancer, prostate cancer, stomach cancer, testis cancer, larynx cancer, uterus cancer, colorectal cancer, melanoma, glioblastoma, osteosarcoma and retinoblastoma. According to more particular embodiments, the cancer is melanoma.

According to very specific embodiments, the cancer to be treated is a cancer wherein the TP53 gene is not mutated, i.e., a cancer with wild-type p53. (Please note that p53 may be inactivated, but is just not mutated.)

Although any direct and selective inhibitor of MDM4 can be suitable for the methods taught herein, it is particularly envisaged that the MDM4 inhibitor acts at the RNA level. More particularly, the inhibitor is an antisense oligonucleotide. The antisense oligonucleotides should affect MDM4 expression, e.g., by inducing MDM4 RNA degradation. Even more particularly envisaged is an antisense oligonucleotide that induces exon skipping. Most particularly, the exon that is skipped is exon 6.

Accordingly, also provided herein are MDM4 antisense oligonucleotides that induce exon skipping in the MDM4 transcript. Particularly, MDM4 antisense oligonucleotides that induce skipping of exon 6.

Such antisense oligonucleotides are also provided for use as a medicament. Particularly, they are provided for treatment of cancer (such as, e.g., breast, prostate, lung and colon cancers, melanoma, glioblastoma, retinoblastoma, or other cancers with a high MDM4 full-length/MDM4s ratio).

Alternatively, inhibitors of splicing machinery (e.g., Meayamycin, TG003, PRMT5 inhibitors, SmB inhibitors) can be administered to the tumor cells, thereby also inducing MDM4 exon skipping.

It is particularly envisaged that administration of the MDM4 inhibitor results in an increase in p53 activity. This can be measured, e.g., by increased expression of wt p53, increased activity of p53 itself, or upregulation of p53 targets.

Concomitantly, the inhibition of MDM4 results in an increased sensitivity to chemotherapeutic drugs and MAPK-targeting agents (as shown in the Examples section).

Accordingly, it is particularly envisaged that the inhibitor is used in a combination therapy with a chemotherapeutic or MAPK-targeting agent. The MDM4 inhibitor may be administered simultaneously with the other agent (e.g., chemotherapeutic), or before (or sometimes even after)—the important part is that they are administered within a time window so as to obtain a synergistic effect.

Also provided herein are methods of identifying tumors suitable for treatment with a direct and selective inhibitor of MDM4, comprising:
  Determining whether expression of MDM4 RNA (particularly full-length MDM4 RNA) is increased in the tumor or a sample of tumor cells;
  Establishing whether the tumor is suitable for treatment, wherein increased expression is indicative of suitability for treatment.

Increased expression is typically compared versus a control, e.g., versus a non-tumor (non-transformed) sample of the same tissue or cells.

More particularly, the methods comprise the steps of:
  Determining the expression ratio of MDM4 full-length RNA transcript over the MDM4 transcript lacking exon 6 in the tumor or a sample of tumor cells;
  Establishing whether the tumor is suitable for treatment, wherein a higher ratio is indicative of suitability for treatment.

Particularly, the ratio should be higher than one, i.e., a more full-length than short-length transcript is made in the sample. According to alternative embodiments, the ratio in the tumor should be higher than the same ratio in a control, e.g., in a non-tumor (non-transformed) sample of the same tissue or cells.

According to particular embodiments, the cancer has high levels of MDM4. More precisely, the cancer expresses more full-length MDM4 transcript (MDM4FL, which includes exon 6) than short MDM4 transcript (MDM4s, which does not include exon 6). In other words, the MDM4FL/MDM4s ratio is greater than one in said cancer.

According to particular embodiments, the cancer is selected from the group of breast cancer, prostate cancer, melanoma, glioblastoma and retinoblastoma. According to more particular embodiments, the cancer is melanoma.

The methods may optionally comprise a further step of administering a direct and selective inhibitor of MDM4 to the subject in which the tumor is present, particularly in those instances where the therapy would be suitable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C: Quantification of the MDM4-FL and MDM4-S isoforms using RTqPCR-methods. FIG. 1A: qPCR-analysis with primers specific for MDM4-FL and MDM4-S (human and murine) was run with Life Technologies' Fast SYBR® Green Master Mix on a Roche LIGHTCYCLER® 384. FIG. 1B: TAQMAN® assay. A reliable TAQMAN® assay was designed to simultaneously quantify the amount of full-length (FL) and short (S) MDM4 isoform in cDNA samples. FIG. 1C: Correlation plot between the PSI index and the MDM4 protein abundance, normalized for the protein loading control in embryonic and adult mouse tissues.

FIGS. 2A-2C: Unproductive splicing of Mdm4 leads to reduced protein abundance in most normal adult tissues and differentiated ES cells. FIGS. 2A and 2B: RT-qPCR analyses of Mdm4-FL and Mdm4-S isoforms in mouse embryonic (E14,5) and adult tissues (FIG. 2A) and in mES cells exposed to retinoic acid (FIG. 2B). Quantification of the PSI index using a SYBR® green-based qPCR in the various samples is shown in the top panels. Immunoblotting analysis of expression levels of MDM4 in the same samples is shown in the lower panels. Anti-GAPDH immunoblotting was used as loading control. FIG. 2C: Correlation plot between the PSI index (defined as the percentage of full-length Mdm4 mRNA (Mdm4-FL), which includes exon 7, over the total of all isoforms [Mdm4-FL/(Mdm4-FL+Mdm4-S)]) and MDM4 protein abundance, normalized for the protein loading control in mouse embryonic stem cells, upon retinoic acid-(RA-) induced differentiation.

FIG. 3A: Arches represent the relative exon-exon junction usage that was averaged among TCGASKCM melanoma samples and inferred from RNA seq data. Among all previously identified MDM4 isoforms (NCBI Refseq), MDM4-FL in blue and MDM4-S in red were by far the most abundant. MDM4-A (lacking exon 9, NM_001204171) in green was also detected but in a negligible amount. The other NCBI annotated isoforms were not detectable. FIG. 3B: The PSI index for all TCGA/SKCM tumor samples are calculated, sorted and plotted. A cut-off at the top 65% fraction shows a value of PSI MDM4=0.4. Red triangles indicate samples with a confirmed p53-inactivating mutation according to Kato et al. (28). FIGS. 3C, 3E, and 3F: Semi-quantitative and SYBR® green-based RT-qPCR analyses of total MDM4, MDM4-FL and MDM4-S isoforms in cultured melanoma cells (FIG. 3C), in a series of short-term melanoma cultures (FIG. 3E) and melanoma clinical samples (FIG. 3F). GAPDH levels were used as loading control. Quantification of the PSI index is shown in the top panels. Immunoblotting analysis of expression levels of MDM4 is shown in the lower panels. Anti-TUBULIN and anti-ACTIN immunoblotting were used as loading controls. * indicates TP53 mutant melanoma lesions. FIG. 3D: Correlation plot between the PSI index and MDM4 protein abundance, normalized for the protein loading control, in melanoma cell lines.

FIG. 5A: Binding sites from the SRSF1, SRSF2, SRSF3 and SRSF4 mouse CLIP-Seq data in the surrounding of Mdm4 exon 7 in mouse. Basewise conservation score (PhyloP) considering the placental-mammal subset (40 species) plotted below the binding sites. Close view of exon 7 and relative binding sites are shown in the lower part. FIG. 5B: SRSF3-activity correlates broadly with MDM4 protein expression in short-term cultured MM lines. Sequencing data of the MM lines was used to quantify the extent of SRSF3 activity through the inclusion of exon 4 on its own mRNA. With the exception of MM047, low SRSF3 activity (exon 4 exclusion depicted in red) correlates to low expression levels of MDM4, high SRSF3 activity (exon 4 inclusion depicted in green) correlates to high MDM4. FIG. 5C: Left panel, Western blot quantifying SRSF3 and MDM4 total protein levels in UACC62 cells transduced with empty vector (pMX), pMX-SRSF3 or pMX-SRSF3-myc-tag. Right panel, PSI MDM4 index in these cell lines (both pMX-SRSF3 and pMX-SRSF3-myc-tag over express SRSF3). PSI MDM4 index is quantified with TAQMAN® qPCR assays for three biological replicates. FIG. 5D: Agarose gel intensity quantification of the PSI MDM4 index of several melanoma cell lines treated with DMSO (control) or TG003 (100 µM) for 6 hours. FIG. 5E: Cell viability, measured using CELLTITER-GLO® assay, upon treatment of six melanoma cell lines with increasing TG003 concentrations. FIG. 5F: Cell viability, measured using MTS assay, upon TG003 (100 µM) and/or the BRAF inhibitor Vemurafenib (PLX4032, 1 µM) in five melanoma cell lines. FIG. 5G: TG003 (100 µM) inhibits inclusion of exon 6 of MDM4 and reduces proliferation in parental (M249) and Vemurafenib-resistant (M249R) melanoma cells treated with 100 µM TG003 (or DMSO) for 48 hours. PCR analysis of MDM4 mRNA confirms exon 6 skipping in cell lines regardless of BRAFi resistance status. FIG. 5H: TG003 treatment for 72 hours resulted in the loss of proliferation in cell lines regardless of BRAFi resistance status, as measured by CELLTITER-GLO®. TG003 treatment sensitizes M249, but not M249R, to Vemurafenib treatment. FIG. 5I: p53-targets (p21, MDM2, BCC3, BAX and APAF) are equally activated following TG003 treatment in parental (M249) and Vemurafenib-resistant (M249R) melanoma cells.

FIG. 6A: PSI MDM4 index relative to non-targeting shRNA (Scramble) calculated upon SR proteins shRNA knock-down in A375 human melanoma cells. Each bar represents a single shRNA targeting the indicated SRSF family member (including two independent Scramble controls; details in Table 4). The experiment was performed in three biological replicates and the qPCR ran in two technical replicates. FIG. 6B: Binding sites from the SRSF3 mouse CLIP-Seq data were blotted to the human genome. RNA immunoprecipitation (RIP) Primers were designed to enrich for a negative control upstream region (yellow) and for the SRSF3 binding region (green). RNA immunoprecipitation (RIP) was performed on A375 cells (right panel). SRSF3 exon 4 was taken as positive control (blue). FIG. 6C: PSI MDM4 indexes and MDM4 protein levels (Western blot-bottom) are evaluated following SRSF3 KD with five independent shRNAs. A scramble shRNA (Scr) is used as control. FIG. 6D: RT-qPCR quantification of total MDM4, SRSF3 and p53-transcriptional targets (MDM2, p21 and BBC3) following SRSF3 KD with five independent shRNAs. A scramble shRNA (Scr) is used as a reference/control. FIG. 6E: Quantification of cell viability (top panel) and apoptosis (bottom panel) upon SRSF3 KD using two independent shRNAs (171 and 227) in A375 cells (see also Table 4).

FIG. 7A: Semi-quantitative RT-PCR analysis of total MDM4-FL and MDM4-S isoforms (and GAPDH as control) in the A375 melanoma cells transfected with MDM4-targeting (ASO MDM4) and scramble (Scr) control ASOs. Immunoblotting analysis of expression levels of MDM4, p53 and of the two well-established p53-targets MDM2 and p21 is shown in the lower panels. Anti-TUBULIN immunoblotting was used to detect differences in sample loading. FIG. 7B: Short-term cultures were transfected with MDM4-targeting and scramble (Scr) control ASOs and colony formation was evaluated using low-density colony formation assays ten days after seeding. For the quantification of the colony formation assays, the data are presented as the mean % of area occupancy of multiple different biological replicates (±SD). Immunoblotting analysis of expression levels of MDM4 is shown in the lower panel. Anti-ACTIN immunoblotting was used to detect differences in sample loading. Right panel shows SYBR® green-based RT-qPCR analysis of the PSI MDM4 index after transfection with ASOs. * indicates TP53 mutant melanoma lesions. FIGS. 7C-7H: Cohorts of patient-derived xenograft models of melanoma (MEL002 and MEL010) were established. When tumors reached an average volume of 100 mm$^3$ (Me1002) or 150 mm$^2$ (Me1010), cohorts were treated with the vivo MDM4 morpholino (or Scr control) upon intra-tumor (MEL002 IT) or intravenous tail vein (MEL010 IV) injections every two days. Tumor development of MEL002 (FIG. 7C) and MEL010 (FIG. 7G) was monitored by caliper measurement for the indicated period. Data represent the mean (±SEM) of the different biological replicates. FIG. 7D: ASO-mediated exon 6 skipping decreases MDM4 protein abundance in MEL002 lesions. Semi-quantitative analysis of MDM4-FL and MDM4-S isoforms in 12 dissected melanoma lesions exposed to the MDM4-targeting or scramble (Scr) control ASOs. SYBR® green-based RT-qPCR of the PSI index in the various samples is shown in the top panel. Immunoblotting analysis of expression levels of MDM4 is shown in the lower panel. Anti-ACTIN immunoblotting was used to detect differences in sample loading. Reduction of MDM4 protein levels was confirmed through IHC staining on lesions exposed to the MDM4-targeting and scramble (Scr) control ASO for MEL002 (FIG. 7E) and MEL010 (FIG. 7H). IHC for apoptotic marker Cleaved CASPASE-3 and the proliferative marker KI67 in melanoma lesions exposed to the MDM4-targeting and scramble (Scr) control ASOs for MEL002 (FIG. 7E) and MEL010 (FIG. 7H). Scale bar: 100 μm. FIG. 7F: Quantification of the images represented in panel 4 (FIG. 7E). Tumors from two different mice (n=2) were analyzed for each cohort.

FIG. 8A: Short-term melanoma cultures were transfected with MDM4-targeting ASO and scramble (Scr) control at day 0. At days 3, 6 and 8, the cells were collected and a semi-quantitative RT-PCR on MDM4 exon 6 was performed to visualize the abundance of MDM4-S isoform over time. Culturing medium was changed regularly every two days. FIG. 8B: Short-term cultures were transfected with MDM4-targeting and scramble (Scr) control ASOs and colony formation was evaluated using low-density colony formation assays ten days after seeding. For the quantification of the colony formation assays, the data are presented as the mean number of colonies counted for multiple different biological replicates (±SD). Each graph is accompanied by a representative picture of the assay. FIG. 8C: PSI MDM4 index in A375 cells transfected with a panel of 2'-O-Methyl antisense oligonucleotides (ASO) and morpholino. For each group, a type-specific scrambled sequence is used as a control. Genomic location of each ASO as well as the predicted SRSF3 binding site is indicated in the left panel. FIG. 8D: qPCR analysis of genes regulated by p53 in PDX Me1002. ASO MDM4-treatment upregulates MDM2 and p21 but downregulates KIF23, CENPF and MAD2L1. Statistical significance was determined with the Mann-Whitney test.

FIG. 9A: A BRAFV600E-positive short-term culture (MM034) was transfected with MDM4-targeting and scramble (Scr) control ASOs and colony formation was evaluated using low-density colony formation assays ten days after seeding and exposure to 25 nM of the BRAFV600E-inhibitor PLX4032. Quantification of the colony formation assays is shown on the right panel, the data are presented as the % of area occupancy. FIGS. 9B-9D: Cohorts of patient-derived xenograft model of melanoma (MEL006) were established. When tumors reached an average volume of 200 mm$^3$, they were subdivided in cohorts for various combinatorial treatments. The mice were gavaged with Dabrafenib or vehicle every day and injected intratumorally with Scr ASO or MDM4 ASO every other day. FIG. 9B: Tumor development was monitored by caliper measurement for the indicated period. Data represent the mean (±SEM) of the indicated biological replicates. The red dotted line indicates the average starting volume of the tumors in the MDM4 ASO+BRAFi cohort. FIG. 9C: IHC for MDM4, the apoptotic marker Cleaved CASPASE-3 and the proliferative marker KI67 in melanoma lesions exposed to the combination treatment of ASO-based exon 6-skipping with BRAFi. Scale bar: 100 μm. FIG. 9D: Quantification of the images represented in panel 5 of FIG. 9C. Quantification of the stained samples was automatically generated with ImageJ. For each tumor, three slides were stained and counted. Both cohorts contained four different tumors each (n=12 counted slides). FIG. 9E: PDX model MEL006 was treated with BRAFi alone (n=1), BRAFi+Scr ASO (n=1) or BRAFi+MDM4 ASO (n=2).

FIG. 10A: The PSI MDM4 index was calculated, similarly to what is described in FIG. 2B, for Breast carcinoma (BRCA), Ovarian Serous Cystadenocarcinoma (OV) and Lymphoid Neoplasm Diffuse Large B-cell Lymphoma (DLBCL). For each tumor type, all values were sorted and plotted. The red area indicates the tumor specimens with PSI MDM4>0.4; the total percentage of tumor samples in this area is indicated in the top left corner. FIG. 10B: ASO-mediated exon 6 skipping reduces in vitro colony formation of various cancer types. MCF-7 breast cancer, SK-N-SH neuroblastoma and Tov21G ovarian cancer cell lines were transfected with MDM4-targeting and scramble (Scr) control ASOs and colony formation was evaluated using low-density colony formation assays ten days after seeding. Quantification of the colony formation assays, the data are presented as the mean % of area occupancy of multiple different biological replicates (±SD). Immunoblotting analysis of expression levels of MDM4 protein is shown below. FIG. 10C: Left panel, cell titer analysis of a clinical sample of diffuse large B-cell lymphoma (BCL13) three days after transfection with MDM4-targeting and Scr ASO. Right panel, semi-quantitative RT-PCR analysis of MDM4 splicing. FIGS. 10D-10F: Cohorts of patient-derived xenograft model of DLBCL (BCL13) were established. When tumors reached an average volume of 150-250 mm$^3$ (BCL13), cohorts were treated with the vivo MDM4 ASO (or Scr control) upon intra-tumor (BCL13 IT) injections every two days. Tumor size of BCL13 was assessed at 20 days. Data represent the mean (±SEM) of the different biological replicates. FIG. 10E: ASO-mediated exon 6 skipping decreases PSI MDM4 index and MDM4 protein abundance in BCL13 tumors. Semi-quantitative analysis of MDM4-FL and MDM4-S isoforms in ten dissected DLBCL tumors exposed to the MDM4-targeting or scramble (Scr) control ASOs. Immunoblotting analysis of expression levels of MDM4 is shown in the lower panel. Anti-ACTIN immunoblotting was used to detect differences in sample loading. FIG. 10F: IHC for apoptotic marker Cleaved CASPASE-3 and the proliferative marker KI67 in DLBCL lesions exposed to the MDM4-targeting and scramble (Scr) control. Right panels, quantification of the images represented in panel 6 of FIG. 10F. Tumors from three different mice (n=3) were analyzed for each cohort. Scale bars: 100 μm.

DETAILED DESCRIPTION

Definitions

Figure 1C:
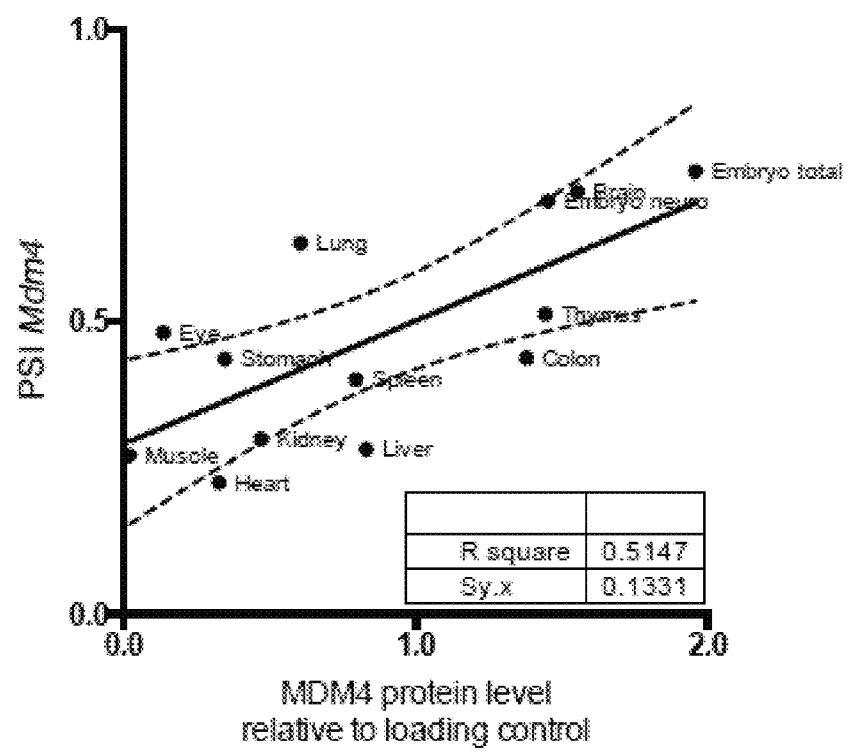

This disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual, 2$^{nd}$* ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

As used herein, "MDM4" refers to the MDM4 gene (Gene ID: 4194 in humans), also known as HDMX, MDMX or MRP1, or protein encoded thereby. The gene encodes a nuclear protein that contains a p53 binding domain at the N-terminus and a RING finger domain at the C-terminus, and shows structural similarity to p53-binding protein MDM2. Both proteins bind the p53 tumor suppressor protein and inhibit its activity, and have been shown to be overexpressed in a variety of human cancers. However, unlike MDM2 which degrades p53, this protein inhibits p53 by binding its transcriptional activation domain. This protein also interacts with MDM2 protein via the RING finger domain, and inhibits the latter's degradation. So this protein can reverse MDM2-targeted degradation of p53, while maintaining suppression of p53 transactivation and apoptotic functions. Alternatively spliced transcript variants encoding different isoforms have been noted for this gene. Among these transcript variants, the most important ones are isoform 1, the full-length transcript, designated as MDM4-FL (full-length), containing ten exons in the transcript (ENST00000367182, length 10073 bp), and isoform 4, also designated as MDM4s (ENST00000471783, length 552 bp). Human MDM4-S is the product of an internal deletion of 68 base pairs, occurring at the level of exon 6. This deletion produces a shift of the reading frame after codon 114 and introduces a new translation stop codon following amino acid 140. The result of this splicing is a truncated protein that encodes for the first 114 aa of full-length MDM4 (the entire p53 binding domain) with the addition of C-terminal 26 aa residues (13 in the murine protein). For a graphical overview of these transcripts, see FIG. 2 of Mancini et al., 2009.

As shown in the Examples, the regulation of a single alternative splicing event determines the levels of MDM4 protein expression in metastatic melanoma (MM). While high MDM4 levels require Exon 6 inclusion, alternative splicing of Exon 6, which generates the unstable MDM4s isoform, occurs in most normal adult tissues and in MM expressing low levels of MDM4. Importantly, the ratio between MDM4 full-length and MDM4 short-length transcripts, which can be easily determined in a single RT-PCR assay, predicts very accurately MDM4 protein levels and could, therefore, be used to identify high MDM4-expressor patients. These would be particularly sensitive to MDM4 inhibition therapy.

This role of MDM4s is particularly surprising, as Rallapalli et al. (Rallapalli et al., 1999) had identified this truncated isoform as a strong inhibitor of p53. This is likely due to an overexpression artefact. As shown here, MDM4s protein is actually not expressed/made: as the MDM4s-transcript is swiftly degraded and/or the MDM4s protein is exquisitely unstable in vivo. Thus, there is a discrepancy between MDM4 total RNA levels (which includes both FL and S isoforms) and MDM4 protein levels.

SRSF3 was identified as the main regulator of exon 6 inclusion. Consistent with this finding, SRSF3 is a known oncogene, able to transform primary cells, and to prevent senescence (Tang et al., 2013; Corbo et al., 2013).

Several strategies can be used to perturb the efficiency of the splicing machinery, alter the MDM4/MDM4s splicing ratio and reduced MDM4 protein in MM: KD of PRMT5, an upstream regulator of snRNP biogenesis (Bezzi et al., 2013) or SmB, a member of the Sm proteins and core component of all snRNPs (Saltzman et al., 2011); the small molecule inhibitor Meayamycin, which targets SF3B, a component of the U2 snRNP as well as TG003, which blocks SR protein phosphorylation (Muraki et al., 2004; Hagiwara et al., 2005). In addition, ASO-based strategies were designed to directly and specifically target the inclusion of MDM4 Exon 6. Importantly all these approaches result in growth inhibition and apoptosis of melanoma lines, and additionally to an increased sensitivity to chemotherapeutic agents and to a BRAF inhibitor. Based on these data, the development of an ASO-based method is proposed that promotes MDM4 Exon 6 skipping as a novel targeted therapeutic strategies allowing re-activation of p53 tumor killing activities in melanoma and by extension in other tumor types expressing high levels of MDM4 (or high ratios of MDM4 full-length transcript over MDM4s transcript).

It is an object of the disclosure to provide direct and selective inhibitors of MDM4 for use in treatment of cancer. With direct, it is meant that MDM4 is directly targeted, so the inhibitors are not solely interaction inhibitors of MDM4-p53. This is important to inhibit p53-independent oncogenic functions of MDM4. With selective, it is meant that the inhibitors specifically inhibit MDM4, and do not inhibit MDM2, nor any other RING finger protein. This is important to prevent deleterious side effects (i.e., iatrogenic effects caused by the therapy) in normal tissues.

This is equivalent as saying that methods of treating cancer in a subject in need thereof are provided, comprising a step of administering a direct and selective inhibitor of MDM4 to said subject.

According to particular embodiments, the cancer has high levels of MDM4. More precisely, the cancer expresses more full-length MDM4 transcript (MDM4FL, which includes exon 6) than short MDM4 transcript (MDM4s, which does not include exon 6). In other words, the MDM4FL/MDM4s ratio is greater than one in said cancer. According to further embodiments, the ratio is higher than 2, higher than 3, higher than 4 or higher than 5.

Figure 4A:
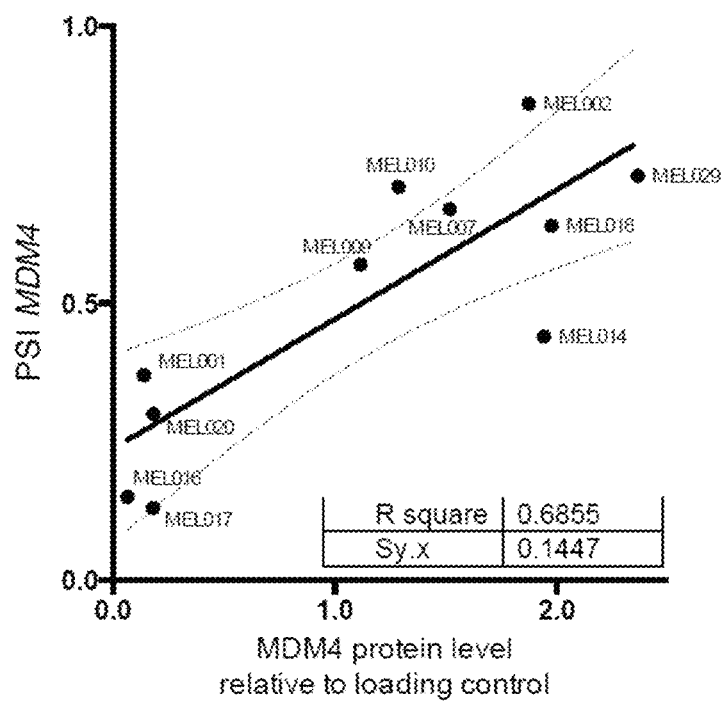
FIGS. 4A and 4B: Correlation plot between the PSI index and the MDM4 protein abundance, normalized for the protein loading control in (FIG. 4A) short-term melanoma cultures and (FIG. 4B) freshly isolated melanoma clinical samples.

According to particular embodiments, the cancer is selected from MDM4-overexpressing cancers as, e.g., described in references 9-12 (see particularly FIG. 4a of ref. 9; Table 2 of ref 10; Table 1 of ref. 11). These include stomach and small intestine cancers, glioblastomas, colorectal cancers, breast carcinomas, lung cancer, prostate cancer, osteosarcoma, retinoblastoma and melanoma. According to more particular embodiments, the cancer is selected from melanoma and breast cancer.

Although any direct and selective inhibitor of MDM4 can be suitable for the methods taught herein, it is particularly envisaged that the MDM4 inhibitor acts at the RNA level. More particularly, the inhibitor is an antisense oligonucleotide. Even more particularly envisaged is an antisense oligonucleotide that induces exon skipping. Most particularly, the exon that is skipped is exon 6.

Accordingly, also provided herein are MDM4 antisense oligonucleotides that induce exon skipping in the MDM4 transcript. Particularly, MDM4 antisense oligonucleotides that induce skipping of exon 6.

Such antisense oligonucleotides are also provided for use as a medicament. Particularly, they are provided for treatment of cancer (such as, e.g., breast cancer, melanoma, glioblastoma, retinoblastoma, or other cancers with a high MDM4 full-length/MDM4s ratio).

Alternatively, inhibitors of splicing machinery (e.g., Meayamycin, TG003, PRMT5 inhibitors, SmB inhibitors) can be administered to the tumor cells, thereby also inducing MDM4 exon skipping.

It is particularly envisaged that administration of the MDM4 inhibitor results in an increase in p53 activity. This can be measured, e.g., by increased expression of wt p53, increased activity of p53 itself, or upregulation of p53 targets.

Concomitantly, the inhibition of MDM4 results in an increased sensitivity to chemotherapeutic drugs and MAPK-targeting agents (as shown in the Examples section).

Accordingly, it is particularly envisaged that the inhibitor is used in a combination therapy with a chemotherapeutic or MAPK-targeting agent. The MDM4 inhibitor may be administered simultaneously with the other agent (e.g., chemotherapeutic), or before (or sometimes even after)—the important part is that they are administered within a time window so as to obtain a synergistic effect.

Well-known examples of MAPK-targeting agents include, but are not limited to, BRAF inhibitors such as Vemurafenib (RG7204 or PLX4032), GDC-0879, PLX-4720, Sorafenib (BAY 43-9006), dabrafenib, LGX818, BMS-908662, RAF265, XL281, R05185426, GSK2118436, TAK-632, MLN2480; MEK inhibitors such as trametinib (GSK1120212), Selumetinib, Binimetinib (MEK162), PD-325901, Cobimetinib (XL518), CI-1040, refametinib, pimasertib, AZD6244, AZD8330, R04987655, R05126766, WX-554, E6201, GDC-0623, U0126 and TAK-733; Ras inhibitors such as salirasib; and ERK inhibitors such as SCH772984, VTX11e, DEL-22379, PD98059.

Also provided herein are methods of identifying tumors suitable for treatment with a direct and selective inhibitor of MDM4, comprising:
  Determining whether expression of MDM4 RNA is increased in the tumor or a sample of tumor cells;
  Establishing whether the tumor is suitable for treatment, wherein increased expression is indicative of suitability for treatment.

Increased expression is typically compared versus a control, e.g., versus a non-tumor (non-transformed) sample of the same tissue or cells.

More particularly, the methods comprise the steps of:
  Determining the expression ratio of MDM4 full-length RNA transcript over the MDM4 transcript lacking exon 6 in the tumor or a sample of tumor cells;
  Establishing whether the tumor is suitable for treatment, wherein a higher ratio is indicative of suitability for treatment.

Particularly, the ratio should be higher than one. More particularly, the ratio should be higher than 2; higher than 3, higher than 4 or even higher than 5.

An exemplary method that can be used for determining the ratio of full-length versus short MDM4 transcript is shown in FIG. 1B, although other methods can be used as well.

According to particular embodiments, the cancer or tumor to be treated is a cancer wherein the TP53 gene is not mutated, i.e., a cancer with wild-type p53. (Please note that p53 may be inactivated, but is just not mutated.) According to particular embodiments, the cancer has high levels of MDM4. More precisely, the cancer expresses more full-length MDM4 transcript (MDM4FL, which includes exon 6) than short MDM4 transcript (MDM4s, which does not include exon 6). In other words, the MDM4FL/MDM4s ratio is greater than one in said cancer.

According to particular embodiments, the cancer is selected from the group of breast cancer, melanoma, glioblastoma and retinoblastoma. According to more particular embodiments, the cancer is melanoma.

The methods may optionally comprise a further step of administering a direct and selective inhibitor of MDM4 to the subject in which the tumor is present, particularly in those instances where the therapy would be suitable.

It is to be understood that although particular embodiments, specific configurations as well as materials and/or molecules, have been discussed herein for cells and methods according to this disclosure, various changes or modifications in form and detail may be made without departing from the scope and spirit of this disclosure. The following examples are provided to better illustrate particular embodiments, and they should not be considered limiting the application. The application is limited only by the claims.

Examples

Herein, it is shown that MDM4 abundance in melanoma strictly depends on the extent of exon 6 inclusion and identifies the SRSF3 oncoprotein as a key regulator of this splicing event. MDM4 exon 6 skipping can be induced by compromising the splicing machinery genetically or pharmacologically or, more specifically, using antisense oligonucleotides (ASOs). This leads to reduced MDM4 protein levels, activation of p53, growth inhibition and enhanced sensitivity of melanoma cells to chemotherapeutics and BRAF inhibitors. Regulation of MDM4 alternative splicing is, therefore, a key determinant of MDM4 abundance, and thereby of p53 activity, in melanoma (or human cancer). Targeting this splicing event allows inhibition of both p53-dependent and independent MDM4 oncogenic functions, is amenable to the clinic and can be used to treat a wide-range of MDM4-expressing cancers.

Example 1. MDM4 Splicing and Expression in Normal Tissues and Cancer 1.1 MDM4 Protein Abundance is Controlled by a Specific Alternative Splicing Switch The absence of direct correlation between total MDM4 mRNA levels and protein abundance in human melanoma (13) indicates that the post-transcriptional mechanism(s) are likely to contribute to MDM4 upregulation in cancers. Alternative splicing is one mechanism that modulates gene expression by adding or removing protein domains, affecting protein activity, or altering the stability of the mRNA transcripts (22, 23). In silico analysis of RNA-seq datasets (TGCA) from Skin Cutaneous Melanoma (SKCM) detected two MDM4 isoforms in addition to the full-length, of which MDM4-S was the most abundant (data not shown). MDM4-S (also known as HDMX-s) is an evolutionarily conserved splicing variant resulting from exclusion of exon 6 (25). Although the MDM4-S transcript is expected to produce a truncated protein there is no conclusive evidence supporting expression of such protein in cancer cells (45). Consistently, it has been previously reported that MDM4-S mRNA is targeted by the Non-Sense-Mediated Decay pathway, due to a premature stop codon in exon 7 (26). Importantly, an increase in the MDM4-S/MDM4-FL ratio associates primarily with reduced levels of full-length MDM4 protein (26, 45). Moreover, heterozygous mice engineered for an obligatory Mdm4 exon 6 skipping exhibited a decrease in Mdm4-FL protein expression and a concomitant increase in p53 activity (27). In light of these data, it is hypothesized that the MDM4-FL/MDM4-S ratio may be a better indicator/predictor of MDM4 protein abundance than total mRNA levels. It was previously reported that MDM4 protein levels are elevated in about 65% of human melanoma (13). Consistent with this hypothesis, expression of the MDM4-FL is 50% higher than MDM4-S in 66% of SKCM from the TCGA cohort (see section 1.3).

1.2 Mdm4 is Unproductively Spliced in Most Normal Adult Tissues and in Differentiated ES Cells To test whether AS contributes to the regulation of Mdm4 protein abundance in physiological conditions, the extent of exon 7 inclusion (corresponding to exon 6 in human) was measured in embryonic and various normal mouse adult tissues. In order to accurately do so, RTqPCR-based methods were developed, which are illustrated in FIGS. 1A and 1B. As expected, whereas the MDM4 protein is detectable in embryonic tissues, it is undetectable in most adult tissues, except brain, thymus and colon (2). Remarkably, this decrease in MDM4 protein expression was accompanied by a reduced Percent Spliced In (PSI), defined as the percentage of full-length Mdm4 mRNA (Mdm4-FL) over the total of all isoforms [Mdm4-FL/(Mdm4-FL+Mdm4-S)] (FIG. 2A and FIG. 1C). Thus, compared to embryonic tissues there is a clear decrease in MDM4 protein levels in most normal adult tissues and this decrease is, by and large, associated with a concomitant increase in Mdm4-S expression. These data indicate that low levels of MDM4 expression in most adult tissues are a consequence of inefficient exon 7 inclusion. Note that this correlation is not perfect; indeed, although the PSI index is relatively high in liver, the MDM4 protein is not detectable. This observation indicates that, in a minority of cases, other post-transcriptional (mRNA stability, export or translation rates) or post-translational events may also contribute to the regulation of MDM4 protein abundance. In addition, the predictive value of the PSI index is especially limited in normal tissues because of the extensive degradation of the Mdm4-S isoform by the NMD machinery (26).

MDM4 protein is highly expressed in mouse Embryonic Stem cells (mES cells) and its expression drastically declines upon exposure to the differentiation promoting agent retinoic acid (RA) (8). The mechanism underlying this decrease has not been elucidated. Interestingly, it was found that whereas total Mdm4 mRNA levels remained, by and large, unaffected, the PSI index paralleled the decrease in MDM4 protein levels induced by the RA treatment (FIG. 2B and data not shown). These data indicate that the MDM4 protein levels are also under the control of a switch in exon 7 splicing under these experimental conditions.

1.3 Enhanced Exon 6 Inclusion Leads to MDM4 Expression in Human Melanoma

Figure 3A:
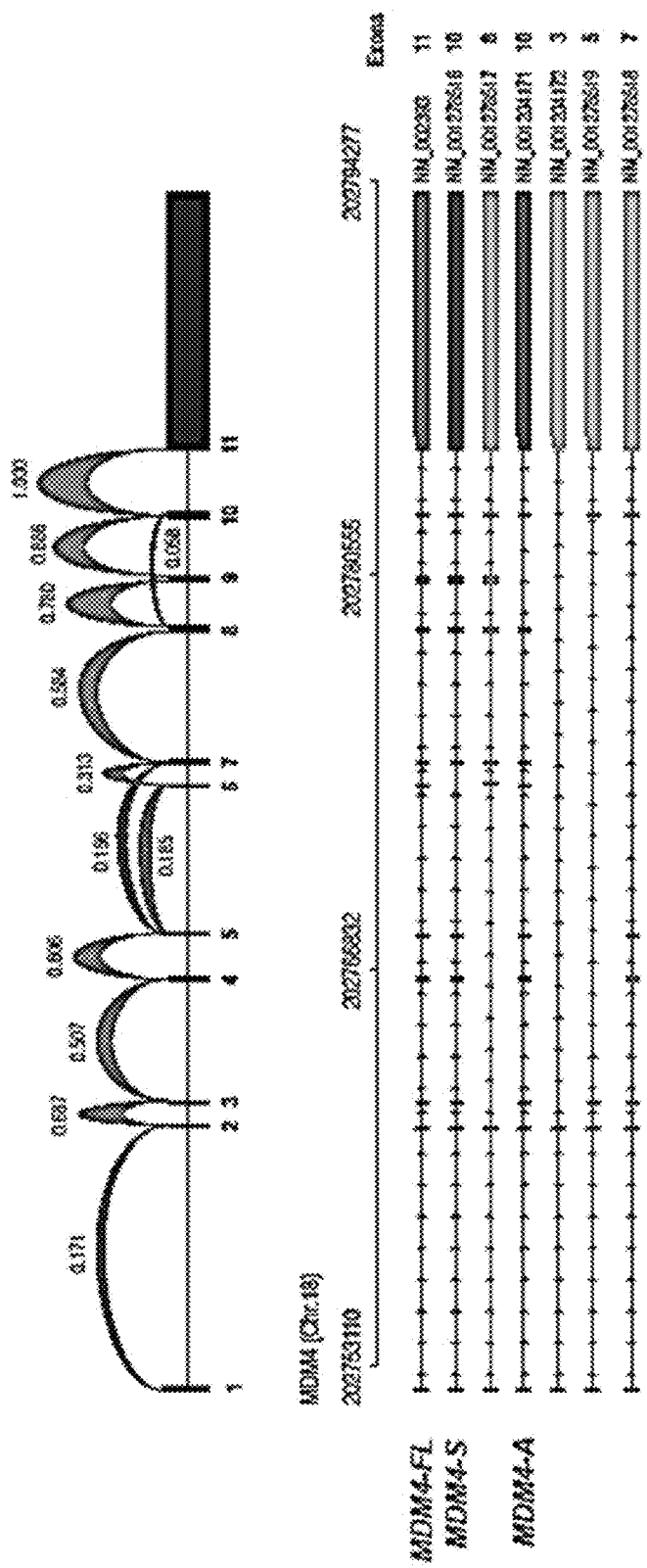
FIGS. 3A-3F: Enhanced exon 6 inclusion leads to MDM4 expression in human melanoma.
Figure 3B:
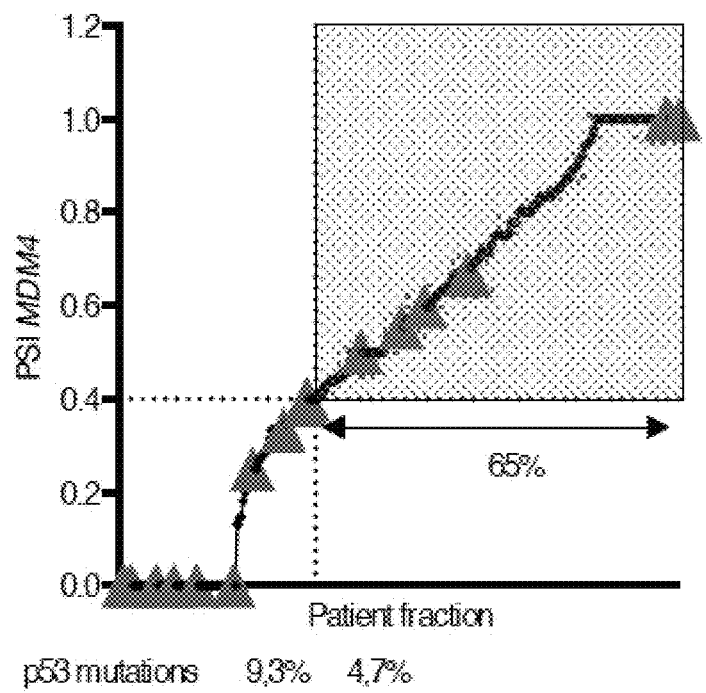
Figure 3C:
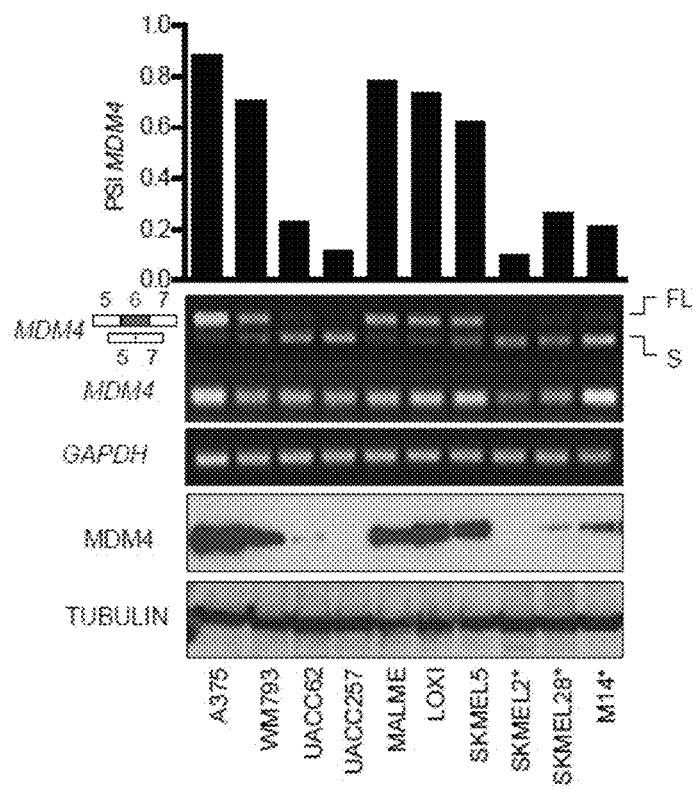
Figure 3D:
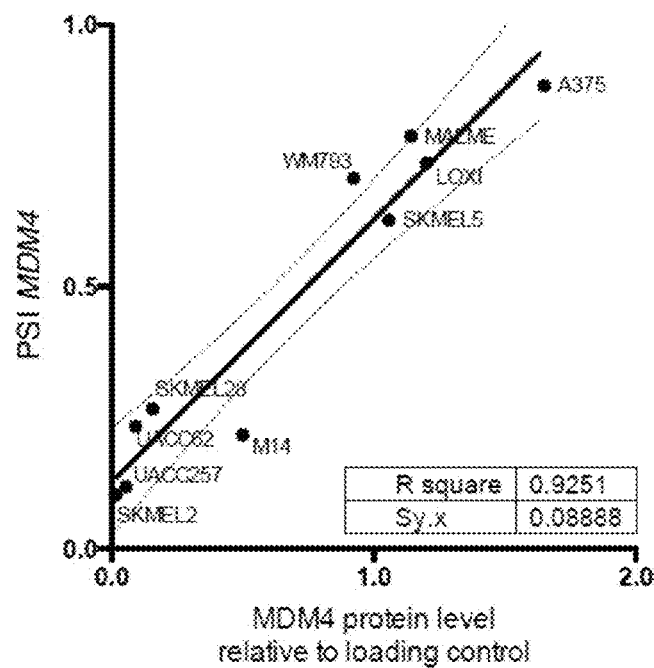
Figure 3E:
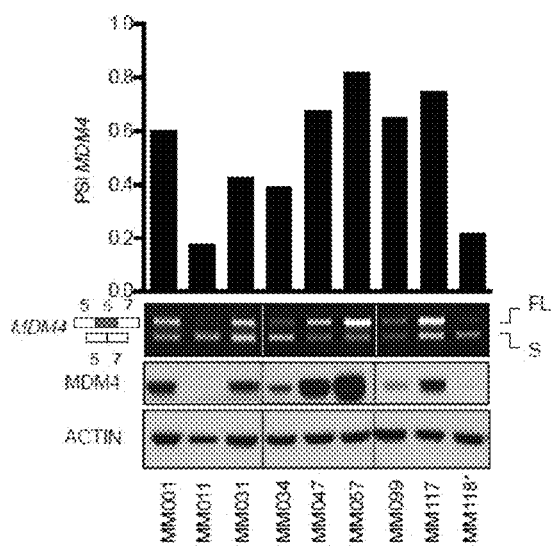
Figure 3F:
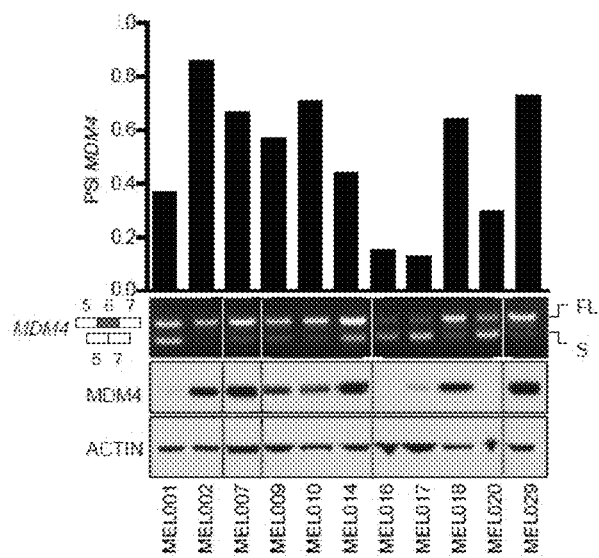
Figure 4B:
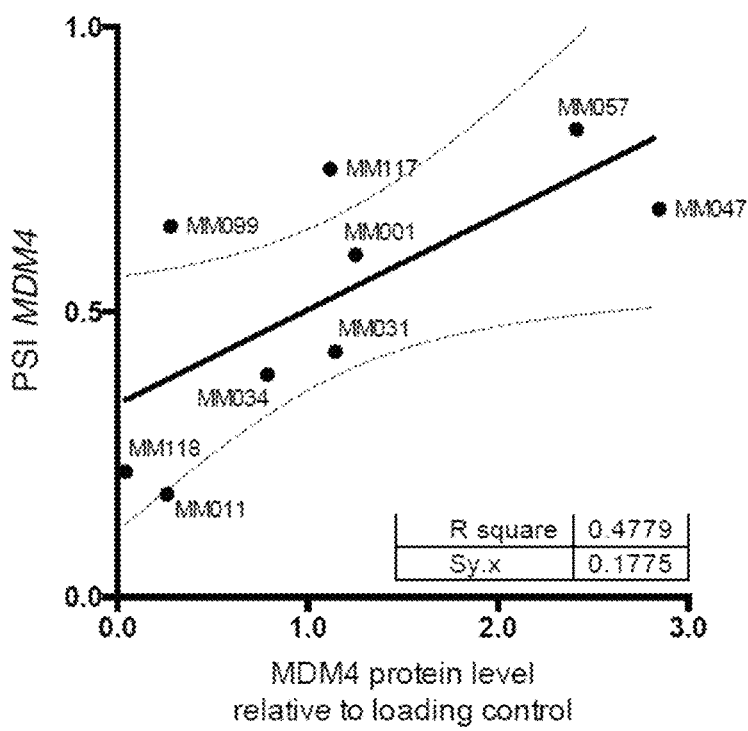

Next, it was reasoned that high levels of MDM4 protein expression in cancer cells may be due, at least partly, to their ability to revert the balance between skipping and inclusion of exon 6. Consistently, in silico analysis of RNA-seq data from SKin Cutaneous Melanoma samples (SKCM; TCGA) provides evidence that the full-length and protein-coding transcript is produced in the majority of these samples. Two additional MDM4 isoforms are also detected, among which MDM4-S is by far the most abundant (FIG. 3A). Previous data indicates that ~65% of cutaneous melanoma express high MDM4 protein levels (13). Given that 65% of the TCGA melanoma cohort (for which RNAseq data are available) exhibit a PSI index >0.4, this value was set as the cutoff point dividing samples into MDM4-expressers and nonexpressers (FIG. 3B). Notably, the frequency of p53-inactivating missense mutations (28) is lower in samples predicted to express MDM4 (4.6%) than in the nonexpressers (9.3%) This is consistent with the previous observations that a low PSI index is associated with inactivating p53 mutations or MDM2 overexpression (29). However, this also indicates the presence in some cancers of p53-inactivating mutations in MDM4-expressing samples, an observation that is consistent with p53-independent oncogenic functions of MDM4. Next, the extent of exon 6 inclusion in several human melanoma cell lines was measured (FIG. 3C). In agreement with this prediction, melanoma cell lines (n=10) with a PSI index <0.4 expressed very low to undetectable levels of MDM4 (FIG. 3C). As expected, no correlation between total MDM4 mRNA levels and protein abundance was observed, while a striking correlation was observed between the PSI index and MDM4 protein abundance (FIGS. 3C and 3D). To further substantiate the above findings, the PSI index and protein abundance in short-term melanoma cultures and freshly isolated melanoma clinical samples were quantified (n=20; FIGS. 3E and 3F). Again a clear correlation between the PSI index and MDM4 protein levels was observed (FIGS. 4A and 4B). Moreover, in agreement with the above prediction, samples with PSI index <0.4 expressed very low to undetectable levels of MDM4 (FIGS. 3E and 3F).

Taken together, these data indicate that regulation of exon 6 inclusion is a critical determinant of mammalian MDM4 protein abundance, both in normal tissues and in tumor cells. This raises the intriguing possibility that alternative splicing is one key mechanism through which MDM4 is upregulated to buffer p53 in highly proliferative embryonic tissues and cancer cells. The data also indicate that the PSI index is a good predictor of MDM4 protein abundance in melanoma.

Example 2. SRSF3 is Required for Efficient Inclusion of MDM4 Exon 6

Figure 5A:
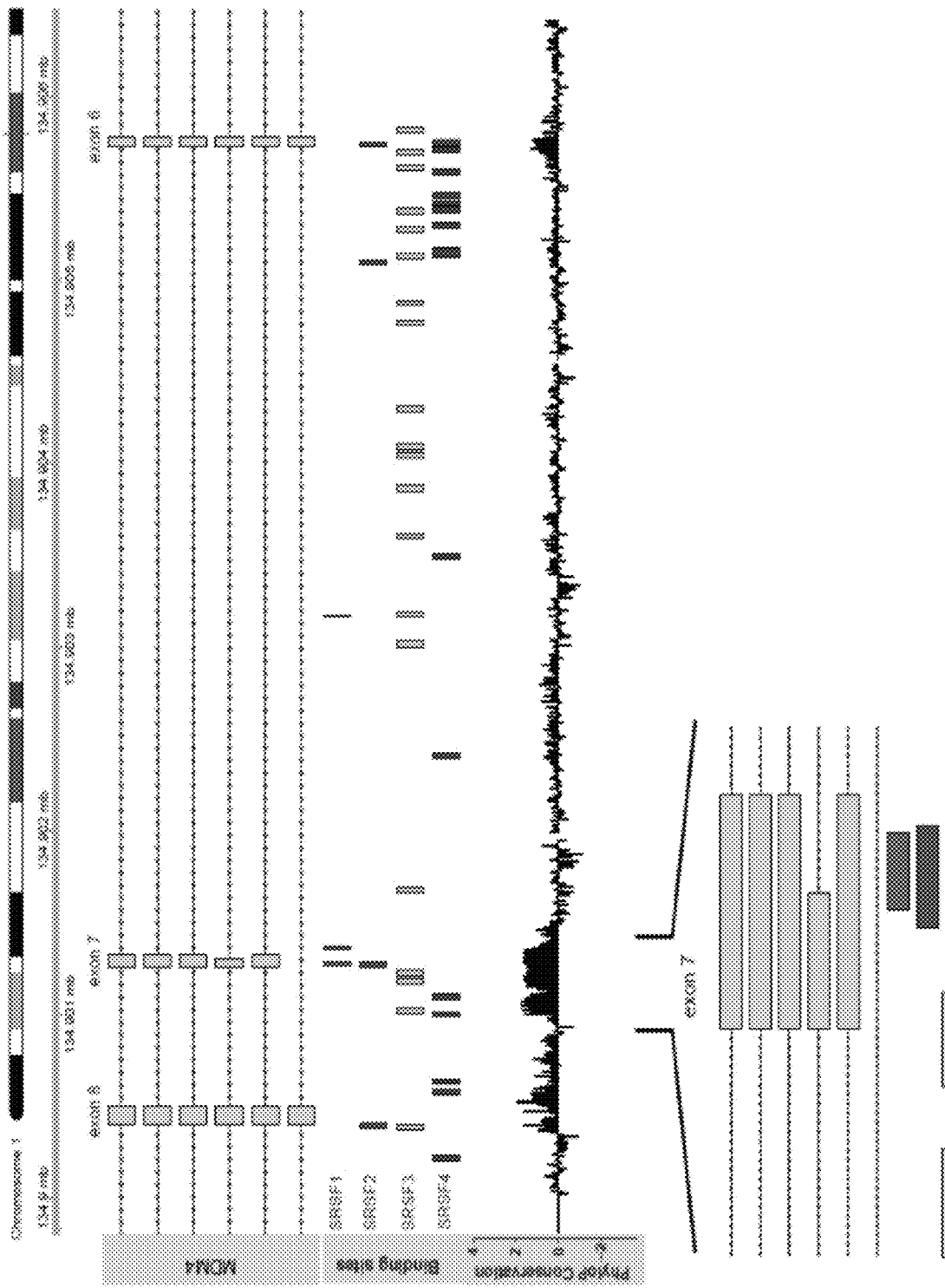
FIGS. 5A-5I.
Figure 6A:
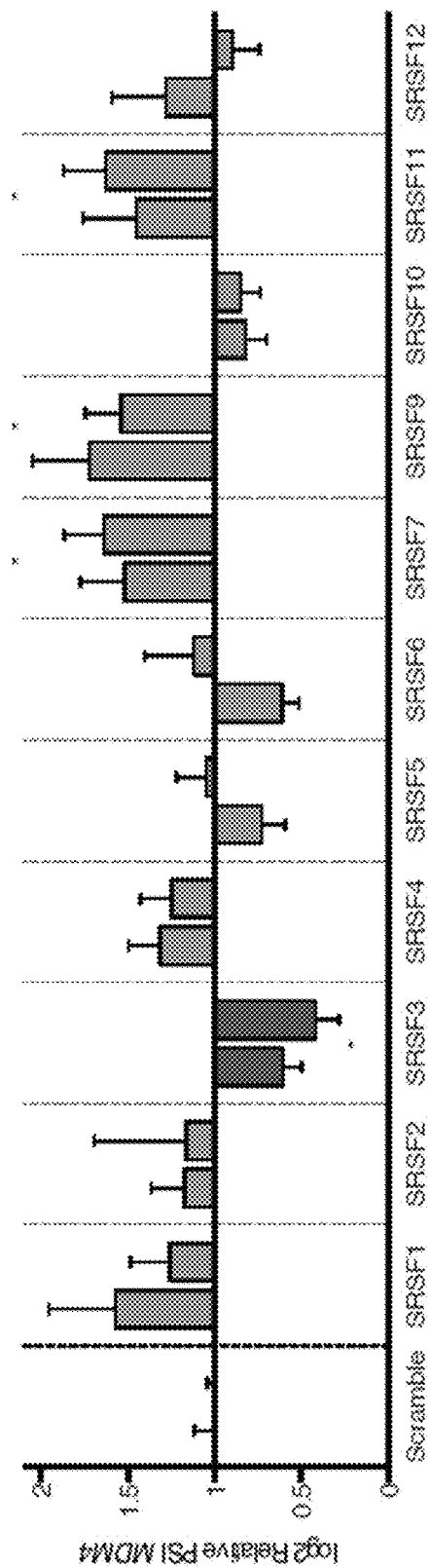
FIGS. 6A-6E: SRSF3 is required for efficient inclusion of MDM4 exon 6 and melanoma growth.

In order to identify regulators of MDM4 exon 6 splicing, available high-throughput sequencing of RNA isolated by cross-linking immunoprecipitation (HITS- and PAR-CLIP)-datasets were mined (30-35). Four members of the SR-family were identified as putative regulators of this splicing event in mouse cells (FIG. 5A). Since the genomic region surrounding human exon 6 is highly conserved in vertebrates (PyloP conservation plot in FIG. 5A), tests were performed to determine whether this family of splicing factors is modulating exon 6 inclusion in human cells. SRSF1-12 was depleted individually with short-hairpin RNAs (shRNAs) in A375 melanoma cells and quantified the PSI index (FIG. 6A). Strikingly, depletion of SRSF3 robustly induced MDM4 exon 6 skipping. In contrast, KD SRSF7, SRSF9 and SRSF11 unexpectedly increased the inclusion of exon 6. These data indicate that alternative splicing of MDM4 is highly regulated by multiple splicing factors, which is predicted to allow integration of multiple upstream regulatory signals.

Figure 5B:
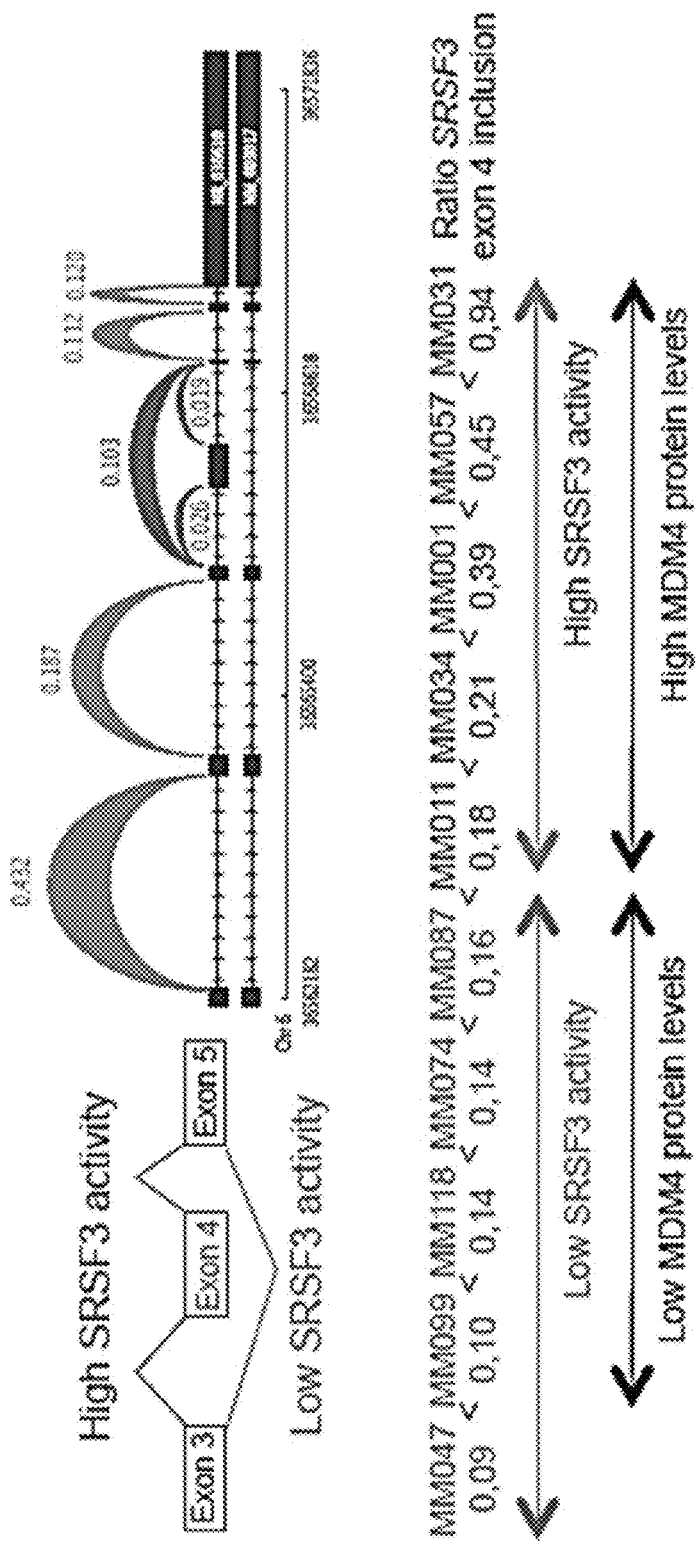

Consistent with its putative ability to promote MDM4 exon 6 inclusion, SRSF3 is a well-established oncogene (36). SRSF3 also auto-regulates its expression by modulating inclusion of its own exon 4 (30). As described above, a striking correlation between the PSI index and MDM4 protein abundance was observed in a series of short-term melanoma cultures (FIG. 3E). In keeping with SRSF3 being a modulator of MDM4 AS, high SRSF3 activity, determined by the extent of autoregulatory inclusion of exon 4, correlated with high MDM4 protein expression in these samples (FIG. 5B).

Splicing Inhibition Induces Mdm4 Exon 6 Skipping and Reduces Cell Proliferation in Melanoma Cell Lines The above data predict that drugs that compromise the splicing machinery should decrease the MDM4-FL/MDM4-S ratio and consequently reactivate p53 tumor suppressor function.

To this end, a KD of PRMT5 was performed, a methyltransferase regulating snRNP biogenesis and SmB/B', a core component of all major snRNPs (26). This led to MDM4 exon 6 skipping (data not shown), reduced MDM4 protein abundance (data not shown) and decreased viability in melanoma cells (data not shown). PRMT5 depletion selectively killed the A375 melanoma line and had no effect on the proliferation of normal melanocytes (data not shown).

Figure 6B:
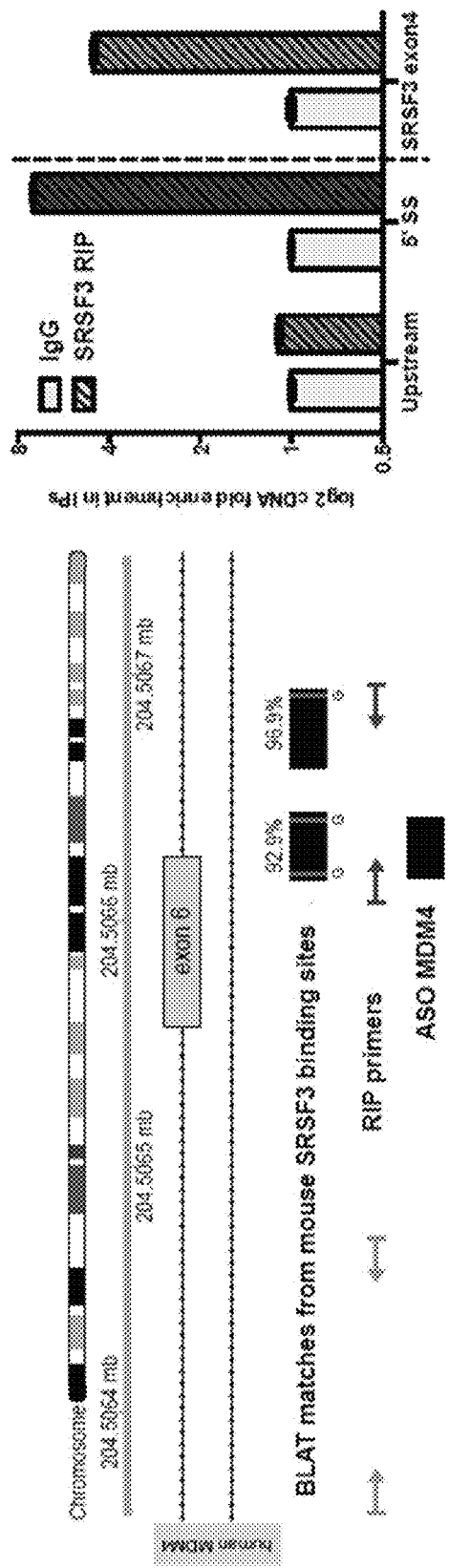
Figure 6C:
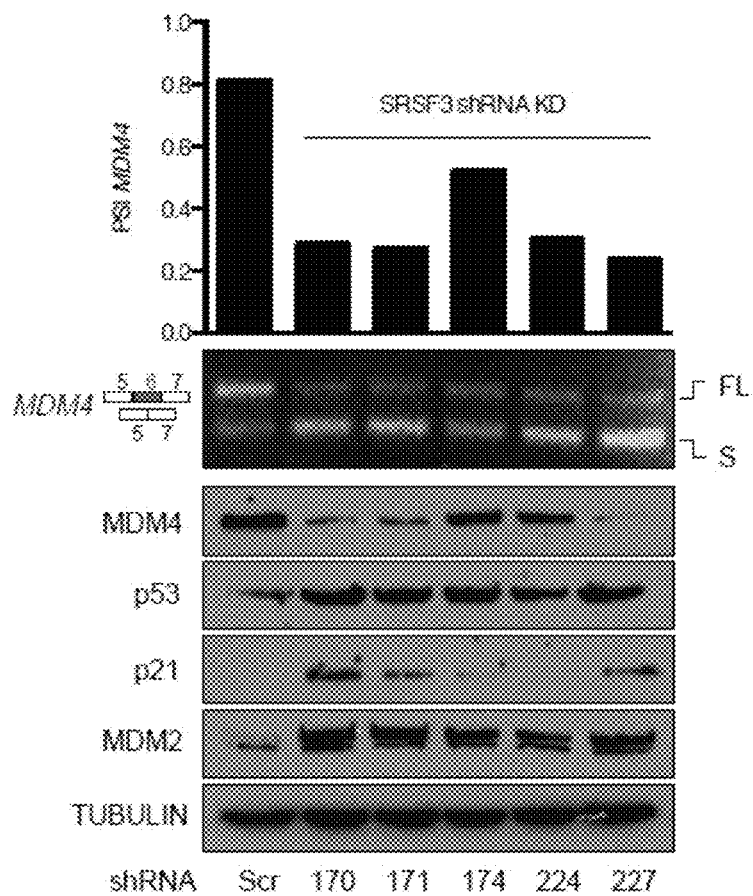
Figure 6D:
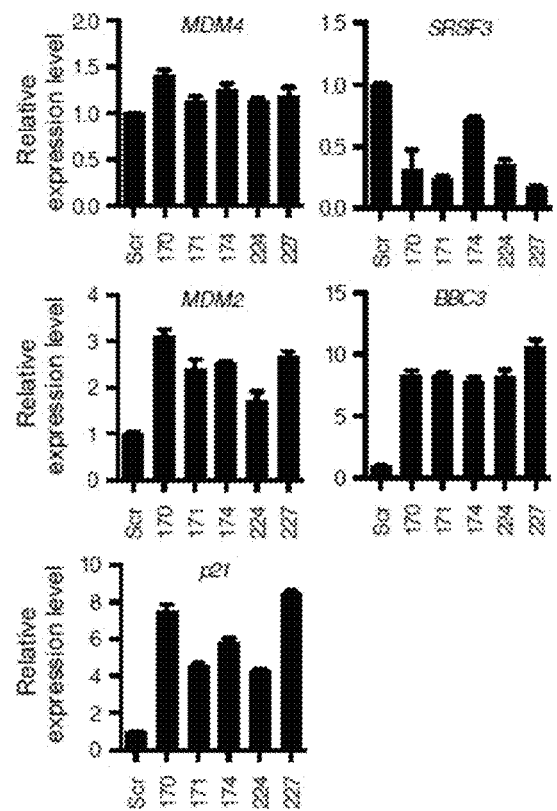
Figure 6E:
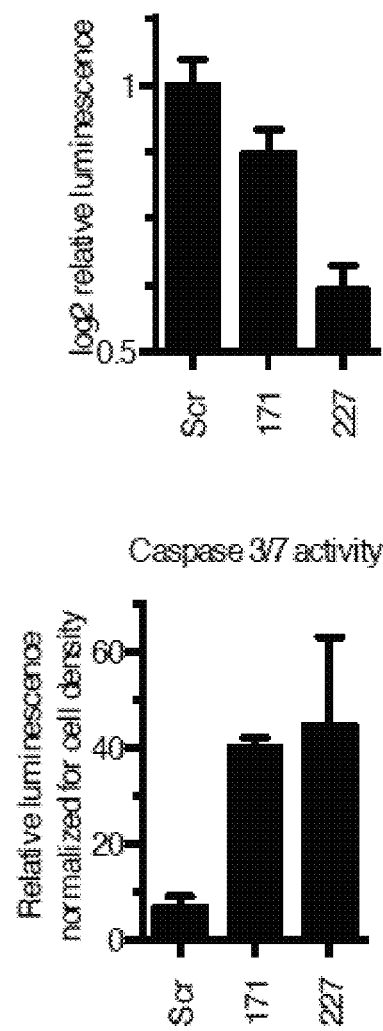

The direct binding of human SRSF3 to MDM4 was further validated by RNA immunoprecipitation (RIP)(30) (FIG. 6B) and critically demonstrated that SRSF3 silencing, using five independent shRNA hairpins, led to a significant decrease in exon 6 inclusion and a concomitant decrease in MDM4 protein levels (FIG. 6C). MDM4 down-regulation observed upon SRSF3 KD was accompanied by a robust activation of the p53 pathway as evidenced by an increase in expression of some of its well-established target genes, including p21, MDM2 and BBC3 (or PUMA), both at the mRNA and/or protein level (FIGS. 6C and 6D). A robust decrease in growth and induction of apoptotic cell death was also observed in the SRSF3 KD cells (FIG. 6E).

Figure 5C:
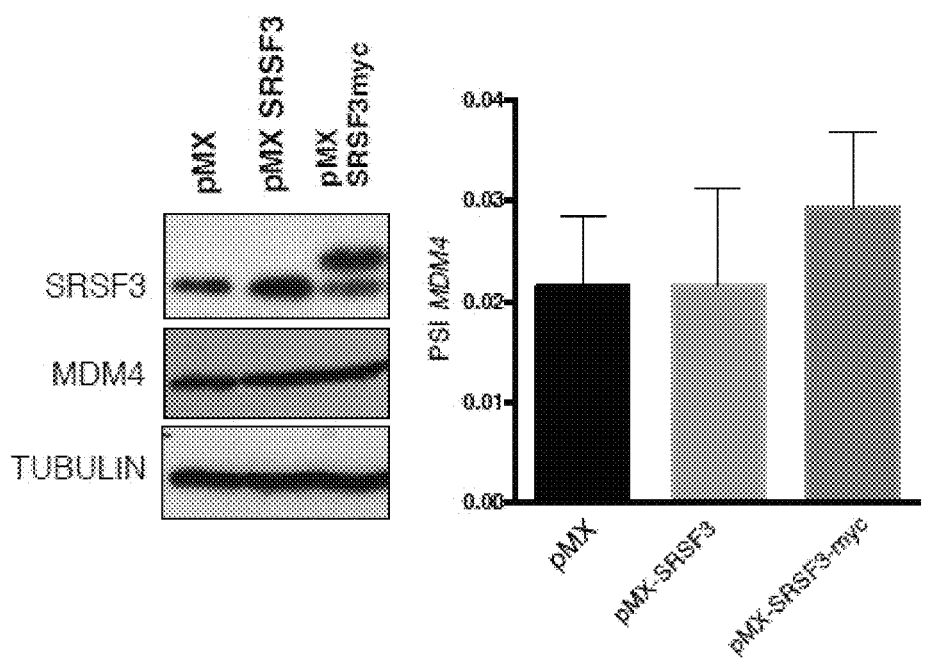

Notably, overexpression of SRSF3 alone was not sufficient to increase inclusion of exon 6 significantly (FIG. 5C). Additional splicing enhancers may, therefore, also contribute and/or assist SRSF3 in promoting inclusion of this exon.

Figure 5D:
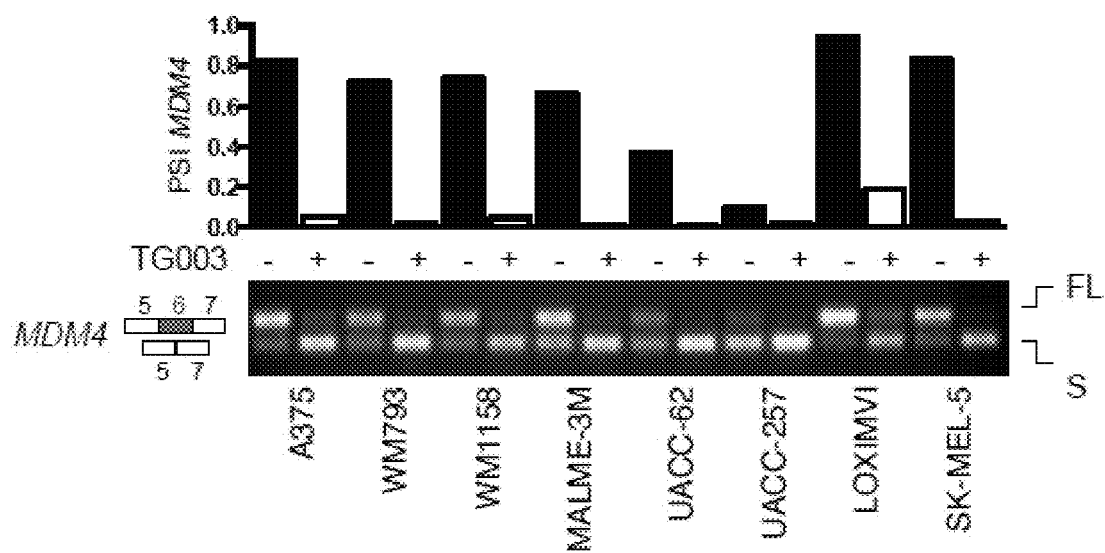
Figure 5E:
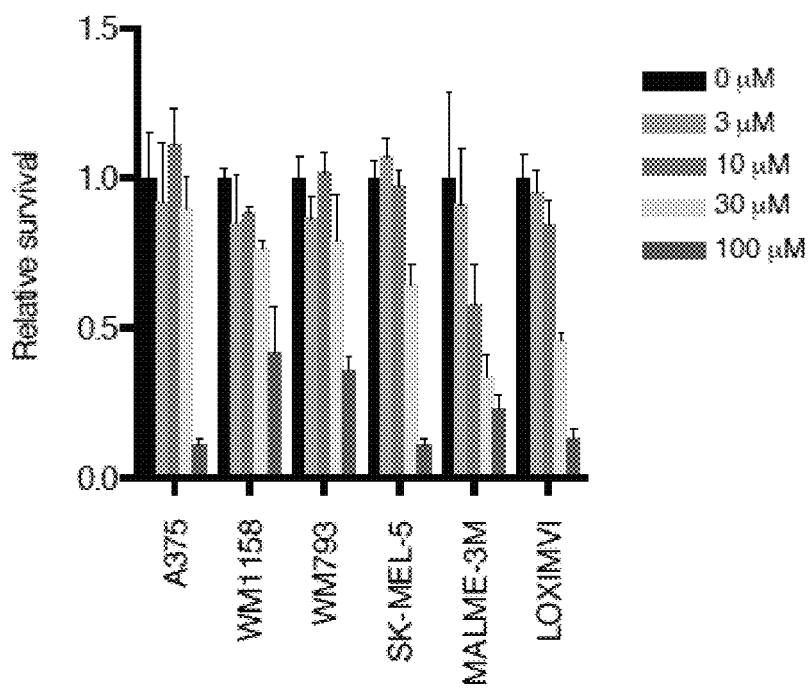
Figure 5F:
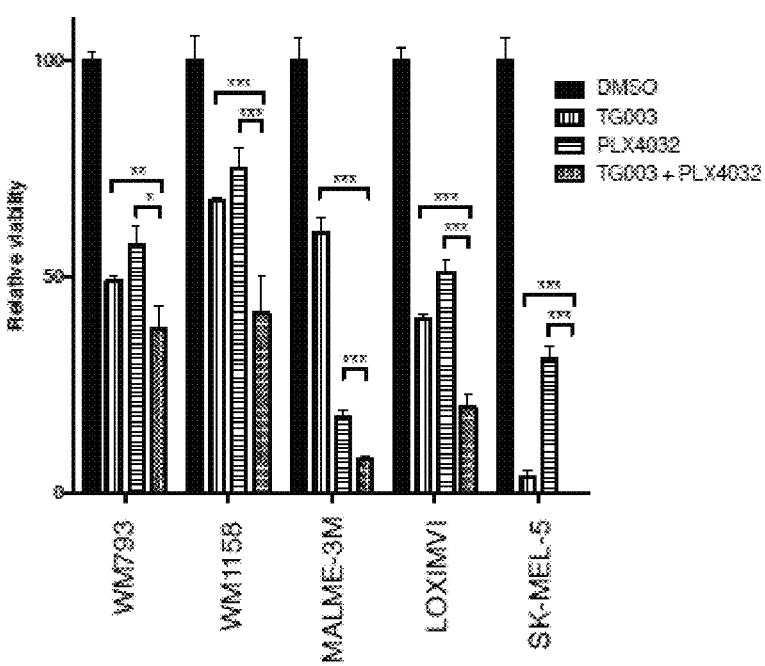
Figure 5G:
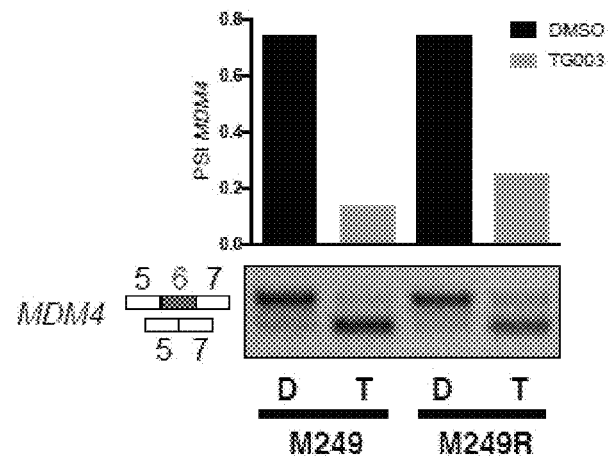
Figure 5H:
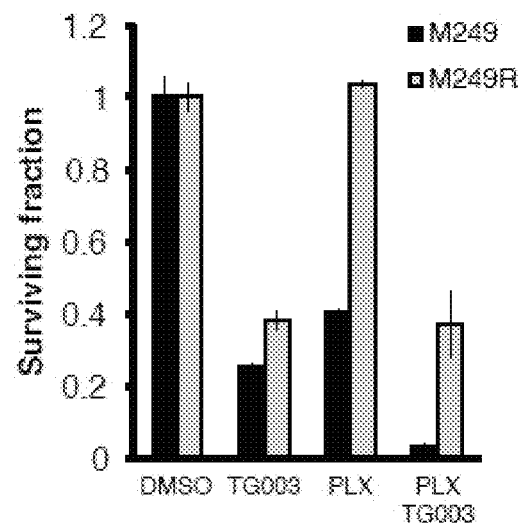
Figure 5I:
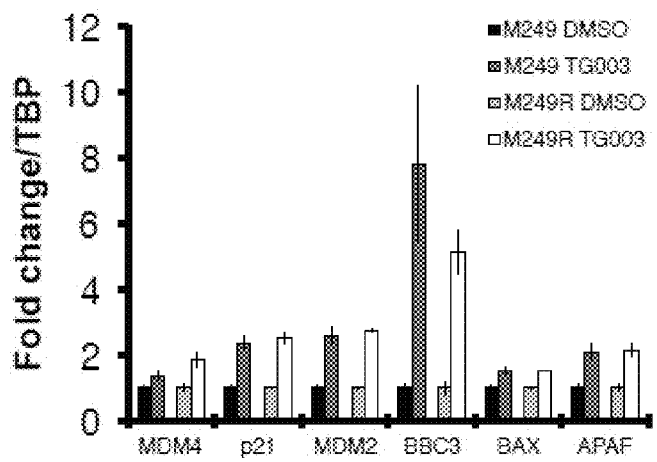

Nevertheless, the observation that SRSF3 silencing causes a decrease in exon 6 inclusion is consistent with the previous findings that inhibition of SR protein-kinases CLKs, by the small molecule TG003 (37), resulted in a similar decreased MDM4 protein abundance, both in mouse neural stem/progenitors and several other human cancer cell lines (26). In keeping with these findings TG003 led to similar effects in melanoma cell lines (FIG. 5D) and reduced their survival rates (FIG. 5E). Interestingly, TG003 sensitized BRAFV600E-mutant melanoma cells to the BRAFV600E-inhibitor vemurafenib (PLX4032) (FIG. 5F). Moreover, while TG003 reduced the PSI index (FIG. 5G) and cell survival (FIG. 5H), it induced concomitantly p53 transcriptional activity (FIG. 5I) both in vemurafenib-sensitive (M249) and resistant (M249R) cell lines (38). Thus, the sensitivity of these cells to TG003 was comparable to that of p53-wild-type cell lines indicating that TG003-induced growth inhibition can occur in a p53-independent manner. To assess the contribution of the p53 pathway in the p53 wild-type MM001 and MM117 lines, p53 was depleted by shRNA; TG003 toxicity, as measured by quantification of cleaved caspase 3/7, was at least partially rescued by p53 depletion (data not shown). These data indicate that exon 6 skipping and MDM4 downregulation can be achieved by pharmacological targeting of the splicing machinery. However, although this approach allows reactivation of p53 tumor suppressor function in cells harboring wild-type p53 it also promotes unspecific p53-independent killing activities.

In aggregate, pharmacological and genetic inactivation of SRSF3 compromises MDM4 exon 6 inclusion, thereby leading to activation of p53. Consistently, this is accompanied by a decrease in melanoma growth and survival. However, since SRSF3 targets multiple pro-oncogenic splicing events (36) this effect is unlikely to be caused solely by a decrease in MDM4 exon 6 inclusion.

Figure 7A:
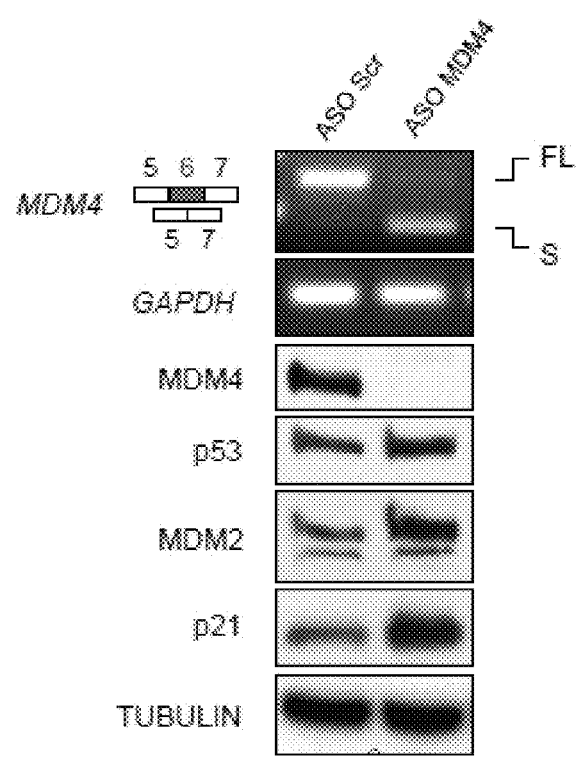
FIGS. 7A-7H: ASO-mediated exon 6 skipping decreases MDM4 protein abundance and melanoma growth in vitro and in vivo.
Figure 7B:
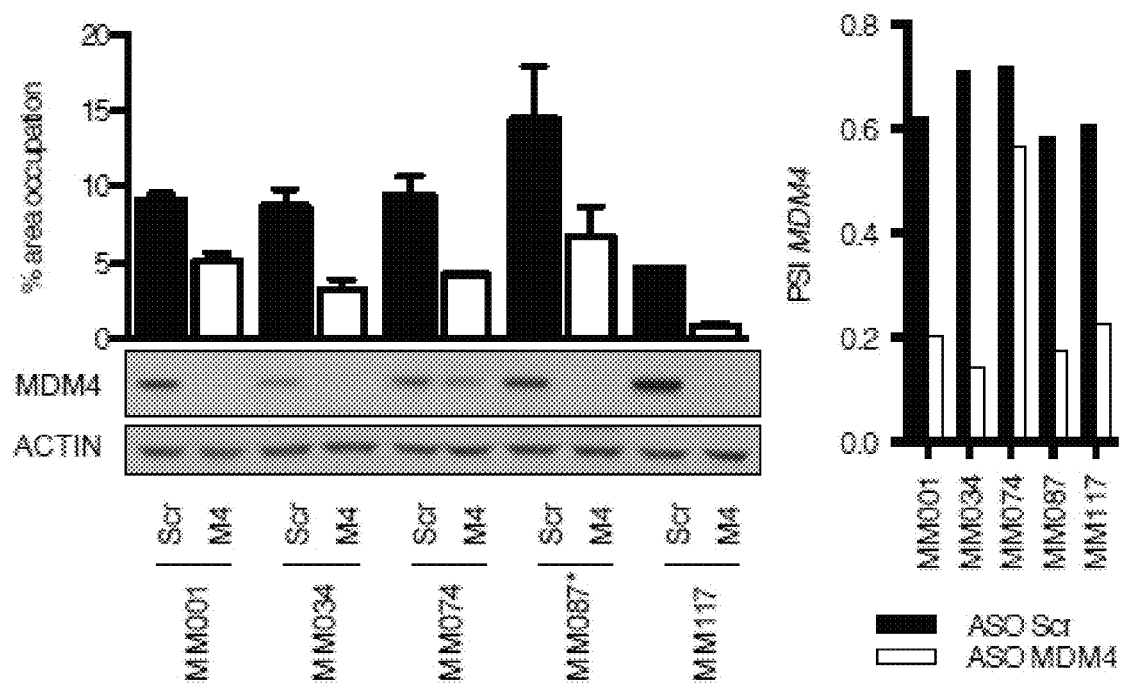
Figure 8A:
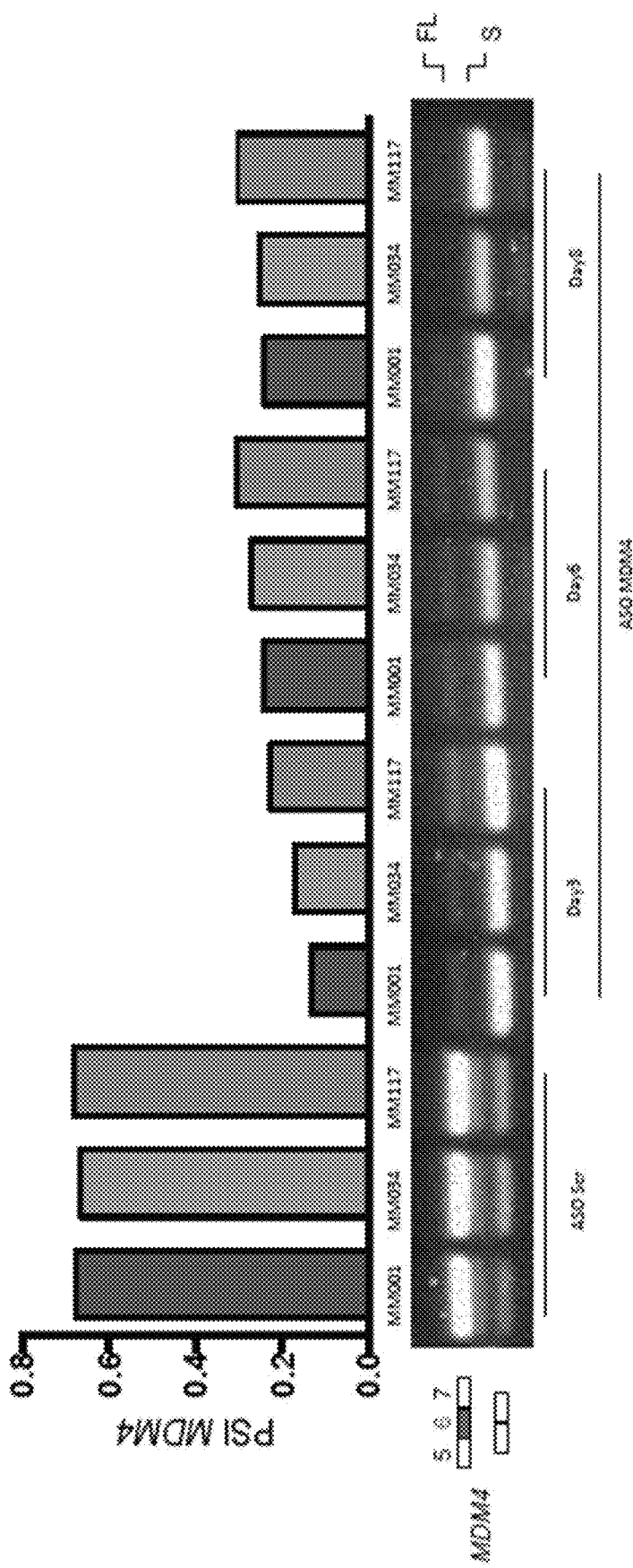
FIGS. 8A-8D.
Figure 8B:
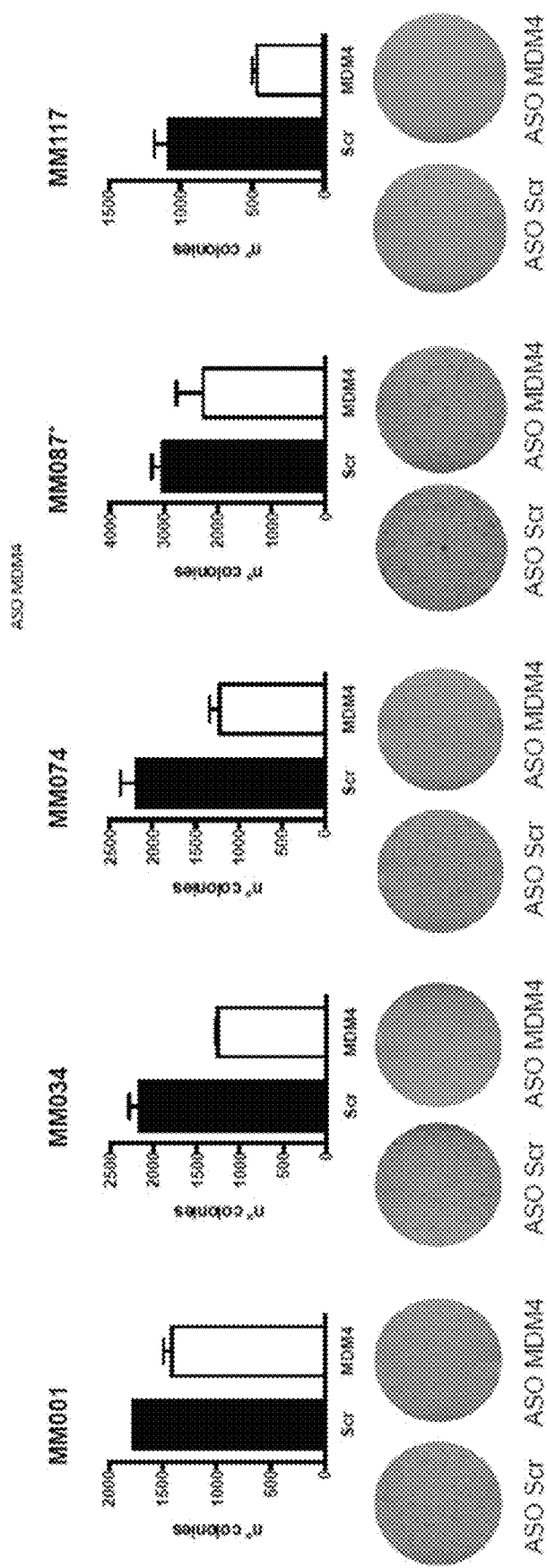
Figure 8C:
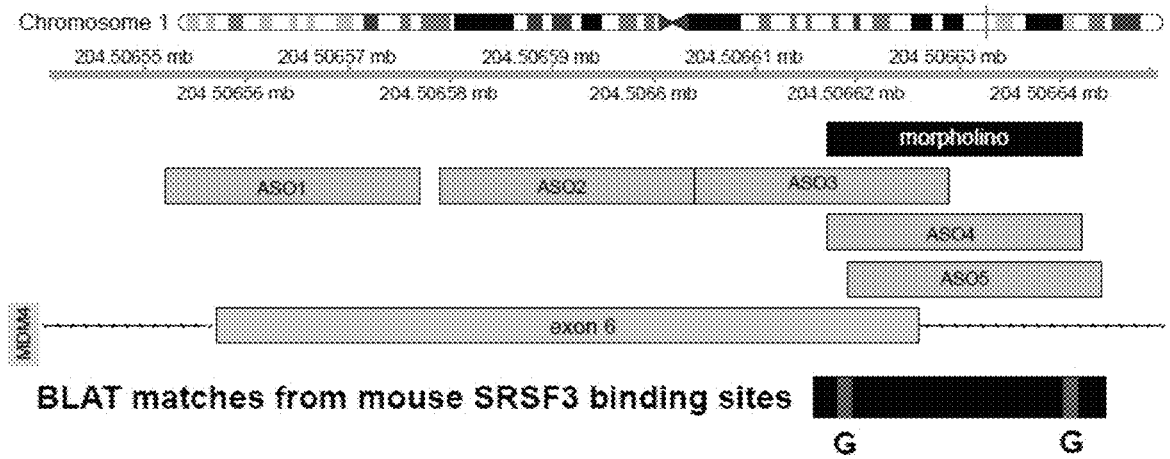
Figure 8C:
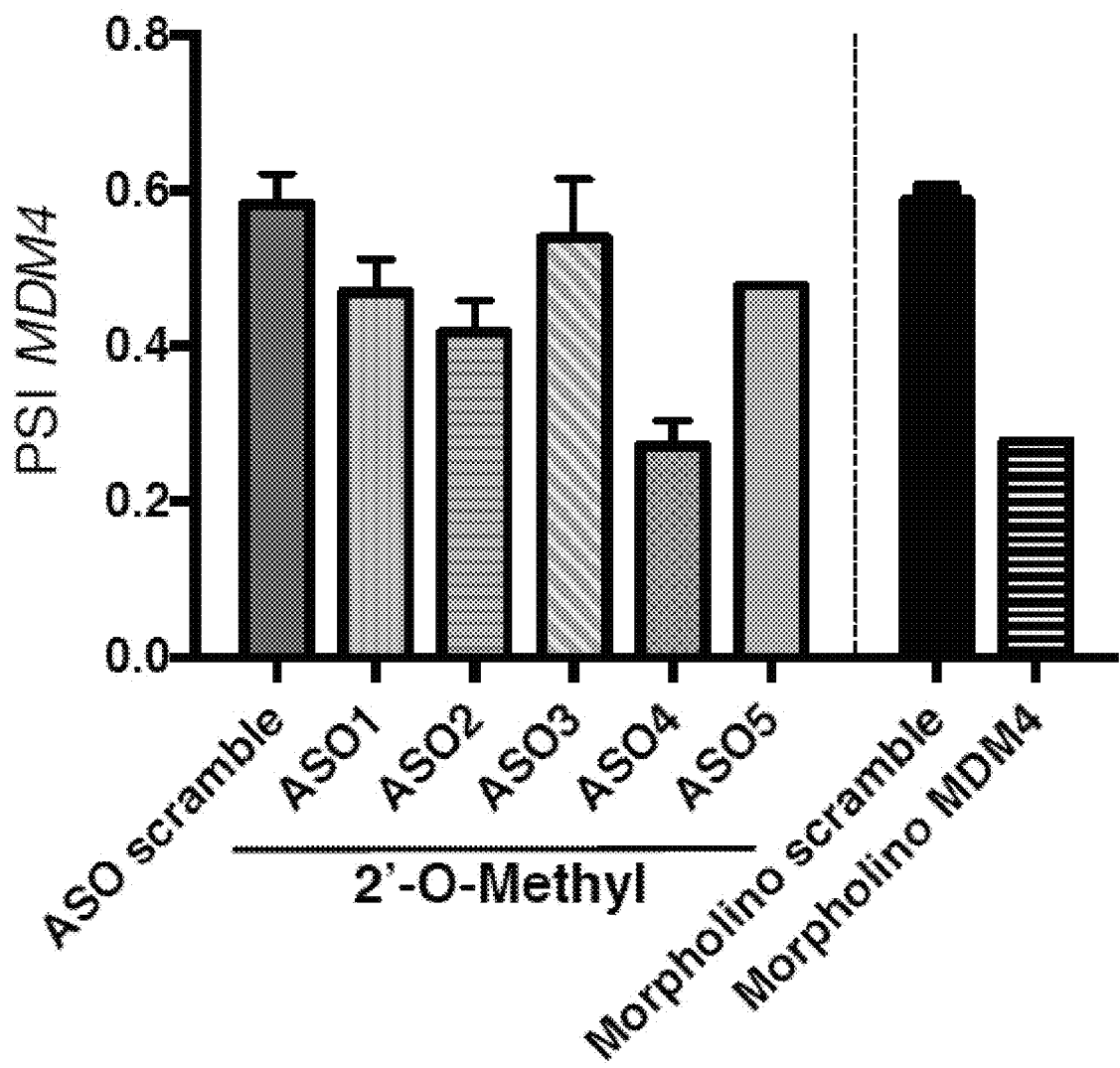

Example 3. Antisense Oligonucleotide (ASO)-Mediated Exon 6 Skipping Efficiently Decreases MDM4 Abundance and Melanoma Growth In order to more specifically target exon 6 inclusion, a splice switching morpholino ASO was designed, flanking the exon-intron boundaries of exon 6 (ASO MDM4) and overlapping with one of the SRSF3 binding sites (FIG. 6B). Transfection of a series of MDM4-expressing melanoma cell lines and short-term cultures with ASO MDM4, but not with a non-targeting/scramble ASO control (Scr), led to efficient exon 6 skipping and a subsequent decrease in MDM4 protein abundance (FIGS. 7A and 7B). Notably, the exon-skipping event was stable up to eight days post-transfection (FIG. 8A). ASO-induced exon 6 skipping unleashed p53 activity, as evidenced by an increase in expression of its well-established target genes p21 and MDM2 (FIG. 7A). Accordingly, ASO MDM4 decreased the ability of TP53-wild-type melanoma cultures to grow in vitro (FIG. 7B and FIG. 8B). Although a morpholino backbone was selected for the in vitro and subsequent in vivo studies, an alternative backbone chemistry was also tested, given the recent successes of phosphorothioate backbone ASOs in the clinic (39). As previously demonstrated for other targets (40), the induction of MDM4 exon 6 skipping is not dependent on the chemistry of the ASO, but rather on the position of its targeting sequence, as the most efficient 2-OMe/phosphorothioate backbone ASOs target the 5'-donor site and overlap with a SRSF3 binding site, similarly to the morpholino ASO MDM4 (FIG. 8C).

There is an increased body of evidence that MDM4 also possesses p53-independent oncogenic functions (2, 18-21). Since ASO-mediated exon 6 skipping directly affects MDM4 abundance, and not its ability to interact with p53, this approach is expected to also impact on the growth of MDM4-expressing TP53 mutant melanoma cells. Accordingly, the growth of the short-term melanoma cultures from patient sample MM087 was significantly reduced when exposed to the exon 6 targeting ASO (FIG. 7B and FIG. 8B).

Example 4. ASO-Mediated MDM4 Exon 6 Skipping Decreases Melanoma Growth In Vivo

Together the above data indicate that ASO-mediated exon 6 skipping is a promising anti-melanoma therapeutic strategy. To test the in vivo applicability of this approach, patient-derived-xenograft (PDX) models of melanoma were established and three of these models (MEL002, MEL010 and MEL006) were selected for further experiments based on their detectable levels of MDM4 protein expression (data not shown and FIG. 7D). When tumors reached an average volume of 150 to 200 mm$^3$, MEL002 cohorts were treated with the MDM4 ASO (or Scr control) covalently linked to a delivery moiety, which is comprised of an octa-guanidine dendrimer ("vivo morpholino"), by intra-tumor (IT) injections every two days. Tumor development was monitored in both cohorts for a period of 16 days. At the end of the experiments tumors were dissected and processed for histological and biochemical analyses.

Figure 7C:
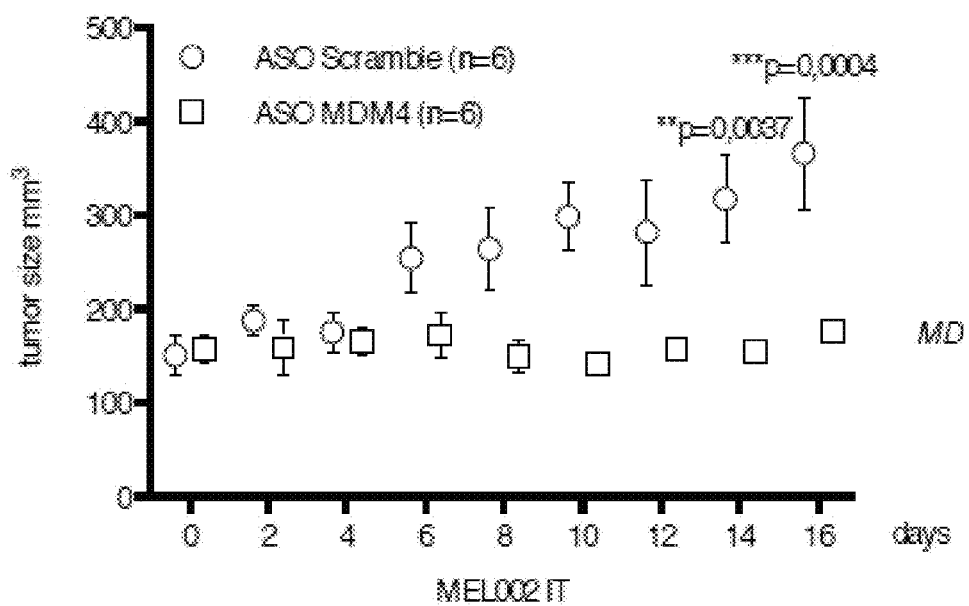
Figure 7D:
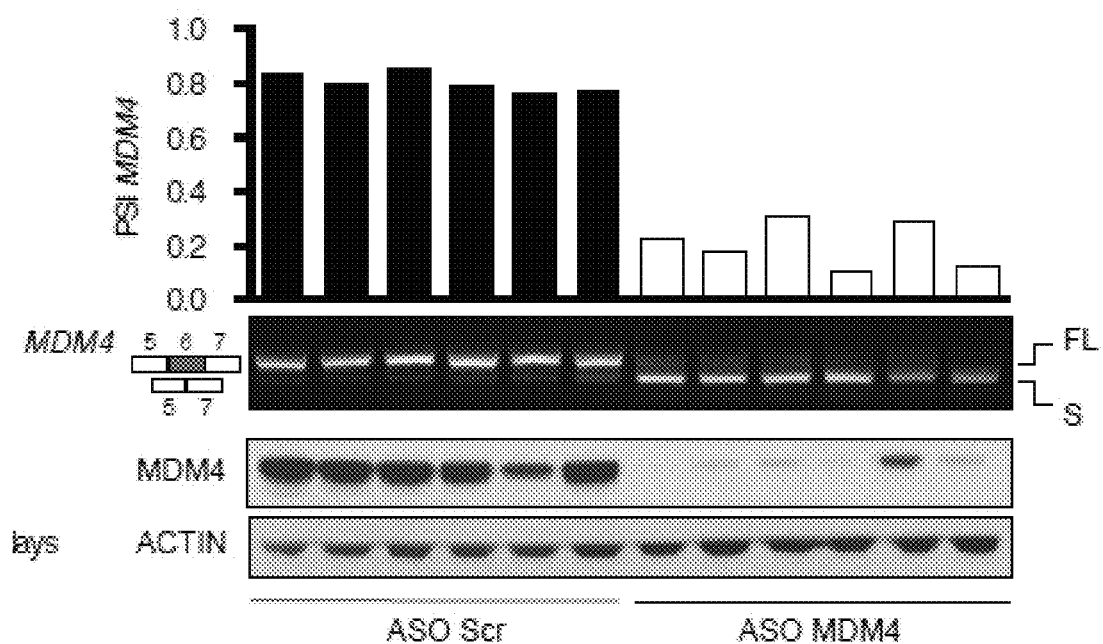
Figure 7E:
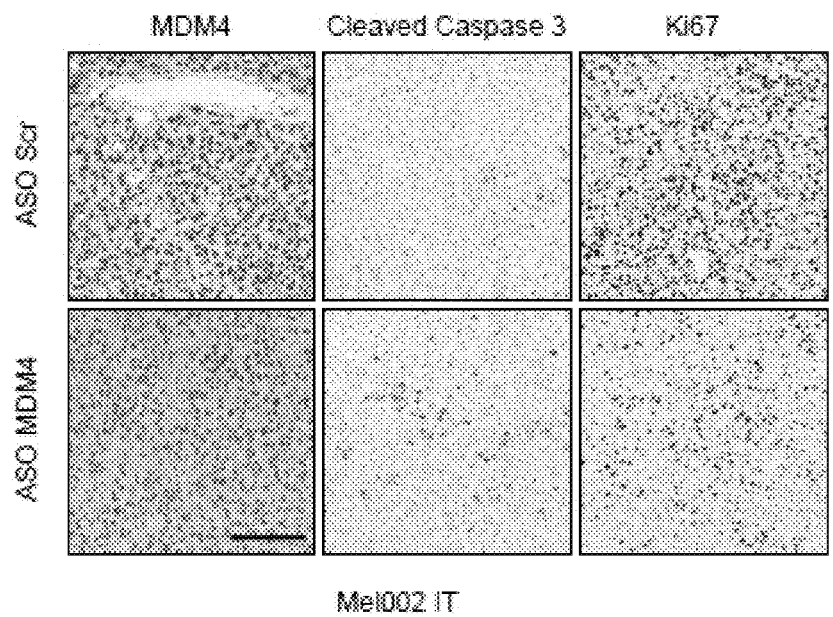
Figure 7F:
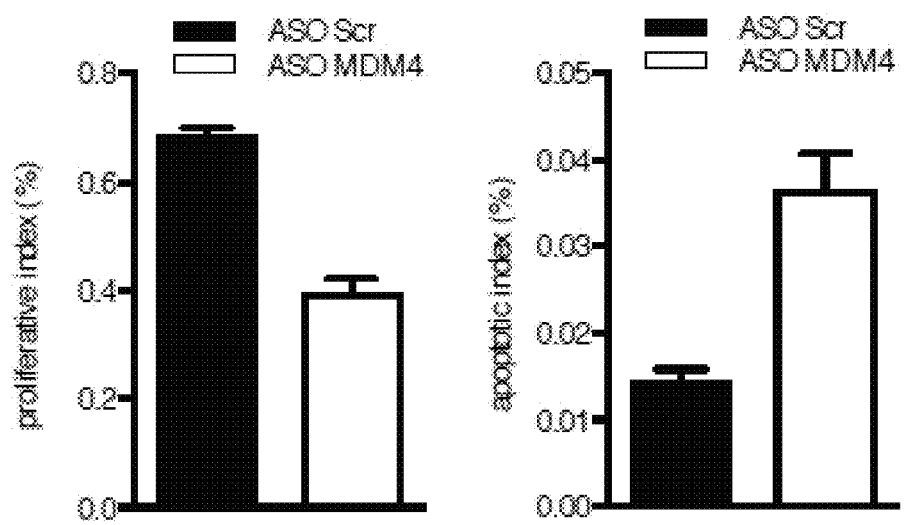
Figure 8D:
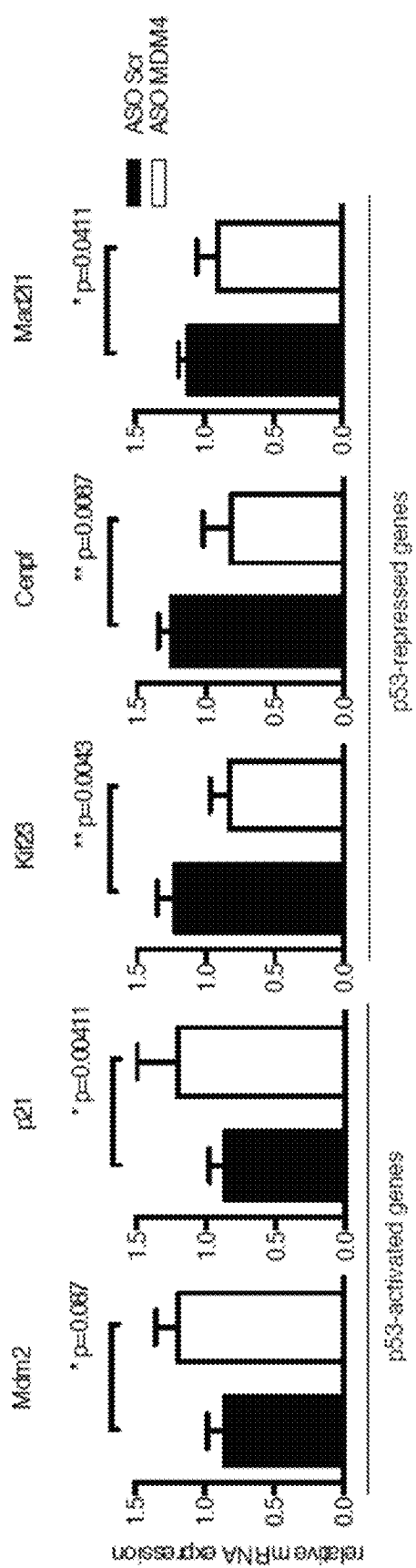

A significant reduction in tumor growth was observed in melanoma samples exposed to the exon 6 targeting ASO (FIG. 7C). Strikingly, whereas expression of the protein-coding isoform was predominant in all lesions exposed to the scramble ASO a dramatic switch towards expression of the MDM4-S isoform was observed in all melanoma samples exposed to the exon 6-targeting ASO (FIG. 7D). This switch led to a robust decrease in MDM4 protein expression (FIGS. 7D and 7E). Histological examination and IHC analyses attributed this effect on tumor growth to a significant decrease in cell proliferation, as evidenced by a striking decrease in KI67-positive cells, accompanied by an increase in apoptotic cell death (FIGS. 7E and 7F). Concomitantly, loss of MDM4 protein by MDM4 ASO treatment stimulated p53-signaling with the upregulation of p53-activated genes like MDM2 and p21 and downregulation of p53-repressed genes like KIF23, CENPF and MAD2L1 (FIG. 8D).

Figure 7G:
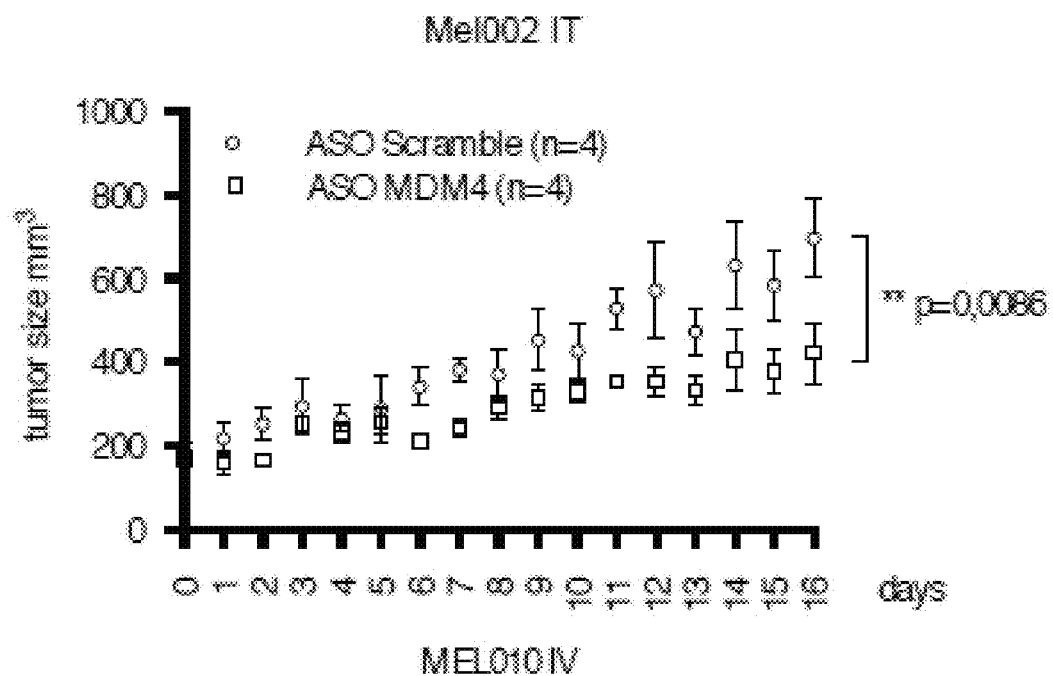
Figure 7H:
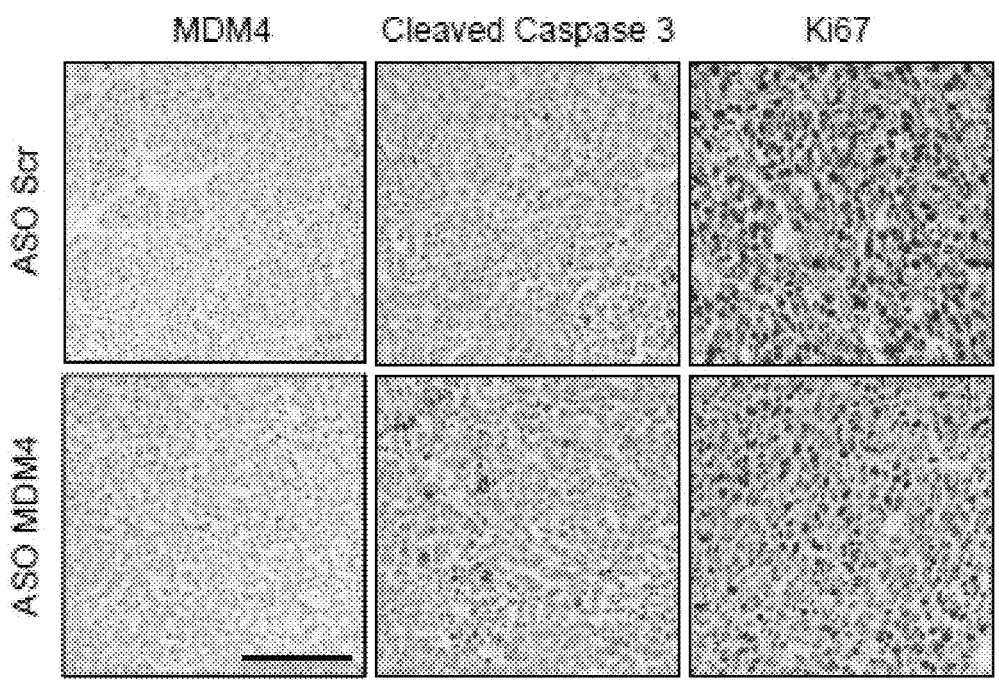

Furthermore, delivery of the MDM4 ASO by intravenous injections (IV) every two days also decreased tumor growth in yet another melanoma PDX model (MEL010; FIG. 7G). In close proximity to blood vessels this decrease was also accompanied by a measurable reduction in MDM4 protein expression, reduced cell proliferation and an increase in apoptotic cell death (FIGS. 7G and 7H).

Collectively, these data highlight the in vivo pharmacologic potential of this approach for the treatment of melanoma.

Figure 9A:
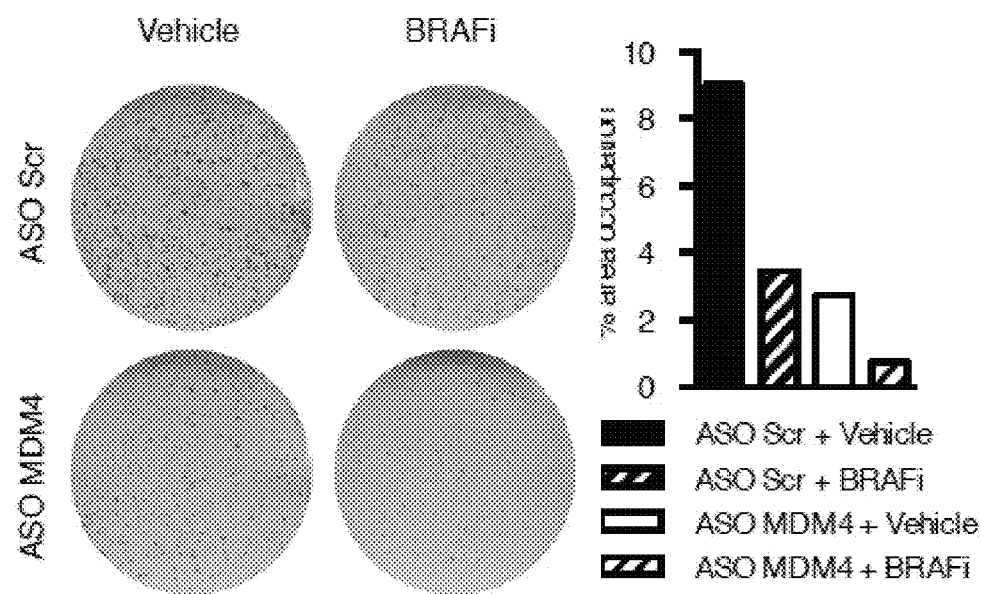
FIGS. 9A-9E: ASO-mediated exon 6 skipping sensitizes melanoma cells to BRAFV600E-inhibitors in vitro and in vivo.

Example 5. ASO-Mediated MDM4 Exon 6 Skipping Sensitizes Melanoma to BRAFV600E-Inhibition The management of intrinsic resistance to MAPK-targeting inhibitors is likely to be achieved through therapeutic modalities that simultaneously target multiple pathways. Importantly, as targeting the MDM4-p53 interaction using a stapled-peptide sensitizes melanoma cells to inhibition of BRAFV600E (13), ASO-mediated exon 6 skipping increased the sensitivity of cultured BRAFV600E-mutant melanoma cells to the BRAFV600E-inhibitor vemurafenib (FIG. 9A).

Figure 9B:
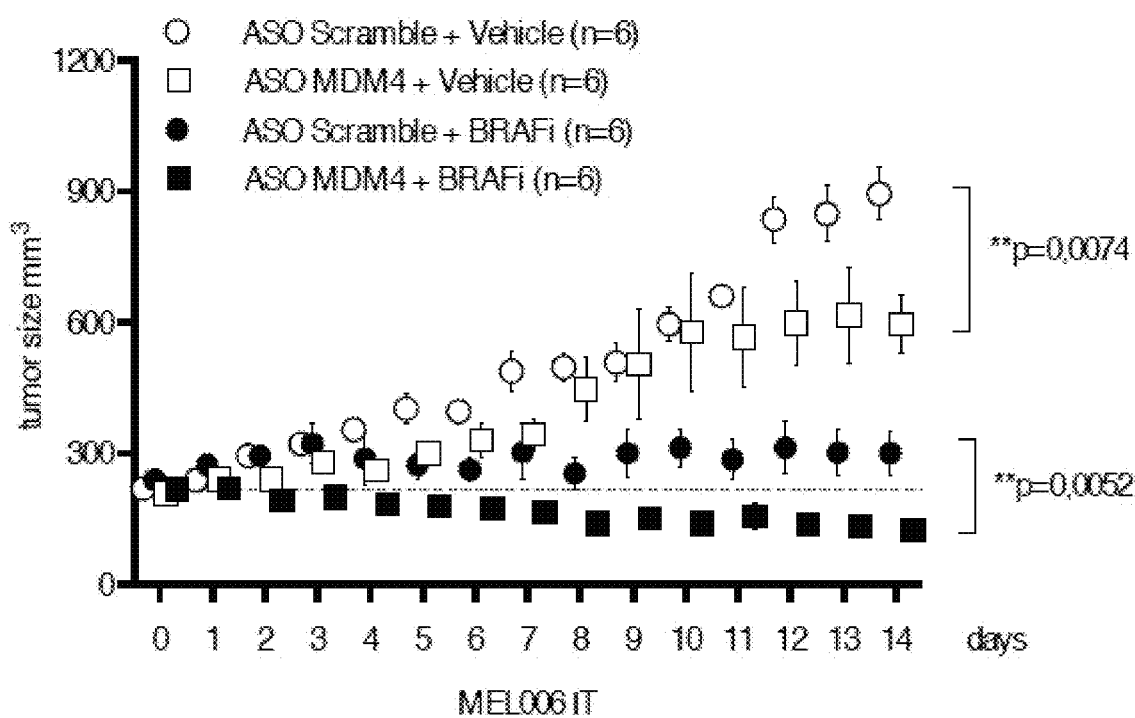
Figure 9C:
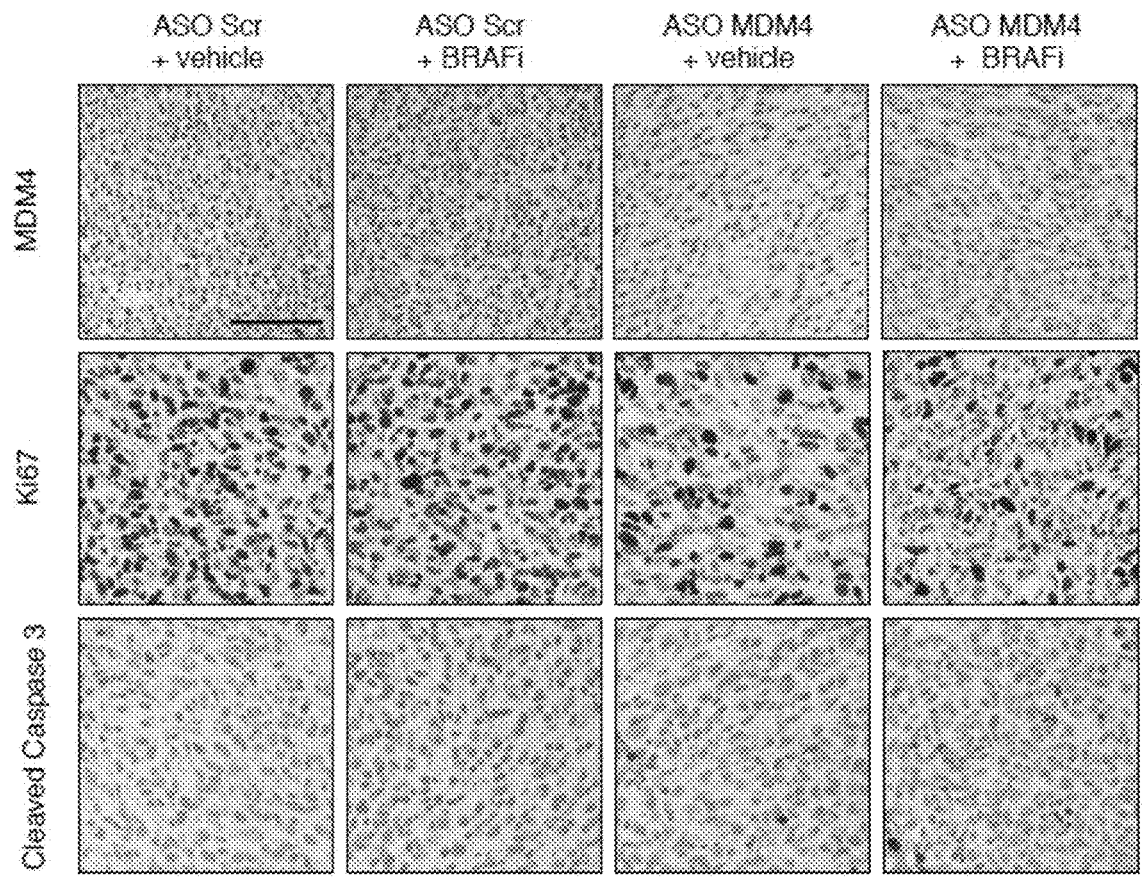
Figure 9D:
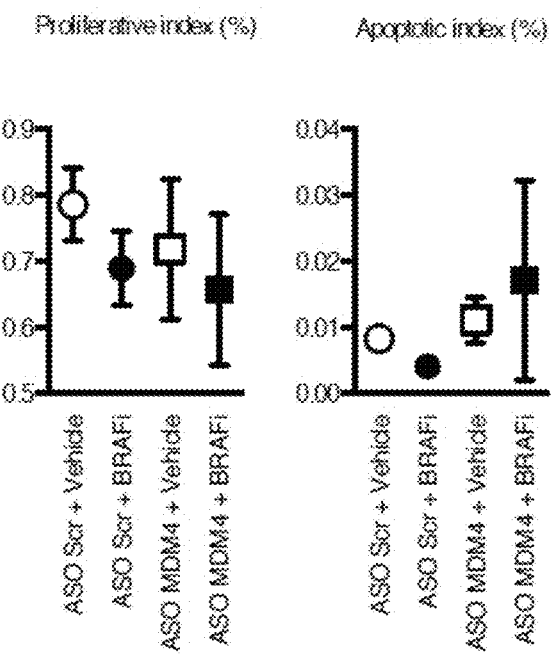
Figure 9E:
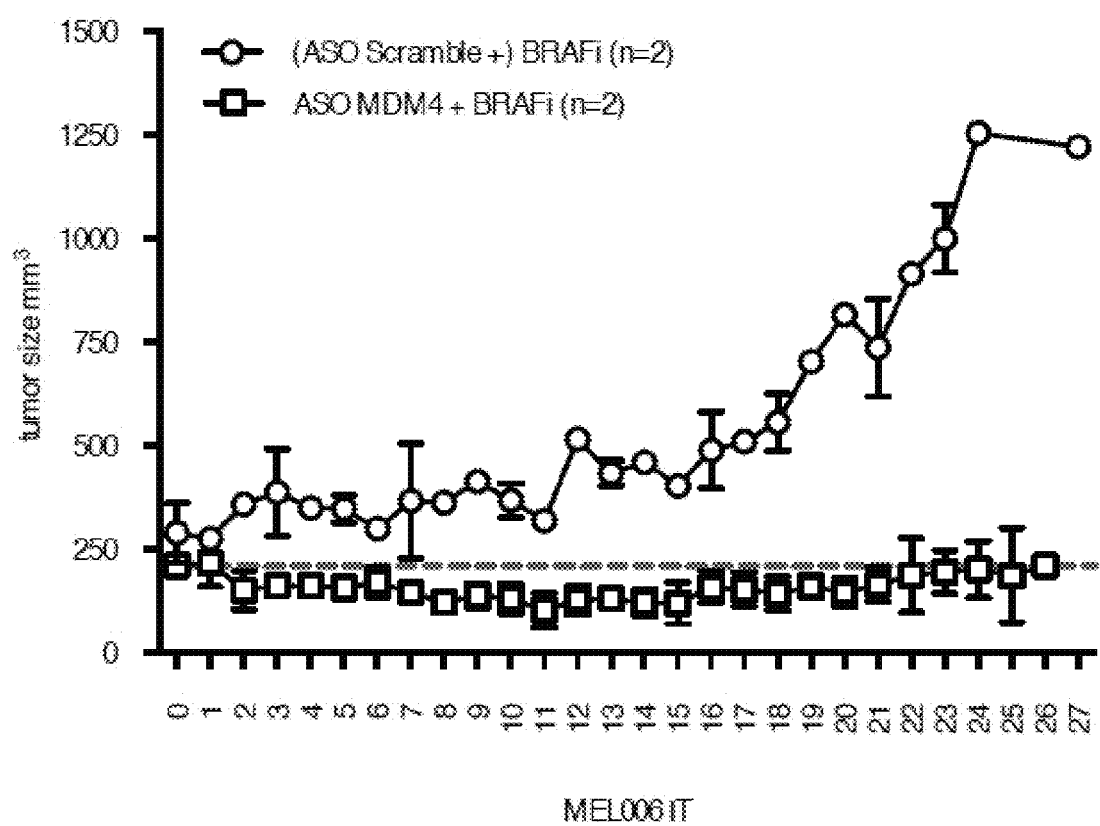

This analysis was extended by co-treating cohorts of MEL006, a BRAFV600E-mutant melanoma PDX model (Table 1), with BRAFV600E-inhibitor Dabrafenib daily and intratumor injection of the MDM4 morpholino every other day for 14 days. Importantly, whereas tumor growth was only inhibited following exposure to the BRAFV600E-inhibitor Dabrafenib alone, robust tumor regression was observed in the MEL006 PDX cohort treated with Dabrafenib and the MDM4 ASO (FIG. 9B), and this was due, at least partly, to a measurable increase in apoptotic cell death (FIGS. 9C and 9D). Even more interestingly, whereas mice acquired resistance to the BRAFV600E inhibitor treatment within 20 days of exposure, two out of two mice treated with the combination Dabrafenib/MDM4 ASO did not (FIG. 9E). These observations raise the exciting possibility that ASO-mediated targeting of MDM4 might be a valid strategy to significantly delay, and/or possibly suppress, acquisition of resistance to treatments with BRAFV600E-inhibitors alone. Notably, Dabrafenib/MDM4 ASO-treated mice did not suffer from weight loss during the course of the experiment in contrast to mice treated with a combination of Dabrafenib and the MEK-inhibitor Trametinib (data not shown). Moreover, complete histopathological examination of mice exposed to the Dabrafenib/MDM4 ASO combination did not reveal any relevant adverse events. In contrast, mice treated with the Dabrafenib/Trametinib combination suffer from well-documented adverse events associated with this treatment in humans including severe renal lesions (41).

Figure 10A:
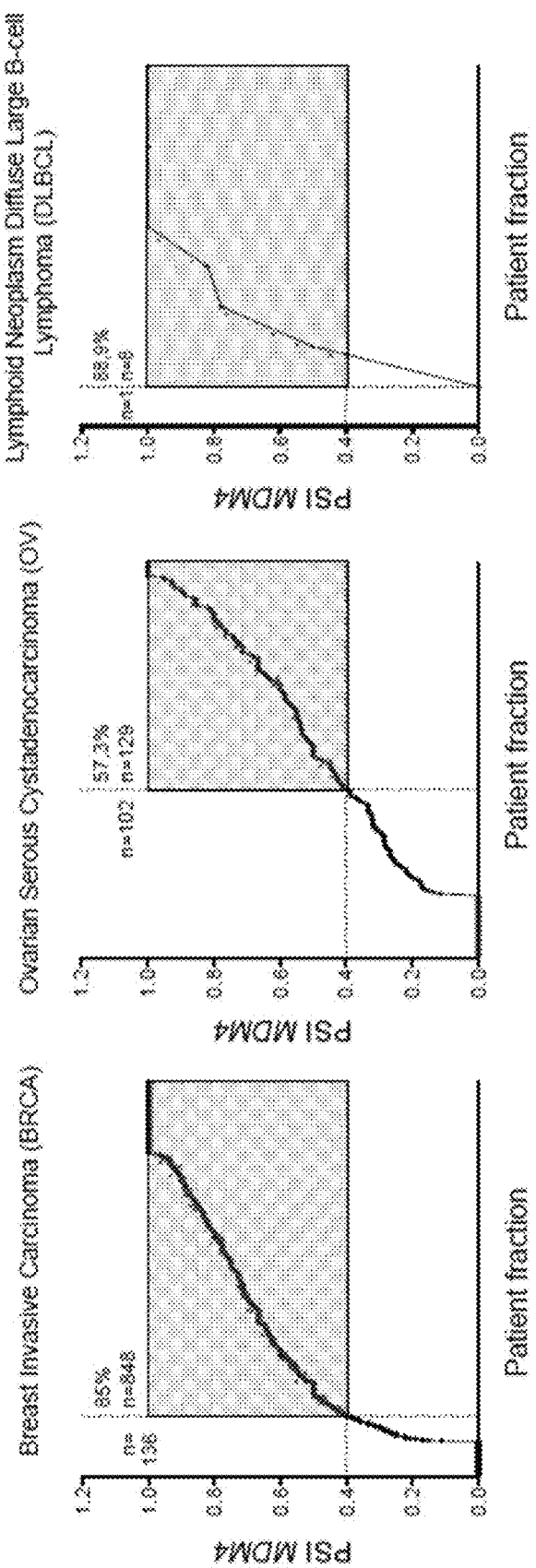
FIGS. 10A-10F: The ASO-mediated MDM4 therapeutic strategy is applicable to several tumor types.
Figure 11:
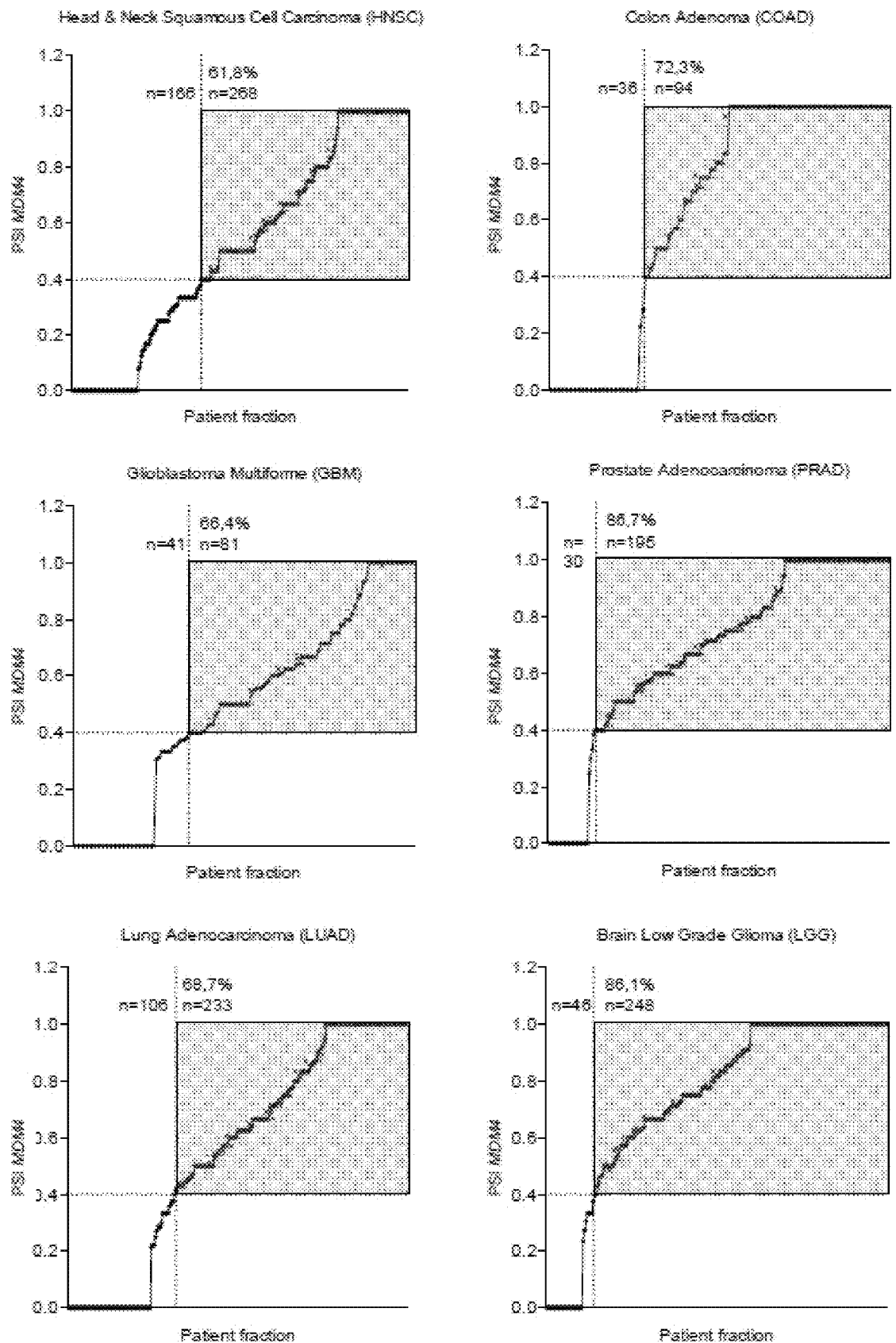
FIG. 11: The PSI MDM4 index was calculated, similar to that described in FIG. 2B, for Head and Neck squamous cell carcinoma (HNSC), Colon adenoma (COAD), Glioblastoma Multiforme (GBM), Prostate adenocarcinoma (PRAD), Lung adenocarcinoma (LUAD) and Brain Low grade Glioma (LGG). For each tumor type, all values were sorted and plotted. The red area indicates the tumor specimens with PSIMDM4>0.4; the total percentage of tumor samples in this area is indicated in the top left corner.

Example 6. ASO-Mediated MDM4 Targeting is a Therapeutic Strategy Applicable to Several Tumor Types This estimation of the proportion of human tumors expressing the MDM4 protein is primarily based on measurements performed at the total mRNA level (10, 11). In order to revise these numbers, and since it was found that the PSI index is a much more reliable predictor of MDM4 protein level than total MDM4 mRNA in melanoma, and this ratio was determined in hundreds of human tumors of different types using publically available RNA-seq datasets (FIG. 10A and FIG. 11). Strikingly, it was found that the PSI index is higher than 0.4 in 85% of the breast carcinoma (BRCA) samples (FIG. 10A).

Figure 10B:
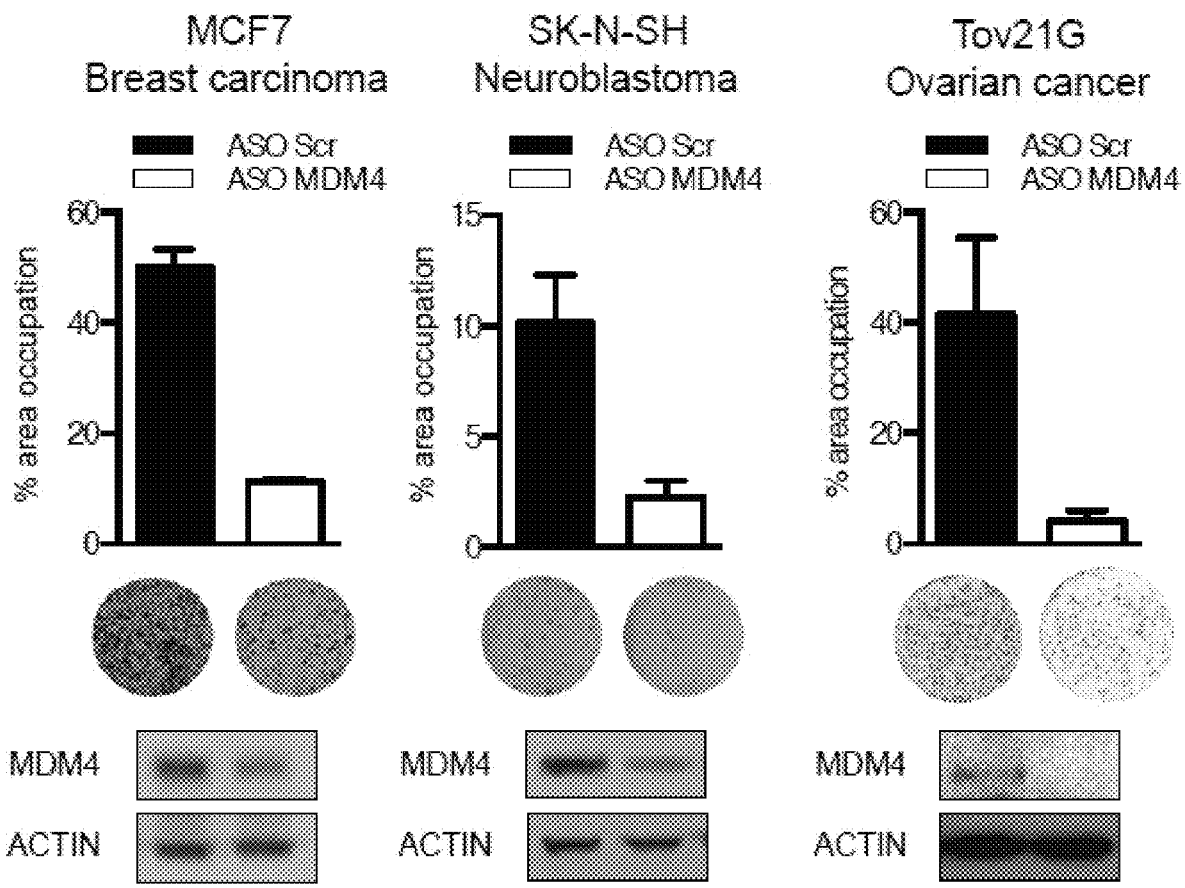
Figure 12:
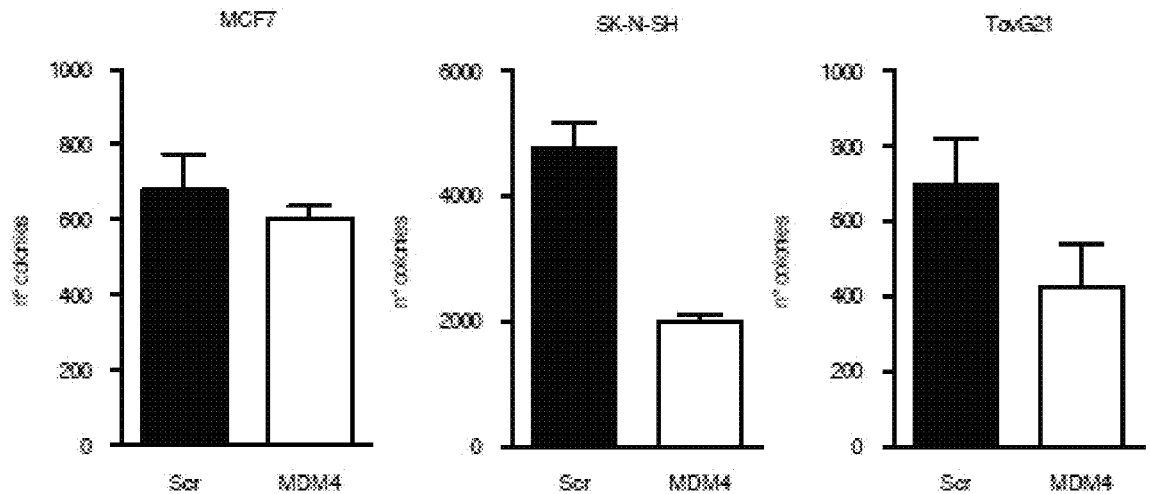
FIG. 12: MCF-7 breast cancer, SK-N-SH neuroblastoma and Tov21G ovarian cancer cultures were transfected with MDM4-targeting and scramble (Scr) control ASOs and colony formation was evaluated using low-density colony formation assays ten days after seeding. For the quantification of the colony formation assays, the data are presented as the mean number of colonies counted for multiple different biological replicates (±SD).

The prediction from this analysis is that roughly 85% of human breast carcinoma expresses the MDM4 protein, which is in sharp contrast with the 20% deduced from mRNA measurements, and in agreement with broad MDM4 protein overexpression observed in breast cancer lines (42). A similar analysis predicts that MDM4 is, for instance, expressed in 57%, 62% and 72% of Ovarian Serous cystadenocarcinoma (OV), head and neck squamous cell carcinoma (HNSC) and colon adenoma (COAD), respectively (FIG. 10A and FIG. 11). Importantly, the growth of non-melanoma MDM4-expressing TP53 wild-type cancer cell lines, such as the breast cancer cell line MCF-7, neuroblastoma cell line SK-N-SH and ovarian cancer cell line Tov21G was strongly inhibited upon exposure to the MDM4 ASO (FIG. 10B and FIG. 12).

Figure 10C:
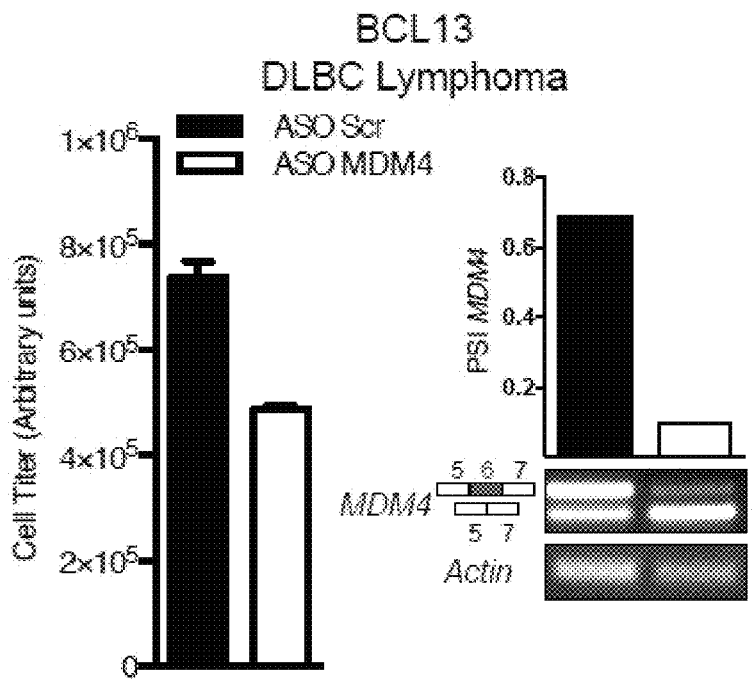
Figure 10D:
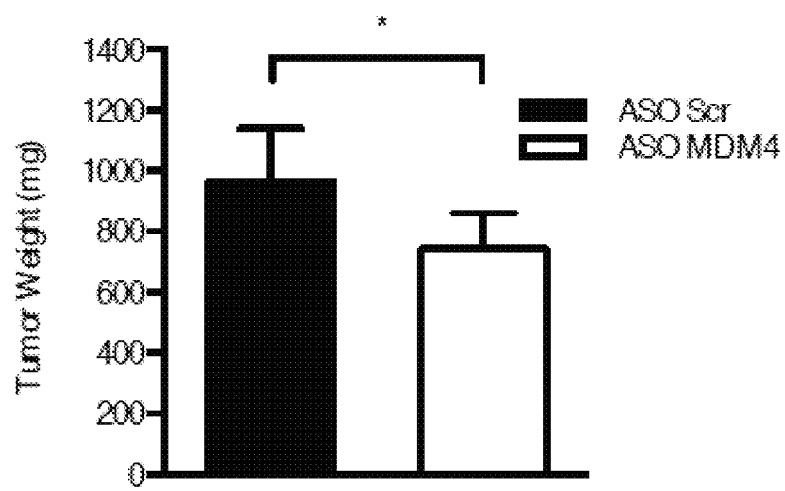
Figure 10E:
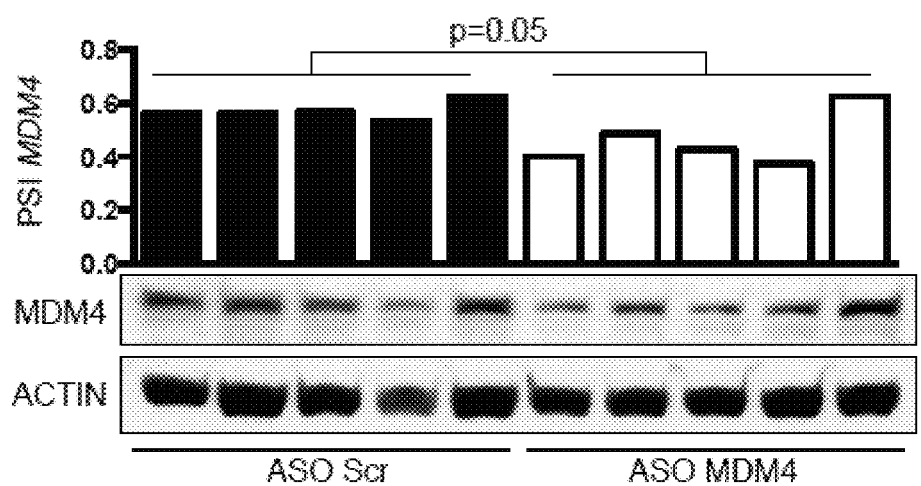
Figure 10F:
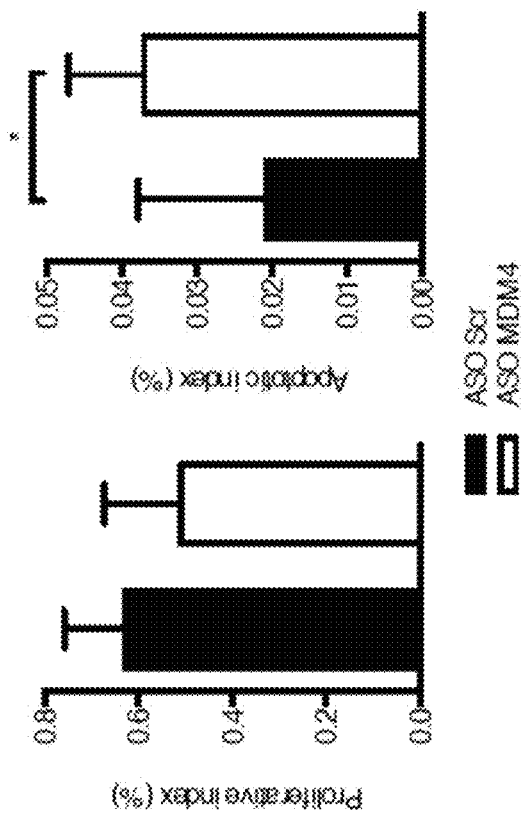
Figure 10F:
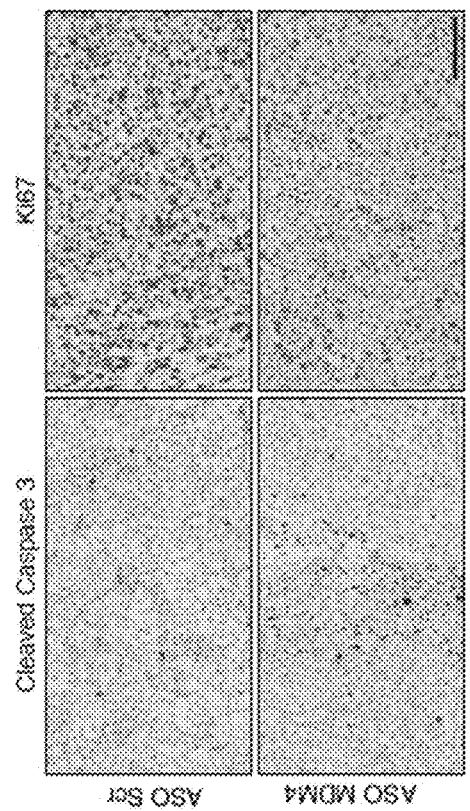

To test whether ASO-mediated MDM4 targeting is a therapeutic approach that is applicable to tumors other than melanoma in an in vivo context, a PDX model of diffuse large B cell lymphoma (DLBCL; BCL13) was established. First, primary DLBCL cells were cultured from this model and established that ASO MDM4 reduced their viability in vitro (FIG. 10C). When tumors reached an average volume of 150 to 200 $mm^3$, ASO MDM4 (or Scr control) was injected intra-tumorally (IT), every two days and tumor development was monitored for a period of 20 days. At the end of the experiments tumors were dissected and processed for histological and biochemical analyses. A significant reduction in tumor growth was observed in DLBCL bearing mice exposed to ASO MDM4 (FIG. 10D). Consistently, a reduction in PSI indexes and MDM4 protein levels in lesions exposed to ASO MDM4 was observed (FIG. 10E). This was accompanied by a significant decrease in cell proliferation (reduction in KI67-positive cells) and an increase in apoptotic cell death (increase cleaved caspase 3 staining) (FIG. 10F). Together these data demonstrate that the MDM4-targeting ASO-based therapeutic strategy is not only applicable to melanoma but may be valid clinical approach to a wide range of tumor types.

DISCUSSION

Figure 13:
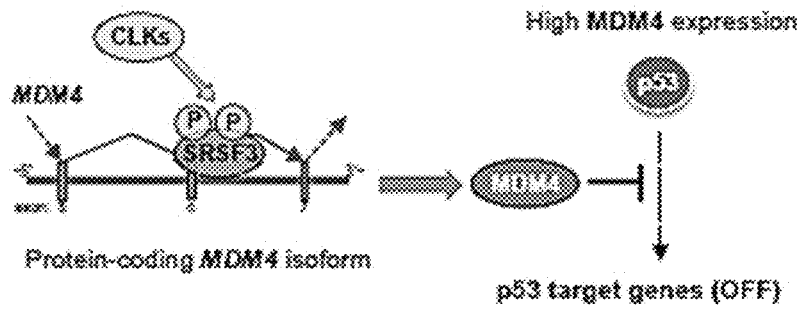
FIG. 13: Targeting MDM4 splicing in cancer therapy. Whereas MDM4 is unproductively spliced in most normal adult tissues, the MDM4 protein is highly expressed in embryonic tissues and in cancers as a result of enhanced exon 6 inclusion. SRSF3, among other SRSF family members, is the only one promoting Exon 6 inclusion. TG003 is a CLK inhibitor, which affects phosphorylation of multiple SR proteins. Inducing MDM4 exon 6 skipping via antisense oligonucleotides (ASO) is a very specific, efficient and clinically compatible approach to inhibit p53-dependent MDM4 oncogenic functions.
Figure 13:
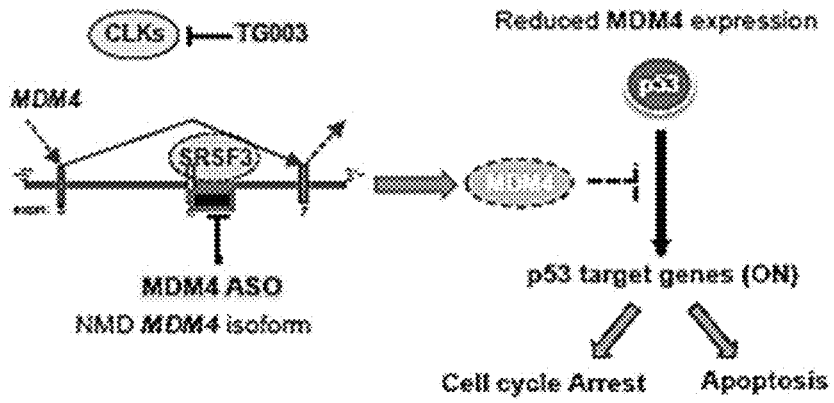

Identification of mechanisms that promote expression of the MDM4 oncoprotein will accelerate the development of anti-MDM4 targeted therapies, which are predicted to be active against a wide range of human cancers. Herein described is an unanticipated and widespread role for an AS-based mechanism in driving MDM4 overexpression. It is shown that MDM4 exon 6 is a "NMD switch" exon that is skipped in most normal adult tissues resulting in the production of a transcript that is degraded by NMD. In contrast, the coding splice isoform is produced in melanoma (and other cancer) cells as a result of enhanced exon 6 inclusion (FIG. 13).

In non-transformed cells the MDM4-S isoform is rapidly degraded (26). In cancer cells however, the efficiency of the NMD pathway is often compromised (43, 44). Consistently, MDM4-S is readily detectable in melanoma, and inhibition of NMD by cyclohexamide did not lead to a consistent increase in MDM4-S levels (data not shown). Importantly, previous evidence indicates that MDM4-S is inefficiently translated (26) and that the MDM4-S peptide is highly unstable (26, 27, 45). Together these observations provide a rational explanation for the inability to detect the MDM4-S protein in melanoma or other cancers (data not shown and (45)).

Mechanistically, it is shown that although several SR proteins (46) may participate in the regulation of MDM4 AS, SRSF3 is one key enhancer of exon 6 inclusion in melanoma cells. Consistent with this possibility SRSF3 is a well-established oncogene (36, 47). It is directly regulated at the transcriptional level by Wnt signaling (48), a pathway often upregulated in cancer (49). In turn, SRSF3 promotes several oncogenic AS events, such as exon 10 inclusion in the pyruvate kinase M gene, generating the PKM2 isoform, which promotes aerobic glycolysis in cancer cells (50). The data, therefore, identifies a novel mechanism underlying SRSF3 oncogenic function, namely the regulation of MDM4 AS and in turn suppression of p53 activity. Interestingly, SRSF3 may also directly affect p53 AS, to suppress expression of the p53beta isoform that promotes p53-mediated senescence (51).

Importantly, a striking correlation between the PSI index and MDM4 protein abundance was observed in the majority of the melanoma samples analyzed indicating that the MDM4 splicing switch is one of the key mechanisms that account for the frequent overexpression of MDM4 in melanoma. Of note, the correlation between the PSI index and MDM4 protein abundance is not strict as a few normal tissues (i.e., liver) and melanoma samples (i.e., MM099) were identified in which this correlation could not be established. This indicates that other mechanisms, either post-transcriptional or post-translational, may also contribute to regulation of MDM4 expression in a small proportion of cases.

The identification of this novel mechanism regulating MDM4 protein levels in cancer has significant therapeutic implications. Restoration of the wild-type p53 tumor suppressor function is an attractive and promising, yet extremely challenging, anti-cancer strategy. It has been previously demonstrated that targeting the MDM4-p53 interaction represents a unique and safe therapeutic opportunity to reactivate suppressed wild-type p53 function. Unfortunately, small molecules (or stapled-peptides) that selectively and efficiently disrupt the MDM4-p53 complexes have so far not been developed adequately for clinical testing. The strategy to target MDM4 AS described herein, allows specific manipulation of MDM4 abundance, rather than interactions with MDM4 partner proteins (FIG. 13). It is shown that this approach reactivates p53 function in TP53 wild-type melanoma cells and efficiently suppress their growth in vitro and in vivo. Importantly, the strategy of targeting MDM4 AS is, in theory, not only applicable to melanoma but to any cancer that overexpresses MDM4. Accordingly, it is shown that the growth of cell lines of diverse origins (breast cancer, neuroblastoma, ovarian and DLBCL) is strongly inhibited upon exposure to the ASO MDM4.

Moreover, because this therapeutic approach targets MDM4 protein abundance rather than its interaction with p53 it can, in principle, also be used to target the recently described p53-independent oncogenic activities of MDM4 (FIG. 13). Accordingly, it is shown herein that targeting exon 6 inclusion decreases the growth of a TP53 mutant melanoma cell line, which express detectable levels of the MDM4 protein. Note, however, that cutaneous melanomas harboring mutant TP53 and expressing significant amount of the MDM4 protein are extremely rare (<3%).

The clinical relevance of this observation for melanoma patients is, therefore, limited. However, this provides proof-of-concept evidence that, in theory, the therapeutic strategy described herein may be applicable to a broad spectrum of human tumors including those harboring p53 mutations. The current understanding of the proportion of human tumors expressing elevated MDM4 protein levels is primarily based total mRNA quantification (10, 11). These have led, for instance, to the conclusion that MDM4 is expressed in about 20% of breast carcinomas (9). Previous observations that MDM4 protein levels, but not mRNA levels, are elevated in 65% of human melanoma samples have raised the possibility that total mRNA measurements have dramatically underestimated the frequency of MDM4-expressing cancers. The analysis of the TCGA public RNA-seq datasets, using the PSI index as a guide to predict the proportion of MDM4 expressing samples, indeed supports this conclusion. The re-evaluation of these large data sets underpin the possibility that a very high number of cancer patients may benefit from an MDM4-targeting ASO-based therapeutic strategy.

Together, that data indicates that a wide range of cancer cells promote an otherwise embryonic-specific splicing event (26) to promote expression of the oncoprotein MDM4 (FIG. 13). ASO-mediated exon skipping therapy targets MDM4 abundance rather than its interaction with p53 and, therefore, inhibits, in principle, both p53-dependent and independent oncogenic functions of MDM4 (FIG. 13). Given that the potential therapeutic benefit of a series of ASOs are being investigated in various clinical trials (39), and that one of these ASOs, Mipomersen, has recently been approved by the FDA (52) this therapeutic approach may be rapidly and widely applied to the clinic.

Methods

Cell Culture:

Human cell lines HEK293T, Phoenix-Eco, Phoenix-Ampho, A375, MCF-7 and SK-N-SH were obtained from American Type Culture Collection (ATCC) and propagated according to ATCC data sheets. UACC-62 (NCI-60) cells were a gift from Dr. Igor Kurochkin (BII, Singapore). Tov21G (CRL-117) were a gift from Dr. Ruby Yun-Ju Huang (CSI, Singapore). Melanoma cell lines (MM lines) are cultured in F-10 medium (cat. 11550-043, Gibco) supplemented with 10% Fetal Bovine Serum (Invitrogen), 1% Penicillin/streptomycin (Sigma-Aldrich) and with 12 ml L-alanyl-glutamine (from 200 mM stock, cat. 30-2115, ATCC) for 500 ml total medium.

Mouse Embryonic Stem cells (mES) were cultured in Dulbecco's modified Eagle Medium (Life Technologies) supplemented with 15% fetal bovine serum, 1× non-essential amino acids, 0.1 mM b-mercaptoethanol, 1% penicillin/streptomycin and 1000 units/ml LIF. Mouse embryonic fibroblasts that had been irradiated with 6.3 Gray were used as feeder cells. For differentiation, cells were cultured on culture dishes coated with 0.1% gelatin in Dulbecco's modified Eagle medium supplemented with 10% fetal bovine serum, 1×non-essential amino acids, 0.1 mM β-mercaptoethanol, 1% penicillin/streptomycin and 1 μM of alltrans-retinoic acid for the indicated time.

Chemicals:

TG003 (Cat. no. T5575) and retinoic acid (Cat. no. R2625) were purchased from Sigma-Aldrich, PLX4032 was purchased from SelleckChem (Cat. no. S1267).

Western Blotting:

Harvested cell culture pellets were resuspended in protein lysis buffer (25 mM HEPES pH 7.5; 0 M NaCl; 1.5 mM MgCl2; 2 mM EDTA; 2 mM EGTA; 1 mM DTT; 1% TRITON® X-100; 10% Glycerol; phosphatase/protease inhibitor cocktail), incubated on ice for 15 minutes and centrifuged for 15 minutes at 4° C. at 13000 rpm. Tissue samples were additionally homogenized with PRE-CELLYS® in protein lysis buffer, prior to incubation on ice. Protein concentration was determined with Bradford assay on the resulting supernatant. Equal amounts of protein were run on 4-12% Bis-TrisNuPageNovex gels (Invitrogen) and transferred to a nitrocellulose membrane with an iBlot dryblot system (Life Technologies). Membrane blocking was done in 5% non-fat dry milk powder in TBS-0.2% TWEEN® and membranes were incubated with the appropriate primary antibodies. Membranes were subsequently incubated with specific horseradish peroxidase-conjugated secondary antibody (Cell Signaling). Proteins were detected by enhanced chemiluminescence (ECL) Western blotting detection reagents (Thermo Scientific).

The antibodies used are listed in Table 2.

PCR and RT-qPCR:

Harvested pellets were resuspended in Qiazol and processed according to manufacturer's instructions in the miRNEAsY® kit (Qiagen). Prior to processing, tissue samples were additionally homogenized with PRE-CELLYS® in QIAzoL®. RNA was quantified using a NANODROP® 1000 (Thermo Scientific) and 500-2000 ng was reverse-transcribed with the High-Capacity cDNA Reverse Transcription Kit (Life Technologies) according to manufacturer's instructions. qPCR was run with Life Technologies' Fast SYBR® Green Master Mix on a Roche LIGHTCYCLER® 384. Data processing with the qbase+2.6 software from Biogazelle relies on normalization with a minimum of two reference genes indicated as RefGen below. RT-qPCR primers are listed in Table 3.

MDM4/Mdm4 alternative splicing was visualized through semi-quantitative PCR amplifying the region around exon 6. Forward primer binding in exon 4 (exon 5 in mouse) and Reverse primer binding in exon 7 (exon 8 in mouse) generate two amplicons representative of MDM4-FL (250 nt) and MDM4-S (182 nt) (Mdm4-FL; 227 nt and Mdm4-S; 159 nt in mouse). PCR was performed for 27 cycles (45 seconds at 95° C.; 30 seconds at 58° C.; 40 seconds at 72° C.) using ~34 ng cDNA template. GAPDH/Gapdh was used as loading control. Products were visualized on a 2% agarose gel. Semi-qPCR primers are listed in Table 3.

TAQMAN® Assay

A TAQMAN® assay was designed to simultaneously quantify the amount of full-length (FL) and short (S) MDM4 isoform in cDNA samples. Two primers (Table 6), annealing to exon 5 and exon 7 respectively, amplify both isoforms (FIG. 1B, Step 1). The PCR product is loaded on 2% agarose gel and the two bands (FIG. 1B, Step 2) are individually cut and purified using QIAQuicK® Gel Extraction Kit (Qiagen, #28706). The amount of DNA after purification has been measured with NANODROP® 1000 (Thermo Scientific) and the concentration of amplicons' copy number was derived based on their length (FL: 162 bp, S:94 bp). Afterward, serial dilutions for the purified DNA (FIG. 1B, Step 3) have been used to identify a standard curve in order to relate the Ct value to the copy number of the single isoforms. In detail, the same primers of Step 1 have been used for the TAQMAN® reaction together with a probe overlapping exon 6-7 junction conjugated with TET (PrimeTime 5' TET/ZEN/3' IBFQ, IDT, Table 6) and a second probe overlapping exon 5-7 junction conjugated with FAM (PrimeTime 5' 6-FAM/ZEN/3' IBFQ, IDT, Table 6) (FIG. 1B, Step 4). TAQMAN® Fast Universal PCR MASTER-MIX® (Applied Biosystems, #4352042) has been used as 2× MASTERMIX®. The reaction has been loaded in 7900HT Fast real time PCR system (Applied Biosystem) to plot the Ct values for the respective dilutions of both FL and S isoform (FIG. 1B, Step 5). According to the standard curve obtained, the copy number of the two isoforms has been derived in all the samples analyzed.

Vectors and Infections.

pLKO-1 Mission lentiviral vectors (Sigma) were used for SRSF proteins knock down in human cell lines (Table 4). A scrambled shRNA (Scr) was used as control. HEK293T cells were transfected with pLKO vector together with packaging vectors. Cells were incubated for 18 hours, then fresh medium was added to the cells. After 24 hours, the medium containing the viral particles was collected, filtered using a 0.22 μm filter unit and added onto the target cells. 48 hours after the last infection, the medium was replaced with fresh growth medium containing puromycin (Merck-Calbiochem, 540411). Cells were selected for two days before harvesting.

SRSF3 and Myc-tag-SRSF3 were cloned into pMX vector (Addgene). Phoenix-Ampho cells were transfected together with packaging vector to produce the retroviral particles carrying pMX empty, pMX-SRSF3 and pMX- SRSF3-MycTag. Same protocol was used for viral particles collection, filtering and infection and collection of UACC-62 cells.

Morpholino Transfection

Scrambled morpholino and MDM4 Exon 6 targeting morpholino (sequences in Table 5) were obtained from GENETOOLS® (Gene Tools, LLC, USA). The lyophilized oligonucleotides were resuspended at a stock concentration of 1 mM. Since morpholino's backbone is non-polar, it has to be partially annealed with a normal DNA oligonucleotide in order to be transfected with LIPOFECTAMINE® reagent (LIPOFECTAMINE® 3000, Life Technologies). (Scr oligo: AAAAAAAAAAacactagagaatgata (SEQ ID NO: 71; Exon 6 oligo: AAAAAAAAAAcaactgaaggtaaaat (SEQ ID NO: 72). Transfections were performed in six-well plates when the cells are ~60% confluent. For each well a mix was prepared with 21.85 µl of DNA primer (from 100 µM stock), 2.78 µl of morpholino (from 1 mM stock), 125 µl OPTI-MEM® (Gibco, cat. 31985070) and 5 µl P3000 reagent (from LIPOFECTAMINE® 3000 kit). This mixture was added to a solution containing 7.5 µl LIPOFECTAMINE® 3000 and 125 µl OPTI-MEM®. After 5 minutes incubation the solution was added dropwise to the cells.

Colony Formation Assay

All cancer cell lines were transfected with morpholinos as described above. 24 hours after transfection, cells were trypsinized, counted and replated onto six-well plates at a density of 5×10³ cells. After 10 days, colonies were fixed and stained in a solution of 1% Crystal violet in 35% methanol for 15 minutes at RT and washed in PBS and tap water. Whole well images were made and automatically processed with ImageJ (W. S. Rasband, ImageJ, U. S. National Institutes of Health, Bethesda, Md., USA, image-j.nih.gov/ij/, 1997-2014.) to determine the percentage of area occupation and colony number.

Melanoma PDX

Original human tumor biopsies from primary and metastatic melanomas were received freshly from the operation theatre and all patients gave their written informed consent. Immediately after surgery, fresh tumor tissue was collected in transport medium, consisting of RPMI 1640 medium supplemented with penicillin/streptomycin (100 U/ml; 100 µg/ml), fungizone (1 µg/ml) and gentamicin (50 µg/ml; all from Life Technologies). One representative part was fixed in 10% neutral buffered formalin, and used for routine histopathological diagnosis. A second portion immediately adjacent to the one selected for histopathology was used for xenotransplantation. To ensure that melanoma was adequately represented in this latter specimen, histopathology was performed on thin tissue slices obtained from the sample for xenotransplantation. The remainder of the biopsy was snap frozen in liquid nitrogen-cooled isopentane and stored at −80° C. or gradually cooled in FBS (Fetal Bovine Serum, Perbio Science; Sterile DMSO Uvasol, Merck MILLIPORE®) and 10% DMSO and stored at −180° C. for re-transplantation later on. Tumor tissue was implanted in mice within 4 hours after sampling. Before implantation, tumor tissue was rinsed in PBS (Life Technologies) supplemented with penicillin/streptomycin and fungizone, minced into pieces of 8-10 mm³ and implanted in the interscapular region of anesthetized six-week-old female NOG mice (NOD.Cg-Prkdcscid Il2rgtm1Sug/JicTac; Taconic) (first generation, F1). When the tumors reached a tumor volume of 1500 mm³, mice were sacrificed, tumors were harvested and general necropsy was performed. Xenograft tumors were immediately fresh-frozen, formalin-fixed, stored in FBS and 10% DMSO or placed in Matrigel (BD Biosience, Matrigel Basement membrane matrix) for serial transplantation into another set of NOG mice. This process was repeated to produce subsequent generations of PDX models (F2, F3, F4, . . . ). To evaluate the maintenance of the morphology and main characteristics of the tumor of origin, formalin-fixed, paraffin-embedded (FFPE) tissues sections from patient tumor samples and xenografts of all established PDX models were stained with hematoxylin and eosin (H&E) and individually observed and reviewed by a human and veterinarian pathologist. All procedures involving human samples were approved by the UZ Leuven/KU Leuven Medical Ethical Committee (CommissieMedisch-eEthiek, approval number ML8713/S54185). All procedures involving animals were performed in accordance with the guidelines of the Catholic University of Leuven (KU Leuven) Animal Care and Use Ethical Committee (P147/2012).

Treatment with morpholinos was started when tumor volume of mice reached 100-200 mm³. Cohorts were treated intratumorally or intravenously with 0.12 mg of scramble or exon 6 targeting Vivo-Morpholinos (GeneTools, Inc.) dissolved in 70 µl PBS, every 2 days for the duration of the experiment. The BRAFi Dabrafenib was prepared by dissolving a capsule of TAFINLAR® in DMSO concentrated at 30 mg/ml, aliquoted and stored at −20° C. Aliquots were thawed and diluted 1/10 in PBS prior to gavaging. Treated mice were given a capped dose of 0.6 mg in 200 µl. Control mice were gavaged with 10% DMSO in a total volume of 200 µl PBS.

Tumor growth was monitored with a caliper and the volume was calculated using the following formula V=a×b2×0.5, where a is the largest and b the smallest diameter of the tumor. Tumors were dissected at the end of the treatment and used for further processing for RNA, protein and histology.

Electroporation of Morpholino in DLBCL Cells

Morpholinos were electroporated into DLBCL cells using the Neon Transfection System (Invitrogen), using the following parameters: 1200 V×20 msec×2 pulses. Two µl of 1 mM stock solution were diluted in a final volume of 2 ml of media for electroporation in a single well of a six-well plate.

CELLTITER-GLO® (Promega) and Caspase 3/7 Glo (Promega) assays were carried out 48 hours after electroporation as further described below in this section.

DLBCL PDX

All the procedures were approved and carried out in accordance with the guiding ethical principles of the Institutional review board (SGH). Written informed consent was obtained for use of these samples for the specific research purpose only. The tumor sample used for constructing the DLBCL xenograft was obtained from a 53-year-old man with a past history of Stage I diffuse large B-cell lymphoma 10 years earlier and was treated with CHOP (cyclophosphamide, doxorubicin, vincristine, prednisolone) chemotherapy with complete remission. He presented to the hospital with relapsed disease in the bone marrow, leptomeninges and pleural effusions. He was treated with two courses of RICE (rituximab, ifosfamide, carboplatin, etoposide) and intrathecal methotrexate/cytarabine, then four courses of DHAP (dexamethasone, cytarabine, cisplatin) and intrathecal methotrexate but disease continued to progress and the patient died a year after disease relapse. Cytological examination of the pleural fluid showed discohesive lymphomatous population featuring large cells with vesicular chromatin and conspicuous nucleoli. Neoplastic cells expressed pan-B markers (PAX5, CD20, CD22, CD79a), with aberrant expression of CD5, strong expression of bc12 and a high proliferation fraction of 70-80%. Neoplastic lymphocytes display a non-germinal center phenotype (CD10−, bcl6+, MUM1+, FOXP1+) but staining for c-myc was low at 20%. Interphase fluorescence in situ hybridization showed gains of BCL2 and rearrangements of BCL6 and IGH genes, whereas normal patterns were seen for C-MYC.

Xenograft Construction and Treatment:

The pleural fluid was collected in cold sterile 20% RPMI 1640 medium. Neoplastic cells in the pleural fluid were isolated with FICOLL-PAQUE® PLUS (GE Healthcare, OH), and subsequently resuspended in RPMI 160 medium (Life Technologies, CA) with 20% Fetal Bovine Serum (Life Technologies, CA). A representative part of the tumor sample was fixed in 10% Neutral Buffered Formalin and the other part was utilized for xenotransplantation. The cell suspension was then implanted subcutaneously to four- to six-week-old NOD scid mice. The tumors were monitored periodically and allowed to establish and grow to a maximum of 1000 $mm^3$. The mice were then sacrificed, tumors were harvested and general necropsy was performed. Xenograft tumors were immediately fresh-frozen, formalin-fixed, stored in 90% FBS and 10% DMSO or placed in RPMI 160 medium.

This process was repeated to produce subsequent generations of PDX models (P2, P3, P4, . . . ). To evaluate the maintenance of the morphology and main characteristics of the tumor of origin, formalin-fixed, paraffin-embedded (FFPE) tissues sections from patient tumor samples and xenografts of all established patient-derived xenograft models were stained with hematoxylin and eosin (H&E). In addition these sections were also immunostained to determine the expression of various markers. All these slides were individually observed and reviewed by a clinical pathologist.

For the current study, tumor fragments (approximately 50 mg, P4) were implanted subcutaneously onto the flank of female NOD scid (four- to six-week-old) mice. Tumors were allowed to grow for about 150-250 $mm^3$. The animals were randomized into two different groups (n=5) as mentioned below: Group I, Scrambled Vivo-Morpholinos (GeneTools, Inc.) (Dose 25 μL, intratumorally); Group II, exon 6 targeting Vivo-Morpholinos (GeneTools, Inc.) (Dose 25 μL, intratumorally). Animals were monitored regularly and body weight was measured every day during the treatment period. At the end of the treatment period all the animals were sacrificed, tumors were removed, weighed and observed for gross pathology. Each piece was then divided into two parts. One piece of the tumor was fixed in 10% NBF for 24 hours at room temperature and was then paraffin embedded. The other piece was snap frozen for RNA and protein analysis.

Immunohistochemistry

For immunohistochemical analysis tumors were dissected, fixed for 48 hours in 4% PFA and then processed for paraffin embedding (Thermo Scientific Excelsior™ AS Tissue Processor and HistoStar™ Embedding Workstation). Samples were then sectioned at 5 μm, mounted on Superfrost™ Plus Adhesion Slides (Thermo Scientific) and immunostained for MDM4 (1/1250, Bethyl Laboratories, IHC-00108, rabbit polyclonal), KI67 (1/200, Thermo Scientific #RM-9106-S, clone SP6, rabbit monoclonal) and Cleaved CASPASE-3 (1/300, Cell Signaling Technology, Asp175, rabbit polyclonal) as briefly detailed below. Slides for immunohistochemistry were deparaffinized in xylene and then rehydrated in ethanol series (100%, 95%, and 70%) and distilled $H_2O$. Inhibition of endogenous peroxidase was achieved incubating the slides in 3% $H_2O_2$ for 15 minutes at RT. Epitope retrieval was performed in citrate buffer (pH6) using 2100 Retriever. Sections were blocked in 1% BSA solution for 40 minutes at RT and then incubated overnight at +4° C. with the primary antibody. For both the primary antibodies raised in rabbit, the EnVision+/HRP reagent (Dako K400311) was then applied on sections for 45 minutes at RT. Immunoreactivity was finally revealed via diaminobenzidinechromogen reaction (Peroxidase substrate kit, DAB, SK-4100; Vector Lab). Next, slides were counterstained in hematoxylin (Diapath #C0302), dehydrated in ethanol series, cleared in xylene, and permanently mounted with a resinous mounting medium (MicromountDiapath, #60200). A 0.1% TWEEN® 20 TBS solution was used as washing buffer in between steps.

To assess proliferative and apoptotic indexes, Ki67 or cleaved CASPASE-3 positive and negative nuclei were counted in three microscopic fields randomly selected from different regions of each tumor section applying a digital image analysis algorithm created on the ImageJ software platform. Proliferative and apoptotic indexes were then expressed as the ratio between positive and total number of nuclei.

Viability & Apoptosis Assays

CELLTITER-GLO® kit (Promega) or CELLTITER 96® Aqueous One Solution Cell Proliferation Assay (Promega) were used as cell viability assays. Cells were trypsinized, counted and seeded (5000 cells/well) in clear flat bottom 96-well plates (Corning). After 48/72 hours, cells were incubated with CELLTITER-GLO® or CELLTITER 96® Aqueous One Solution as described in the manufacturer protocol. After 1 hour, the luminescence/absorbance were read with Tecan Safire2 microplate reader.

Caspase-Glo 3/7 Assay kit (Promega) was used as apoptosis assay. Cells were trypsinized, counted and seeded (5000 cells/well) in opaque flat bottom 96-well plates (Corning). After 48/72 hours, cells were incubated with Caspase-Glo 3/7 Assay as described in the manufacturer protocol. After 1 hour, the luminescence/absorbance were read with Tecan Safire2 microplate reader.

Bioinformatics

Calculation of Relative Exon Usage

From the table with raw exon-exon junction counts of MDM4 (ENST00000367182.3) (=j), the total junction expression value per sample (sum of all junctions) (=JG) was calculated. All sample with a JG<(0.05*Max(JG)) were discarded. The remaining samples were normalized (j<=j/JG) (Total junction count per gene=1) and the mean of each junction over all samples calculated and normalized to the most abundant exon-exon junction (exon 10-exon 11 junction). From the 375 original samples downloaded from TCGA using Firehose (gdac.broadinstitute.org/), 90 samples had no count for both exon 5-exon 6 junction and exon 5-exon 7 junction and were excluded from the analysis.

Calculation of the PSI Index in Cancer Tissue Samples

Junction count data and gene mutation status information was downloaded from TCGA using Firehose (gdac.broad-institute.org/) for the different tumor types from the 2014_09_02 data freeze. For each sample the PSI index was calculated based on the Firehose quantified junction counts. Samples where both the short and long form junction fall in the lowest 10% quantile for each junction were excluded. The PSI of the counts of the MDM4-FL junction (from chr1:204501374:+ to chr1:204506558:+) and the MDM4-S junction (from chr1:204501374:+ to chr1:204507337:+) were calculated, sorted and plotted.

Analysis of RNA binding sites near MDM4 in mouse Processed reads from CLIP-seq and HITS were downloaded from starBase (starbase.sysu.edu.cn). Raw reads for SRSF3/4 were downloaded from ArrayExpress database (ebi.ac.uk/arrayexpress/) under the accession number E-MTAB-747 and mapped to the $mm^9$ genome using Bowtie (bowtie-bio.sourceforge.net/index.shtml). The $mm^9$ genomic region surrounding exon 7-8 of MDM4 was visualized using the R environment (cran.r-project.org/).

RNA Immunoprecipitation (RIP)

A375 cells (three 15 cm plates at 80% confluence) were washed in PBS and trypsinized for 5 minutes. The reaction was stopped by adding PBS+5% FBS and pelleted at 1500 rpm for 5 minutes at 4° C. The cell pellet was washed twice in ice-cold PBS. The pellet was then resuspended in 1.8 µl of Lysis buffer (Tris buffer 50 mM pH 8, NaCl 150 mM, NP40 0.5%, Sodium Deoxycholate 0.5%, SDS 0.005%, freshly added SUPERase In RNase Inhibitor (Ambion) 1:200 and Protease inhibitor cocktail (Calbiochem, #539134) 1:1000). The lysate was placed in ice for 20 minutes, followed by sonication in a Diagenode BioRuptor UCD-200 (3 strokes 30 seconds each, 30-second pause interval). The lysates were cleared by centrifugation for 10 minutes at 14000 rpm at 4° C., and the total protein content of the lysates was determined using the Bradford method (Thermo Scientific). A portion of the lysate (10%) was saved for the input sample. The remaining lysate was precleared with protein A DYNABEADS® (Invitrogen) at 4° C. for 1 hour with rotation. The beads were always washed, prior to use, three times in washing buffer (Trish HCl buffer 200 mM pH 8, NaCl 100 mM, NP40 0.5%, freshly added SUPERase In™ RNase Inhibitor 1:200 and Protease inhibitor cocktail 1:1000). The lysate was separated from the beads and added to 60 µl of washed DYNABEADS® (50% slurry) pre-incubated with 5 µg of SRSF3 antibody for 1 hour at room temperature. After 3 hours rotation at 4° C., the antibody-bound beads were washed three times with washing buffer. The RNA was extracted with 1 ml of TRIZOL®, adding 0.35 µl of GlycoBlue Coprecipitant (Thermo Fisher, #AM9516) in each RNA precipitation step. RNA restrotran-scription was performed using SUPERSCRIPT® VILO cDNA synthesis kit (Thermo Fisher, #11754050) following manufacturer protocol. MDM4 Exon 6 splicing regulatory element was detected in the immunoprecipitated RNA by real time RT-PCR using the primers indicated in Table 7.

Statistics

An unpaired t-test was used to assess statistical difference in FIG. 3A (statistical significance determined using the Holm-Sidak method, with alpha=5.000%). A paired t-test was used to assess statistical difference. Two-tailed P-values of <0.05 were considered significant. Two-way ANOVA® was used to determine statistical significance; (*) $P<0.05$; () $P<0.01$; (*) $P<0.001$.

TABLE 1

PDX xenopatient information

| Xenopatient | MEL002 | MEL006 | MEL010 | BCL13 |
|---|---|---|---|---|
| Gender | Female | Female | Female | Male |
| Year of birth | 1931 | 1947 | 1955 | 1962 |
| Melanoma Stage | In transit metastasis | in transit metastasis | Lymph node | n.a. |
| Biopt location | Upper leg | Arm | Chest | Pleural effusion |
| Treatment prior to biopt | Dacarbazine | Surgery; ipilimumab; dabrafenib-trametinib | Surgery; dabrafenib-trametinib | CHOP; RICE; DHAP; intrathecal methotrexate |
| BRAF V600 status | WT | V600E | V600E | — |
| NRAS Q61 status | WT | WT | WT | — |
| p53 status | WT (SNP c.215C>G; p.P72R) | WT (SNP c.215C>G; p.P72R) | WT (SNP c.215C>G; p.P72R) | HET (c.907G>G/C (WT/missense) |

TABLE 2

Antibodies

| Protein | Reactive species | Company | Clone/Catalog number | Working concentration |
|---|---|---|---|---|
| MDM4 | Human | Millipore | 8C6 | 1:1000 |
| Mdm4 | Mouse | Sigma-Aldrich | MDMX-82 | 1:1000 |
| MDM2 | Human | Homemade mAb + Santa Cruz Biotechnology | 4B2 (Homemade) and SMP14, sc-965 | 1:1000 |
| p53 | Human | Santa Cruz Biotechnology | DO-1, sc-126 | 1:5000 |
| p21 | Human | Santa Cruz Biotechnology | F-5, sc-6246 | 1:500 |
| SRSF3 | Human | Abcam | Ab125124 | 1:500 |
| ACTIN/Actin | Human/Mouse | Sigma-Aldrich/Santa Cruz Biotechnology | A2066/C4 | 1:10000/1:1000 |
| b-TUBULIN | Human | Sigma-Aldrich | T5168 | 1:10000 |
| GAPDH | Human/Mouse | Abcam | Ab9485 | 1:1000 |

TABLE 3

Primers

SybrGreen-based RT-qPCR

| | Gene | Forward | Reverse |
|---|---|---|---|
| Human | Total MDM4 | AGGTGCGCAAGGTGAAATGT (SEQ ID NO: 1) | CCATATGCTGCTCCTGCTGAT (SEQ ID NO: 2) |
| | MDM4-FL | GATGCTGCTCAGACTCTCGC (SEQ ID NO: 3) | TGCACTTTGCTTCAGTTGGTC (SEQ ID NO: 4) |
| | MDM4-S | GCCACTGCTACTACAGCAAA G (SEQ ID NO: 5) | TCTGAGGTAGGCAGTGTGGG (SEQ ID NO: 6) |

TABLE 3-continued

Primers

|  | Gene | Forward | Reverse |
|---|---|---|---|
|  | MDM2 | AGGAGATTTGTTTGGCGTGC (SEQ ID NO: 7) | TGAGTCCGATGATTCCTGCTG (SEQ ID NO: 8) |
|  | p21 | GGCCTGGACTGTTTTCTCTC G (SEQ ID NO: 9) | GAGAAACGGGAACCAGGACAC (SEQ ID NO: 10) |
|  | BBC3 | GACCTCAACGCACAGTA (SEQ ID NO: 11) | CTAATTGGGCTCCATCT (SEQ ID NO: 12) |
|  | SRSF1 | TGGTTGTCTCTGGACTGCCT (SEQ ID NO: 13) | ACACCAGTGCCATCTCGGTA (SEQ ID NO: 14) |
|  | SRSF2 | CGGAGCCGCAGCCCTA (SEQ ID NO: 15) | AGATCGAGAACGAGTGCGG (SEQ ID NO: 16) |
|  | SRSF3 | AGCTGATGCAGTCCGAGAG (SEQ ID NO: 17) | GGTGGGCCACGATTTCTAC (SEQ ID NO: 18) |
|  | SRSF4 | TCTGAAGAACGGATATGGTTTTGTG (SEQ ID NO: 19) | CTCGCTCACCACAAAGGTCT (SEQ ID NO: 20) |
|  | CENPF | CTCTCCCGTCAACAGCGTTC (SEQ ID NO: 21) | GTTGTGCATATTCTTGCTTGC (SEQ ID NO: 22) |
|  | KIF23 | TGCTGCCATGAAGTCAGCGA GAG (SEQ ID NO: 23) | CCAGTGGGCGCACCCTACAG (SEQ ID NO: 24) |
|  | MAD2L1 | AAGTGGTGAGGTCCTGGAAA (SEQ ID NO: 25) | TTCCAACAGTGGCAGAAATG (SEQ ID NO: 26) |
|  | TBP (RefGen) | AATCTGTCATGCTGGTCTGCC (SEQ ID NO: 27) | AGGAGATTTGTTTGGCGTGC (SEQ ID NO: 28) |
|  | UBC (RefGen) | ATTTGGGTCGCGGTTCTTG (SEQ ID NO: 29) | TGCCTTGACATTCTCGATGGT (SEQ ID NO: 30) |
|  | YWHAZ (RefGen) | ACTTTTGGTACATTGTGGCTT CAA (SEQ ID NO: 31) | CCGCCAGGACAAACCAGTAT (SEQ ID NO: 32) |
| Mouse | total Mdm4 | GACCGACTGAAGCACGGTGC AA (SEQ ID NO: 33) | ACCAAGGCAGGCCAGCAACG (SEQ ID NO: 34) |
|  | Mdm4-FL | TTCTGTGAAAGATCCAAGCCC T (SEQ ID NO: 35) | AGTCTGAGCAGCATCTGTGTT A (SEQ ID NO: 36) |
|  | Mdm4-S | TGTGAAAGATCCAAGCCCTCT (SEQ ID NO: 37) | TGTTGCACCGTGCTGTGTTA (SEQ ID NO: 38) |
|  | Eif3f (RefGen) | GAACCCCATTCACCTCACGG (SEQ ID NO: 39) | GAGGTCAACTCCAATGCGTTC (SEQ ID NO: 40) |
|  | Heatr3 (RefGen) | ACTCTTGCTCAGCACCTGTC (SEQ ID NO: 41) | TCAGGGGTCATACACTGTGG (SEQ ID NO: 42) |
|  | Psmd4 (RefGen) | GGAGGCAAGATGGTGTTGGA (SEQ ID NO: 43) | ACAGTCATTGGCCAGTGTGA (SEQ ID NO: 44) | semi-qPCR

|  | Gene | Forward | Reverse |
|---|---|---|---|
| Human | MDM4 splice status | TGTGGTGGAGATCTTTTGGG (SEQ ID NO: 45) | GCAGTGTGGGGATATCGT (SEQ ID NO: 46) |
|  | GAPDH | TGCCATGTAGACCCCTTGAAG (SEQ ID NO: 47) | ATGGTACATGACAAGGTGCGG (SEQ ID NO: 48) |
| Mouse | MDM4 splice status | TGTGGTGGAGATCTTTTGGG (SEQ ID NO: 49) | TCAGTTCTTTTTCTGGGATTGG (SEQ ID NO: 50) |
|  | Gapdh | AGGTTGTCTCCTGCGACTTCA (SEQ ID NO: 51) | GGTGGTCCAGGGTTTCTTACTC (SEQ ID NO: 52) |

TABLE 4 shRNA from MISSION pLKO1 shRNA library

| TRC code | SHORT CODE | Target gene |
|---|---|---|
| TRCN0000001227 | 227 | SRSF3 |
| TRCN0000273171 | 171 | SRSF3 |
| TRCN0000273170 | 170 | SRSF3 |
| TRCN0000001224 | 224 | SRSF3 |
| TRCN0000273174 | 174 | SRSF3 |
| TRCN0000231449 | 449 | SRSF4 |
| TRCN0000231448 | 448 | SRSF4 |
| TRCN0000001095 | 95 | SRSF1 |
| TRCN0000001096 | 96 | SRSF1 |
| TRCN0000000109 | 109 | SRSF2 |
| TRCN0000000084 | 84 | SRSF2 |
| TRCN0000000140 | 140 | SRSF5 |
| TRCN0000000141 | 141 | SRSF5 |
| TRCN0000231443 | 443 | SRSF6 |
| TRCN0000006620 | 620 | SRSF6 |
| TRCN0000001142 | 142 | SRSF7 |
| TRCN0000273401 | 401 | SRSF7 |
| TRCN0000320890 | 890 | SRSF9 |
| TRCN0000320892 | 892 | SRSF9 |
| TRCN0000074835 | 835 | SRSF10 |
| TRCN0000074836 | 836 | SRSF10 |
| TRCN0000284895 | 895 | SRSF11 |
| TRCN0000314691 | 691 | SRSF11 |
| TRCN0000001309 | 309 | SRSF12 |
| TRCN0000001307 | 307 | SRSF12 |

TABLE 5

Morpholino and ASO sequences

| | |
|---|---|
| Morpholino Scramble | CGGTGTGTGTATCATTCTAGTGT (SEQ ID NO: 53) |
| Morpholino MDM4 | CGTGTGGTGATTTTACCTTCAGTTG (SEQ ID NO: 54) |
| Scramble ASO | TTGCACGAGTGCAAAAGGTCTTCAT (SEQ ID NO: 55) |
| ASO1 | GCGAGAGTCTGAGCAGCATCTGGAT (SEQ ID NO: 56) |
| ASO2 | ATATCCATACTGTGATCCTGTGCGA (SEQ ID NO: 57) |
| ASO3 | TACCTTCAGTTGGTCTTGACTTGGA (SEQ ID NO: 58) |
| ASO5 | ACCGTGTGGTGATTTTACCTTCAGT (SEQ ID NO: 59) |
| ASO4 | CGTGTGGTGATTTTACCTTCAGTTG (SEQ ID NO: 60) |

TABLE 6

TAQMAN® qPCR and probes

| | |
|---|---|
| Forward primer | AAGAAAGAATCTTGTCACTTTAGCC (SEQ ID NO: 61) |
| Reverse primer | GGGATATCGTCTTCTGTAGTTCTT (SEQ ID NO: 62) |
| Exon 5-7 (MDM4-S)- 5'6-FAM™-ZEN-3' Iowa Black® FQ | ACTGCTACTACAGCAAAGTGCAGAGG (SEQ ID NO: 63) |

TABLE 6-continued

TAQMAN ® qPCR and probes

| | | |
|---|---|---|
| Exon 6-7 (MDM4-FL)-<br>5'TET™-ZEN-3'<br>Iowa Black ® FQ | CACTTTGCTTCAGTTGGTCTTGACTTGG<br>(SEQ ID NO: 64) | |

TABLE 7

RIP primers

| | | |
|---|---|---|
| Upstream MDM4 exon 6 | GATATGGCCTGTCTTGGTC TT (SEQ ID NO: 65) | GCCAGGTTTAGTCCCTAG A AAT (SEQ ID NO: 66) |
| Predicted SRSF3 binding site on 5'SS of MDM4 exon 6 | AGTCAAGACCAACTGAAG GTAAA (SEQ ID NO: 67) | TCCAAGATCCATAGGTAC A GAGA (SEQ ID NO: 68) |
| SRSF3 exon 4 (positive control) | CGCCAACCAACTAAATCC AAC (SEQ ID NO: 69) | AAGCTAGAAATGGTGAG GT GAG (SEQ ID NO: 70) |

REFERENCES

1. Marine, J. C., and Jochemsen, A. G. 2005. Mdmx as an essential regulator of p53 activity. *Biochemical and Biophysical Research Sommunications* 331:750-760.
2. De Clercq, S., Gembarska, A., Denecker, G., Maetens, M., Naessens, M., Haigh, K., Haigh, J. J., and Marine, J. C. 2010. Widespread overexpression of epitope-tagged Mdm4 does not accelerate tumor formation in vivo. *Molecular and Cellular Biology* 30:5394-5405.
3. Maetens, M., Doumont, G., Clercq, S. D., Francoz, S., Froment, P., Bellefroid, E., Klingmuller, U., Lozano, G., and Marine, J. C. 2007. Distinct roles of Mdm2 and Mdm4 in red cell production. *Blood* 109:2630-2633.
4. Boesten, L. S., Zadelaar, S. M., De Clercq, S., Francoz, S., van Nieuwkoop, A., Biessen, E. A., Hofmann, F., Feil, S., Feil, R., Jochemsen, A. G., et al. 2006. Mdm2, but not Mdm4, protects terminally differentiated smooth muscle cells from p53-mediated caspase-3-independent cell death. *Cell Death and Differentiation* 13:2089-2098.
5. Xiong, S., Van Pelt, C. S., Elizondo-Fraire, A. C., Liu, G., and Lozano, G. 2006. Synergistic roles of Mdm2 and Mdm4 for p53 inhibition in central nervous system development. *Proceedings of the National Academy of Sciences of the United States of America* 103:3226-3231.
6. Garcia, D., Warr, M. R., Martins, C. P., Brown Swigart, L., Passegue, E., and Evan, G. I. 2011. Validation of MdmX as a therapeutic target for reactivating p53 in tumors. *Genes and Development* 25:1746-1757.
Valentin-Vega, Y. A., Box, N., Terzian, T., and Lozano, G. 2009. Mdm4 loss in the intestinal epithelium leads to compartmentalized cell death but no tissue abnormalities. *Differentiation; Research in Biological Diversity* 77:442-449.
8. Yan, H., Solozobova, V., Zhang, P., Armant, O., Kuehl, B., Brenner-Weiss, G., and Blattner, C. 2015. p53 is active in murine stem cells and alters the transcriptome in a manner that is reminiscent of mutant p53. *Cell Death and Disease* 6:e1662.
9. Danovi, D., Meulmeester, E., Pasini, D., Migliorini, D., Capra, M., Frenk, R., de Graaf, P., Francoz, S., Gasparini, P., Gobbi, A., et al. 2004. Amplification of Mdmx (or Mdm4) directly contributes to tumor formation by inhibiting p53 tumor suppressor activity. *Molecular and Cellular Biology* 24:5835-5843.
10. Toledo, F., and Wahl, G. M. 2006. Regulating the p53 pathway: in vitro hypotheses, in vivo veritas. *Nature Reviews: Cancer* 6:909-923.
11. Wade, M., Li, Y. C., and Wahl, G. M. 2013. MDM2, MDMX and p53 in oncogenesis and cancer therapy. *Nature Reviews: Cancer* 13:83-96.
12. Marine, J. C. 2011. MDM2 and MDMX in cancer and development. *Current Topics in Developmental Biology* 94:45-75.
13. Gembarska, A., Luciani, F., Fedele, C., Russell, E. A., Dewaele, M., Villar, S., Zwolinska, A., Haupt, S., de Lange, J., Yip, D., et al. 2012. MDM4 is a key therapeutic target in cutaneous melanoma. *Nature Medicine*.
14. Flaherty, K. T., Puzanov, I., Kim, K. B., Ribas, A., McArthur, G. A., Sosman, J. A., O'Dwyer, P. J., Lee, R. J., Grippo, J. F., Nolop, K., et al. 2010. Inhibition of mutated, activated BRAF in metastatic melanoma. *The New England Journal of Medicine* 363:809-819.
15. Chapman, P. B., Hauschild, A., Robert, C., Haanen, J. B., Ascierto, P., Larkin, J., Dummer, R., Garbe, C., Testori, A., Maio, M., et al. 2011. Improved survival with vemurafenib in melanoma with BRAF V600E mutation. *The New England Journal of Medicine* 364:2507-2516.
16. Nazarian, R., Shi, H., Wang, Q., Kong, X., Koya, R. C., Lee, H., Chen, Z., Lee, M. K., Attar, N., Sazegar, H., et al. 2010. Melanomas acquire resistance to B-RAF(V600E) inhibition by RTK or NRAS upregulation. *Nature* 468:973-977.
17. Azijli, K., Stelloo, E., Peters, G. J., and A J, V. D. E. 2014. New developments in the treatment of metastatic melanoma: immune checkpoint inhibitors and targeted therapies. *Anticancer Research* 34:1493-1505.
18. Carrillo, A. M., Bouska, A., Arrate, M. P., and Eischen, C. M. 2014. Mdmx promotes genomic instability independent of p53 and Mdm2. *Oncogene*.
19. Matijasevic, Z., Krzywicka-Racka, A., Sluder, G., and Jones, S. N. 2008. MdmX regulates transformation and chromosomal stability in p53-deficient cells. *Cell Cycle* 7:2967-2973.
20. Matijasevic, Z., Steinman, H. A., Hoover, K., and Jones, S. N. 2008. MdmX promotes bipolar mitosis to suppress transformation and tumorigenesis in p53-deficient cells and mice. *Molecular and Cellular Biology* 28:1265-1273.
21. de Lange, J., Teunisse, A. F., Vries, M. V., Lodder, K., Lam, S., Luyten, G. P., Bernal, F., Jager, M. J., and Jochemsen, A. G. 2012. High levels of Hdmx promote cell growth in a subset of uveal melanomas. *American Journal of Cancer Research* 2:492-507.
22. Kornblihtt, A. R., Schor, I. E., Allo, M., Dujardin, G., Petrillo, E., and Munoz, M. J. 2013. Alternative splicing: a pivotal step between eukaryotic transcription and translation. Nature reviews. *Molecular Cell Biology* 14:153-165.

23. Perez-Ortin, J. E., Alepuz, P., Chavez, S., and Choder, M. 2013. Eukaryotic mRNA decay: methodologies, pathways, and links to other stages of gene expression. *Journal of Molecular Biology* 425:3750-3775.
24. Boutz, P. L., Bhutkar, A., and Sharp, P. A. 2015. Detained introns are a novel, widespread class of post-transcriptionally spliced introns. *Genes and Development* 29:63-80.
25. Rallapalli, R., Strachan, G., Cho, B., Mercer, W. E., and Hall, D. J. 1999. A novel MDMX transcript expressed in a variety of transformed cell lines encodes a truncated protein with potent p53 repressive activity. *The Journal of Biological Chemistry* 274:8299-8308.
26. Bezzi, M., Teo, S. X., Muller, J., Mok, W. C., Sahu, S. K., Vardy, L. A., Bonday, Z. Q., and Guccione, E. 2013. Regulation of constitutive and alternative splicing by PRMT5 reveals a role for Mdm4 premRNA in sensing defects in the spliceosomal machinery. *Genes and Development* 27:1903-1916.
27. Bardot, B., Bouarich-Bourimi, R., Leemput, J., Lejour, V., Hamon, A., Plancke, L., Jochemsen, A. G., Simeonova, I., Fang, M., and Toledo, F. 2014. Mice engineered for an obligatory Mdm4 exon skipping express higher levels of the Mdm4-S isoform but exhibit increased p53 activity. *Oncogene*.
28. Kato, S., Han, S. Y., Liu, W., Otsuka, K., Shibata, H., Kanamaru, R., and Ishioka, C. 2003. Understanding the function-structure and function-mutation relationships of p53 tumor suppressor protein by high-resolution missense mutation analysis. *Proceedings of the National Academy of Sciences of the United States of America* 100:8424-8429.
29. Lenos, K., Grawenda, A. M., Lodder, K., Kuijjer, M. L., Teunisse, A. F., Repapi, E., Grochola, L. F., Bartel, F., Hogendoorn, P. C., Wuerl, P., et al. 2012. Alternate splicing of the p53 inhibitor HDMX offers a superior prognostic biomarker than p53 mutation in human cancer. *Cancer Research* 72:4074-4084.
30. Anko, M. L., Muller-McNicoll, M., Brandi, H., Curk, T., Gorup, C., Henry, I., Ule, J., and Neugebauer, K. M. 2012. The RNA-binding landscapes of two SR proteins reveal unique functions and binding to diverse RNA classes. *Genome Biology* 13:R17.
31. Pandit, S., Zhou, Y., Shiue, L., Coutinho-Mansfield, G., Li, H., Qiu, J., Huang, J., Yeo, G. W., Ares, M., Jr., and Fu, X. D. 2013. Genome-wide analysis reveals SR protein cooperation and competition in regulated splicing. *Molecular Cell* 50:223-235.
32. Charizanis, K., Lee, K. Y., Batra, R., Goodwin, M., Zhang, C., Yuan, Y., Shiue, L., Cline, M., Scotti, M. M., Xia, G., et al. 2012. Muscleblind-like 2-mediated alternative splicing in the developing brain and dysregulation in myotonic dystrophy. *Neuron* 75:437-450.
33. Liu, Y., Hu, W., Murakawa, Y., Yin, J., Wang, G., Landthaler, M., and Yan, J. 2013. Cold-induced RNA-binding proteins regulate circadian gene expression by controlling alternative polyadenylation. *Scientific Reports* 3:2054.
34. Wang, E. T., Cody, N. A., Jog, S., Biancolella, M., Wang, T. T., Treacy, D. J., Luo, S., Schroth, G. P., Housman, D. E., Reddy, S., et al. 2012. Transcriptome-wide regulation of pre-mRNA splicing and mRNA localization by muscleblind proteins. *Cell* 150:710-724.
35. Zhang, C., and Darnell, R. B. 2011. Mapping in vivo protein-RNA interactions at single-nucleotide resolution from HITS-CLIP data. *Nature Biotechnology* 29:607-614.
36. Corbo, C., Orru, S., and Salvatore, F. 2013. SRp20: an overview of its role in human diseases. *Biochemical and Biophysical Research Communications* 436:1-5.
37. Muraki, M., Ohkawara, B., Hosoya, T., Onogi, H., Koizumi, J., Koizumi, T., Sumi, K., Yomoda, J., Murray, M. V., Kimura, H., et al. 2004. Manipulation of alternative splicing by a newly developed inhibitor of Clks. *The Journal of Biological Chemistry* 279:24246-24254.
38. Yadav, V., Zhang, X., Liu, J., Estrem, S., Li, S., Gong, X. Q., Buchanan, S., Henry, J. R., Starling, J. J., and Peng, S. B. 2012. Reactivation of mitogen-activated protein kinase (MAPK) pathway by FGF receptor 3 (FGFR3)/Ras mediates resistance to vemurafenib in human B-RAF V600E mutant melanoma. *The Journal of Biological Chemistry* 287:28087-28098.
39. Raal, F. J., Santos, R. D., Blom, D. J., Marais, A. D., Charng, M. J., Cromwell, W. C., Lachmann, R. H., Gaudet, D., Tan, J. L., Chasan-Taber, S., et al. 2010. Mipomersen, an apolipoprotein B synthesis inhibitor, for lowering of LDL cholesterol concentrations in patients with homozygous familial hypercholesterolaemia: a randomised, double-blind, placebo-controlled trial. *Lancet* 375:998-1006.
40. Heemskerk, H. A., de Winter, C. L., de Kimpe, S. J., van Kuik-Romeijn, P., Heuvelmans, N., Platenburg, G. J., van Ommen, G. J., van Deutekom, J. C., and Aartsma-Rus, A. 2009. In vivo comparison of 2'-O-methyl phosphorothioate and morpholino antisense oligonucleotides for Duchenne muscular dystrophy exon skipping. *The Journal of Gene Medicine* 11:257-266.
41. Livingstone, E., Zimmer, L., Vaubel, J., and Schadendorf, D. 2014. BRAF, MEK and KIT inhibitors for melanoma: adverse events and their management. *Chinese Clinical Oncology* 3:29.
42. Lam, S., Lodder, K., Teunisse, A. F., Rabelink, M. J., Schutte, M., and Jochemsen, A. G. 2010. Role of Mdm4 in drug sensitivity of breast cancer cells. *Oncogene* 29:2415-2426.
43. Shi, M., Wang, S., Yao, Y., Li, Y., Zhang, H., Han, F., Nie, H., Su, J., Wang, Z., Yue, L., et al. 2014. Biological and clinical significance of epigenetic silencing of MARVELD1 gene in lung cancer. *Scientific Reports* 4:7545.
44. Wang, D., Wengrod, J., and Gardner, L. B. 2011. Overexpression of the c-myc oncogene inhibits nonsense-mediated RNA decay in B lymphocytes. *The Journal of Biological Chemistry* 286:40038-40043.
45. Lenos, K., and Jochemsen, A. G. 2011. Functions of MDMX in the modulation of the p53-response. *Journal of Biomedicine and Biotechnology* 2011:876173.
46. Zhou, Z., and Fu, X. D. 2013. Regulation of splicing by SR proteins and SR protein-specific kinases. *Chromosoma* 122:191-207.
47. Jia, R., Li, C., McCoy, J. P., Deng, C. X., and Zheng, Z. M. 2010. SRp20 is a proto-oncogene critical for cell proliferation and tumor induction and maintenance. *International Journal of Biological Sciences* 6:806-826.
48. Goncalves, V., Matos, P., and Jordan, P. 2008. The beta-catenin/TCF4 pathway modifies alternative splicing through modulation of SRp20 expression. *RNA* 14:2538-2549.
49. Coombs, G. S., Covey, T. M., and Virshup, D. M. 2008. Wnt signaling in development, disease and translational medicine. *Current Drug Targets* 9:513-531.
50. Wang, Z., Chatterjee, D., Jeon, H. Y., Akerman, M., Vander Heiden, M. G., Cantley, L. C., and Krainer, A. R. 2012. Exon-centric regulation of pyruvate kinase M alternative splicing via mutually exclusive exons. *Journal of molecular cell biology* 4:79-87.
51. Tang, Y., Horikawa, I., Ajiro, M., Robles, A. I., Fujita, K., Mondal, A. M., Stauffer, J. K., Zheng, Z. M., and Harris, C. C. 2013. Downregulation of splicing factor SRSF3 induces p53beta, an alternatively spliced isoform of p53 that promotes cellular senescence. *Oncogene* 32:2792-2798.
52. Hair, P., Cameron, F., and McKeage, K. 2013. Mipomersen sodium: first global approval. *Drugs* 73:487-493.

The invention claimed is:

1. A method of treating a subject having a tumor with an inhibitor of MDM4, the method comprising:
   determining, in the tumor, or in a sample from the tumor, that the ratio of MDM4 full-length RNA transcript to MDM4 transcript lacking exon 6 is higher than 1; and
   administering the inhibitor of MDM4 to the subject;
   wherein the inhibitor of MDM4 induces exon 6 skipping in MDM4 mRNA.

2. The method according to claim 1, wherein the inhibitor acts at the RNA level.

3. The method according to claim 1, wherein the inhibitor is an antisense oligonucleotide.

4. The method according to claim 1,
   wherein the inhibitor of MDM4 is an antisense oligonucleotide selected from the group consisting of
   an antisense oligonucleotide which binds to the exon-intron boundary of exon 6 of MDM4 and overlaps at least one Ser-Arg Splicing Factor 3 (SRSF3) binding site;
   an antisense oligonucleotide which targets the 5' donor site of the intron downstream of human MDM4 exon 6 and the adjacent downstream SRSF3 binding site;
   an antisense oligonucleotide comprising the nucleotide sequence of SEQ ID NO: 54; and
   an antisense oligonucleotide comprising the nucleotide sequence of SEQ ID NO: 60; and
   wherein the antisense oligonucleotide is a morpholino or a gapmer antisense oligonucleotide.

5. The method according to claim 1, wherein the tumor is selected from the group consisting of stomach cancer, intestine cancer, glioblastoma, colorectal cancer, breast cancer, lung cancer, prostate cancer, osteosarcoma, retinoblastoma, melanoma, testis cancer, larynx cancer, uterus cancer, neuroblastoma, ovarian cancer, head and neck squamous cell carcinoma, and diffuse large B cell lymphoma.

6. The method according to claim 1, wherein the inhibitor of MDM4 is selected from the group consisting of a pharmacological or genetic inactivator of SRSF3, a short hairpin RNA (shRNA) silencer of SRSF3, meayamycin, a PRMT5 inhibitor, and a SmB inhibitor.

7. The method according to claim 1 further comprising administering a chemotherapeutic agent or a MAPK-targeting agent to the subject.

8. A method of treating a subject having a tumor with an inhibitor of MDM4, the method comprising:
   determining, in the tumor, or in a sample from the tumor, that the ratio of MDM4 full-length RNA transcript to the sum of MDM4 transcript lacking exon 6 and MDM4 full-length RNA transcript is higher than 0.4; and
   administering the inhibitor of MDM4 to the subject;
   wherein the inhibitor of MDM4 induces exon 6 skipping in MDM4 mRNA.

9. The method according to claim 8, wherein the inhibitor acts at the RNA level.

10. The method according to claim 8, wherein the inhibitor is an antisense oligonucleotide.

11. The method according to claim 8,
   wherein the inhibitor of MDM4 is an antisense oligonucleotide selected from the group consisting of
   an antisense oligonucleotide which binds to the exon-intron boundary of exon 6 of MDM4 and overlaps at least one Ser-Arg Splicing Factor 3 (SRSF3) binding site;
   an antisense oligonucleotide which targets the 5' donor site of the intron downstream of human MDM4 exon 6 and the adjacent downstream SRSF3 binding site;
   an antisense oligonucleotide comprising the nucleotide sequence of SEQ ID NO: 54; and
   an antisense oligonucleotide comprising the nucleotide sequence of SEQ ID NO: 60; and
   wherein the antisense oligonucleotide is a morpholino or a gapmer antisense oligonucleotide.

12. The method of claim 8, wherein the inhibitor of MDM4 is selected from the group consisting of: a pharmacological or genetic inactivator of SRSF3, a short hairpin RNA (shRNA) silencer of SRSF3, meayamycin, a PRMT5 inhibitor, and a SmB inhibitor.

13. The method according to claim 8, wherein the tumor is selected from the group consisting of melanoma, stomach cancer, intestine cancer, glioblastoma, colorectal cancer, breast cancer, lung cancer, prostate cancer, osteosarcoma, retinoblastoma, testis cancer, larynx cancer, uterus cancer, neuroblastoma, ovarian cancer, head and neck squamous cell carcinoma, and diffuse large B cell lymphoma.

14. The method according to claim 8 further comprising administering a chemotherapeutic agent or a MAPK-targeting agent to the subject.

15. A method of treating a patient having a tumor comprising administering to the patient an antisense oligonucleotide directed to MDM4 RNA that induces skipping of exon 6 in MDM4 RNA, thereby inducing skipping of exon 6 in MDM4 RNA in a tumor of the patient.

16. The method according to claim 15,
   wherein the antisense oligonucleotide is selected from the group consisting of an antisense oligonucleotide which binds to the exon-intron boundary of exon 6 of MDM4 and overlaps at least one Ser-Arg Splicing Factor 3 (SRSF3) binding site;
   an antisense oligonucleotide which targets the 5' donor site of the intron downstream of human MDM4 exon 6 and the adjacent downstream SRSF3 binding site;
   an antisense oligonucleotide comprising the nucleotide sequence of SEQ ID NO: 54; and
   an antisense oligonucleotide comprising the nucleotide sequence of SEQ ID NO: 60; and
   wherein the antisense oligonucleotide is a morpholino or a gapmer antisense oligonucleotide.

17. The method according to claim 15, wherein the tumor is selected from the group consisting of melanoma, stomach cancer, intestine cancer, glioblastoma, colorectal cancer, breast cancer, lung cancer, prostate cancer, osteosarcoma, retinoblastoma, testis cancer, larynx cancer, uterus cancer, neuroblastoma, ovarian cancer, head and neck squamous cell carcinoma, and diffuse large B cell lymphoma.

18. The method according to claim 15 further comprising administering a chemotherapeutic agent or a MAPK-targeting agent to the subject.

\* \* \* \* \*

SEQUENCE LISTING

<160> NUMBER OF SEQ ID NOS: 72

<210> SEQ ID NO 1
<211> LENGTH: 20
<212> TYPE: DNA
<213> ORGANISM: artificial
<220> FEATURE:
<223> OTHER INFORMATION: Primer

<400> SEQUENCE: 1
aggtgcgcaa ggtgaaatgt             20

<210> SEQ ID NO 2
<211> LENGTH: 21
<212> TYPE: DNA
<213> ORGANISM: artificial
<220> FEATURE:
<223> OTHER INFORMATION: Primer

<400> SEQUENCE: 2
ccatatgctg ctcctgctga t            21

<210> SEQ ID NO 3
<211> LENGTH: 20
<212> TYPE: DNA
<213> ORGANISM: artificial
<220> FEATURE:
<223> OTHER INFORMATION: Primer

<400> SEQUENCE: 3
gatgctgctc agactctcgc             20

<210> SEQ ID NO 4
<211> LENGTH: 21
<212> TYPE: DNA
<213> ORGANISM: artificial
<220> FEATURE:
<223> OTHER INFORMATION: Primer

<400> SEQUENCE: 4
tgcactttgc ttcagttggt c            21

<210> SEQ ID NO 5
<211> LENGTH: 21
<212> TYPE: DNA
<213> ORGANISM: artificial
<220> FEATURE:
<223> OTHER INFORMATION: Primer

<400> SEQUENCE: 5
gccactgcta ctacagcaaa g            21

<210> SEQ ID NO 6
<211> LENGTH: 20
<212> TYPE: DNA
<213> ORGANISM: artificial
<220> FEATURE:
<223> OTHER INFORMATION: Primer

<400> SEQUENCE: 6
tctgaggtag gcagtgtggg             20

<210> SEQ ID NO 7
<211> LENGTH: 20
<212> TYPE: DNA
<213> ORGANISM: artificial

```
<220> FEATURE:
<223> OTHER INFORMATION: Primer

<400> SEQUENCE: 7
aggagatttg tttggcgtgc                                                    20

<210> SEQ ID NO 8
<211> LENGTH: 21
<212> TYPE: DNA
<213> ORGANISM: artificial
<220> FEATURE:
<223> OTHER INFORMATION: Primer

<400> SEQUENCE: 8
tgagtccgat gattcctgct g                                                  21

<210> SEQ ID NO 9
<211> LENGTH: 21
<212> TYPE: DNA
<213> ORGANISM: artificial
<220> FEATURE:
<223> OTHER INFORMATION: Primer

<400> SEQUENCE: 9
ggcctggact gttttctctc g                                                  21

<210> SEQ ID NO 10
<211> LENGTH: 21
<212> TYPE: DNA
<213> ORGANISM: artificial
<220> FEATURE:
<223> OTHER INFORMATION: Primer

<400> SEQUENCE: 10
gagaaacggg aaccaggaca c                                                  21

<210> SEQ ID NO 11
<211> LENGTH: 17
<212> TYPE: DNA
<213> ORGANISM: artificial
<220> FEATURE:
<223> OTHER INFORMATION: Primer

<400> SEQUENCE: 11
gacctcaacg cacagta                                                       17

<210> SEQ ID NO 12
<211> LENGTH: 17
<212> TYPE: DNA
<213> ORGANISM: artificial
<220> FEATURE:
<223> OTHER INFORMATION: Primer

<400> SEQUENCE: 12
ctaattgggc tccatct                                                       17

<210> SEQ ID NO 13
<211> LENGTH: 20
<212> TYPE: DNA
<213> ORGANISM: artificial
<220> FEATURE:
<223> OTHER INFORMATION: Primer

<400> SEQUENCE: 13
tggttgtctc tggactgcct                                                    20
```

-continued

```
<210> SEQ ID NO 14
<211> LENGTH: 20
<212> TYPE: DNA
<213> ORGANISM: artificial
<220> FEATURE:
<223> OTHER INFORMATION: Primer

<400> SEQUENCE: 14
acaccagtgc catctcggta                                                    20

<210> SEQ ID NO 15
<211> LENGTH: 16
<212> TYPE: DNA
<213> ORGANISM: artificial
<220> FEATURE:
<223> OTHER INFORMATION: Primer

<400> SEQUENCE: 15
cggagccgca gccota                                                        16

<210> SEQ ID NO 16
<211> LENGTH: 19
<212> TYPE: DNA
<213> ORGANISM: artificial
<220> FEATURE:
<223> OTHER INFORMATION: Primer

<400> SEQUENCE: 16
agatcgagaa cgagtgcgg                                                     19

<210> SEQ ID NO 17
<211> LENGTH: 19
<212> TYPE: DNA
<213> ORGANISM: artificial
<220> FEATURE:
<223> OTHER INFORMATION: Primer

<400> SEQUENCE: 17
agctgatgca gtccgagag                                                     19

<210> SEQ ID NO 18
<211> LENGTH: 19
<212> TYPE: DNA
<213> ORGANISM: artificial
<220> FEATURE:
<223> OTHER INFORMATION: Primer

<400> SEQUENCE: 18
ggtgggccac gatttctac                                                     19

<210> SEQ ID NO 19
<211> LENGTH: 25
<212> TYPE: DNA
<213> ORGANISM: artificial
<220> FEATURE:
<223> OTHER INFORMATION: Primer

<400> SEQUENCE: 19
tctgaagaac ggatatggtt ttgtg                                              25

<210> SEQ ID NO 20
<211> LENGTH: 20
<212> TYPE: DNA
<213> ORGANISM: artificial
<220> FEATURE:
<223> OTHER INFORMATION: Primer
```

<400> SEQUENCE: 20
ctcgctcacc acaaaggtct                                                   20

<210> SEQ ID NO 21
<211> LENGTH: 20
<212> TYPE: DNA
<213> ORGANISM: artificial
<220> FEATURE:
<223> OTHER INFORMATION: Primer

<400> SEQUENCE: 21
ctctcccgtc aacagcgttc                                                   20

<210> SEQ ID NO 22
<211> LENGTH: 22
<212> TYPE: DNA
<213> ORGANISM: artificial
<220> FEATURE:
<223> OTHER INFORMATION: Primer

<400> SEQUENCE: 22
gttgtgcata ttcttggctt gc                                                22

<210> SEQ ID NO 23
<211> LENGTH: 23
<212> TYPE: DNA
<213> ORGANISM: artificial
<220> FEATURE:
<223> OTHER INFORMATION: Primer

<400> SEQUENCE: 23
tgctgccatg aagtcagcga gag                                               23

<210> SEQ ID NO 24
<211> LENGTH: 20
<212> TYPE: DNA
<213> ORGANISM: artificial
<220> FEATURE:
<223> OTHER INFORMATION: Primer

<400> SEQUENCE: 24
ccagtgggcg caccctacag                                                   20

<210> SEQ ID NO 25
<211> LENGTH: 20
<212> TYPE: DNA
<213> ORGANISM: artificial
<220> FEATURE:
<223> OTHER INFORMATION: Primer

<400> SEQUENCE: 25
aagtggtgag gtcctggaaa                                                   20

<210> SEQ ID NO 26
<211> LENGTH: 20
<212> TYPE: DNA
<213> ORGANISM: artificial
<220> FEATURE:
<223> OTHER INFORMATION: Primer

<400> SEQUENCE: 26
ttccaacagt ggcagaaatg                                                   20

```
<210> SEQ ID NO 27
<211> LENGTH: 21
<212> TYPE: DNA
<213> ORGANISM: artificial
<220> FEATURE:
<223> OTHER INFORMATION: Primer

<400> SEQUENCE: 27
aatctgtcat gctggtctgc c                                              21

<210> SEQ ID NO 28
<211> LENGTH: 20
<212> TYPE: DNA
<213> ORGANISM: artificial
<220> FEATURE:
<223> OTHER INFORMATION: Primer

<400> SEQUENCE: 28
aggagatttg tttggcgtgc                                                20

<210> SEQ ID NO 29
<211> LENGTH: 19
<212> TYPE: DNA
<213> ORGANISM: artificial
<220> FEATURE:
<223> OTHER INFORMATION: Primer

<400> SEQUENCE: 29
atttgggtcg cggttcttg                                                 19

<210> SEQ ID NO 30
<211> LENGTH: 21
<212> TYPE: DNA
<213> ORGANISM: artificial
<220> FEATURE:
<223> OTHER INFORMATION: Primer

<400> SEQUENCE: 30
tgccttgaca ttctcgatgg t                                              21

<210> SEQ ID NO 31
<211> LENGTH: 24
<212> TYPE: DNA
<213> ORGANISM: artificial
<220> FEATURE:
<223> OTHER INFORMATION: Primer

<400> SEQUENCE: 31
acttttggta cattgtggct tcaa                                           24

<210> SEQ ID NO 32
<211> LENGTH: 20
<212> TYPE: DNA
<213> ORGANISM: artificial
<220> FEATURE:
<223> OTHER INFORMATION: Primer

<400> SEQUENCE: 32
ccgccaggac aaaccagtat                                                20

<210> SEQ ID NO 33
<211> LENGTH: 22
<212> TYPE: DNA
<213> ORGANISM: artificial
<220> FEATURE:
<223> OTHER INFORMATION: Primer
```

<400> SEQUENCE: 33
gaccgactga agcacggtgc aa                                         22

<210> SEQ ID NO 34
<211> LENGTH: 20
<212> TYPE: DNA
<213> ORGANISM: artificial
<220> FEATURE:
<223> OTHER INFORMATION: Primer

<400> SEQUENCE: 34
accaaggcag gccagcaacg                                            20

<210> SEQ ID NO 35
<211> LENGTH: 22
<212> TYPE: DNA
<213> ORGANISM: artificial
<220> FEATURE:
<223> OTHER INFORMATION: Primer

<400> SEQUENCE: 35
ttctgtgaaa gatccaagcc ct                                         22

<210> SEQ ID NO 36
<211> LENGTH: 22
<212> TYPE: DNA
<213> ORGANISM: artificial
<220> FEATURE:
<223> OTHER INFORMATION: Primer

<400> SEQUENCE: 36
agtctgagca gcatctgtgt ta                                         22

<210> SEQ ID NO 37
<211> LENGTH: 21
<212> TYPE: DNA
<213> ORGANISM: artificial
<220> FEATURE:
<223> OTHER INFORMATION: Primer

<400> SEQUENCE: 37
tgtgaaagat ccaagccctc t                                          21

<210> SEQ ID NO 38
<211> LENGTH: 20
<212> TYPE: DNA
<213> ORGANISM: artificial
<220> FEATURE:
<223> OTHER INFORMATION: Primer

<400> SEQUENCE: 38
tgttgcaccg tgctgtgtta                                            20

<210> SEQ ID NO 39
<211> LENGTH: 20
<212> TYPE: DNA
<213> ORGANISM: artificial
<220> FEATURE:
<223> OTHER INFORMATION: Primer

<400> SEQUENCE: 39 gaacccatt cacctcacgg                                             20

-continued

```
<210> SEQ ID NO 40
<211> LENGTH: 21
<212> TYPE: DNA
<213> ORGANISM: artificial
<220> FEATURE:
<223> OTHER INFORMATION: Primer

<400> SEQUENCE: 40
gaggtcaact ccaatgcgtt c                                            21

<210> SEQ ID NO 41
<211> LENGTH: 20
<212> TYPE: DNA
<213> ORGANISM: artificial
<220> FEATURE:
<223> OTHER INFORMATION: Primer

<400> SEQUENCE: 41
actcttgctc agcacctgtc                                              20

<210> SEQ ID NO 42
<211> LENGTH: 20
<212> TYPE: DNA
<213> ORGANISM: artificial
<220> FEATURE:
<223> OTHER INFORMATION: Primer

<400> SEQUENCE: 42 tcagggtca tacactgtgg                                               20

<210> SEQ ID NO 43
<211> LENGTH: 20
<212> TYPE: DNA
<213> ORGANISM: artificial
<220> FEATURE:
<223> OTHER INFORMATION: Primer

<400> SEQUENCE: 43
ggaggcaaga tggtgttgga                                              20

<210> SEQ ID NO 44
<211> LENGTH: 20
<212> TYPE: DNA
<213> ORGANISM: artificial
<220> FEATURE:
<223> OTHER INFORMATION: Primer

<400> SEQUENCE: 44
acagtcattg gccagtgtga                                              20

<210> SEQ ID NO 45
<211> LENGTH: 20
<212> TYPE: DNA
<213> ORGANISM: artificial
<220> FEATURE:
<223> OTHER INFORMATION: Primer

<400> SEQUENCE: 45
tgtggtggag atcttttggg                                              20

<210> SEQ ID NO 46
<211> LENGTH: 18
<212> TYPE: DNA
<213> ORGANISM: artificial
<220> FEATURE:
<223> OTHER INFORMATION: Primer
```

```
<400> SEQUENCE: 46
gcagtgtggg gatatcgt                                           18

<210> SEQ ID NO 47
<211> LENGTH: 21
<212> TYPE: DNA
<213> ORGANISM: artificial
<220> FEATURE:
<223> OTHER INFORMATION: Primer

<400> SEQUENCE: 47
tgccatgtag accccttgaa g                                       21

<210> SEQ ID NO 48
<211> LENGTH: 21
<212> TYPE: DNA
<213> ORGANISM: artificial
<220> FEATURE:
<223> OTHER INFORMATION: Primer

<400> SEQUENCE: 48
atggtacatg acaaggtgcg g                                       21

<210> SEQ ID NO 49
<211> LENGTH: 20
<212> TYPE: DNA
<213> ORGANISM: artificial
<220> FEATURE:
<223> OTHER INFORMATION: Primer

<400> SEQUENCE: 49
tgtggtggag atcttttggg                                         20

<210> SEQ ID NO 50
<211> LENGTH: 22
<212> TYPE: DNA
<213> ORGANISM: artificial
<220> FEATURE:
<223> OTHER INFORMATION: Primer

<400> SEQUENCE: 50
tcagttcttt ttctgggatt gg                                      22

<210> SEQ ID NO 51
<211> LENGTH: 21
<212> TYPE: DNA
<213> ORGANISM: artificial
<220> FEATURE:
<223> OTHER INFORMATION: Primer

<400> SEQUENCE: 51
aggttgtctc ctgcgacttc a                                       21

<210> SEQ ID NO 52
<211> LENGTH: 22
<212> TYPE: DNA
<213> ORGANISM: artificial
<220> FEATURE:
<223> OTHER INFORMATION: Primer

<400> SEQUENCE: 52
ggtggtccag ggtttcttac tc                                      22
```

```
<210> SEQ ID NO 53
<211> LENGTH: 25
<212> TYPE: DNA
<213> ORGANISM: artificial
<220> FEATURE:
<223> OTHER INFORMATION: Primer

<400> SEQUENCE: 53
cggtgtgtgt atcattctct agtgt                                        25

<210> SEQ ID NO 54
<211> LENGTH: 25
<212> TYPE: DNA
<213> ORGANISM: artificial
<220> FEATURE:
<223> OTHER INFORMATION: Primer

<400> SEQUENCE: 54
cgtgtggtga ttttaccttc agttg                                        25

<210> SEQ ID NO 55
<211> LENGTH: 25
<212> TYPE: DNA
<213> ORGANISM: artificial
<220> FEATURE:
<223> OTHER INFORMATION: Primer

<400> SEQUENCE: 55
ttgcacgagt gcaaaaggtc ttcat                                        25

<210> SEQ ID NO 56
<211> LENGTH: 25
<212> TYPE: DNA
<213> ORGANISM: artificial
<220> FEATURE:
<223> OTHER INFORMATION: Primer

<400> SEQUENCE: 56
gcgagagtct gagcagcatc tggat                                        25

<210> SEQ ID NO 57
<211> LENGTH: 25
<212> TYPE: DNA
<213> ORGANISM: artificial
<220> FEATURE:
<223> OTHER INFORMATION: Primer

<400> SEQUENCE: 57
atatccatac tgtgatcctg tgcga                                        25

<210> SEQ ID NO 58
<211> LENGTH: 25
<212> TYPE: DNA
<213> ORGANISM: artificial
<220> FEATURE:
<223> OTHER INFORMATION: Primer

<400> SEQUENCE: 58
taccttcagt tggtcttgac ttgga                                        25

<210> SEQ ID NO 59
<211> LENGTH: 25
<212> TYPE: DNA
<213> ORGANISM: artificial
<220> FEATURE:
<223> OTHER INFORMATION: Primer
```

-continued

<400> SEQUENCE: 59
accgtgtggt gattttacct tcagt             25

<210> SEQ ID NO 60
<211> LENGTH: 25
<212> TYPE: DNA
<213> ORGANISM: artificial
<220> FEATURE:
<223> OTHER INFORMATION: Primer

<400> SEQUENCE: 60
cgtgtggtga ttttaccttc agttg             25

<210> SEQ ID NO 61
<211> LENGTH: 25
<212> TYPE: DNA
<213> ORGANISM: artificial
<220> FEATURE:
<223> OTHER INFORMATION: Primer

<400> SEQUENCE: 61
aagaaagaat cttgtcactt tagcc             25

<210> SEQ ID NO 62
<211> LENGTH: 24
<212> TYPE: DNA
<213> ORGANISM: artificial
<220> FEATURE:
<223> OTHER INFORMATION: Primer

<400> SEQUENCE: 62
gggatatcgt cttctgtagt tctt              24

<210> SEQ ID NO 63
<211> LENGTH: 26
<212> TYPE: DNA
<213> ORGANISM: artificial
<220> FEATURE:
<223> OTHER INFORMATION: Primer

<400> SEQUENCE: 63
actgctacta cagcaaagtg cagagg            26

<210> SEQ ID NO 64
<211> LENGTH: 28
<212> TYPE: DNA
<213> ORGANISM: artificial
<220> FEATURE:
<223> OTHER INFORMATION: Primer

<400> SEQUENCE: 64
cactttgctt cagttggtct tgacttgg          28

<210> SEQ ID NO 65
<211> LENGTH: 21
<212> TYPE: DNA
<213> ORGANISM: artificial
<220> FEATURE:
<223> OTHER INFORMATION: Primer

<400> SEQUENCE: 65
gatatggcct gtcttggtct t                 21

```
<210> SEQ ID NO 66
<211> LENGTH: 22
<212> TYPE: DNA
<213> ORGANISM: artificial
<220> FEATURE:
<223> OTHER INFORMATION: Primer

<400> SEQUENCE: 66
gccaggttta gtccctagaa at                                        22

<210> SEQ ID NO 67
<211> LENGTH: 23
<212> TYPE: DNA
<213> ORGANISM: artificial
<220> FEATURE:
<223> OTHER INFORMATION: Primer

<400> SEQUENCE: 67
agtcaagacc aactgaaggt aaa                                       23

<210> SEQ ID NO 68
<211> LENGTH: 23
<212> TYPE: DNA
<213> ORGANISM: artificial
<220> FEATURE:
<223> OTHER INFORMATION: Primer

<400> SEQUENCE: 68
tccaagatcc ataggtacag aga                                       23

<210> SEQ ID NO 69
<211> LENGTH: 21
<212> TYPE: DNA
<213> ORGANISM: artificial
<220> FEATURE:
<223> OTHER INFORMATION: Primer

<400> SEQUENCE: 69
cgccaaccaa ctaaatccaa c                                         21

<210> SEQ ID NO 70
<211> LENGTH: 22
<212> TYPE: DNA
<213> ORGANISM: artificial
<220> FEATURE:
<223> OTHER INFORMATION: Primer

<400> SEQUENCE: 70
aagctagaaa tggtgaggtg ag                                        22

<210> SEQ ID NO 71
<211> LENGTH: 26
<212> TYPE: DNA
<213> ORGANISM: artificial
<220> FEATURE:
<223> OTHER INFORMATION: Primer

<400> SEQUENCE: 71
aaaaaaaaaa acactagaga atgata                                    26

<210> SEQ ID NO 72
<211> LENGTH: 26
<212> TYPE: DNA
<213> ORGANISM: artificial
<220> FEATURE:
<223> OTHER INFORMATION: Primer
```

```
<400> SEQUENCE: 72
aaaaaaaaaa caactgaagg taaaat                                                26
```